(12) United States Patent
Takata et al.

(10) Patent No.: US 11,749,413 B2
(45) Date of Patent: *Sep. 5, 2023

(54) METHOD FOR CONTROLLING INFORMATION TERMINAL, AND RECORDING MEDIUM

(71) Applicant: Panasonic Corporation, Osaka (JP)

(72) Inventors: Kazutoyo Takata, Fukui (JP); Kazuki Kozuka, Fukui (JP); Kenji Kondo, Fukui (JP); Hirohiko Kimura, Fukui (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 99 days.

This patent is subject to a terminal disclaimer.

(21) Appl. No.: 16/926,970

(22) Filed: Jul. 13, 2020

(65) Prior Publication Data

US 2020/0342998 A1 Oct. 29, 2020

Related U.S. Application Data

(63) Continuation of application No. 14/876,596, filed on Oct. 6, 2015, now Pat. No. 10,748,661.

(30) Foreign Application Priority Data

Oct. 30, 2014 (JP) .................. 2014-221224

(51) Int. Cl.
*G16H 50/70* (2018.01)
*G16H 30/40* (2018.01)
(Continued)

(52) U.S. Cl.
CPC ............. *G16H 50/70* (2018.01); *G16H 30/20* (2018.01); *G16H 30/40* (2018.01); *G16H 70/00* (2018.01); *G16H 70/60* (2018.01)

(58) Field of Classification Search
CPC ........ G16H 50/70; G16H 30/00; G16H 30/20; G16H 30/40; G16H 70/60; G16H 15/00; A61B 6/463; A61B 6/465

See application file for complete search history.

(56) References Cited

U.S. PATENT DOCUMENTS

| 8,775,208 B2* | 7/2014 | Hertel | G16H 15/00 600/300 |
|---|---|---|---|
| 2002/0021828 A1* | 2/2002 | Papier | G16H 50/20 382/128 |

(Continued)

FOREIGN PATENT DOCUMENTS

| JP | 2008-102665 | 5/2008 |
|---|---|---|
| JP | 2011-118540 | 6/2011 |
| JP | 2014-039852 | 3/2014 |

OTHER PUBLICATIONS

Quellec, Gwénolé, et al. "Medical case retrieval from a committee of decision trees." IEEE Transactions on Information Technology in Biomedicine 14.5 (2010): 1227-1235.

*Primary Examiner* — Mark Holcomb
(74) *Attorney, Agent, or Firm* — Wenderoth, Lind & Ponack, L.L.P.

(57) ABSTRACT

A display screen including a first display area displaying plural similar medical images received from a case search system and a second display area displaying disease names is displayed on a display of an information terminal. Each similar medical image is a medical image contained in an electronic medical book, and has additional information which includes the number of a page containing the similar medical image. If the user's selection of a similar medical image is detected for the first time after the display of the display screen, a page of an electronic medical book containing the selected similar medical image is displayed on the display screen. If the user's selection of a disease name (Continued)

is detected for the first time after the display of the display screen, a page of an electronic medical book containing differential items corresponding to the selected disease name is displayed on the display screen.

3 Claims, 60 Drawing Sheets

(51) Int. Cl.
*G16H 70/60* (2018.01)
*G16H 30/20* (2018.01)
*G16H 70/00* (2018.01)

(56) References Cited

U.S. PATENT DOCUMENTS

| | | |
|---|---|---|
| 2005/0043966 A1 | 2/2005 | Harnsberger |
| 2006/0147099 A1* | 7/2006 | Marshall ............... G16H 50/20 |
| | | 382/128 |
| 2008/0095418 A1 | 4/2008 | Moriya |
| 2009/0083072 A1* | 3/2009 | Osawa ................. G16H 70/60 |
| | | 705/2 |
| 2011/0099032 A1 | 4/2011 | Miyasa et al. |
| 2014/0016845 A1 | 1/2014 | Gazit |
| 2015/0317434 A1* | 11/2015 | Kondo .................... A61B 5/00 |
| | | 705/3 |

* cited by examiner

| | | |
|---|---|---|
| 411 | MEDICAL BOOK ID | 000013 |
| 412 | PATH TO MEDICAL BOOK | \\192.168.xxx.xxx\\doc\\000013.pdf |
| 413 | TITLE OF BOOK | FUNDAMENTALS OF DIAGNOSTIC CT IMAGING |
| 414 | PATH TO COVER IMAGE | \\192.168.xxx.xxx\\img\\000013.png |

| | | |
|---|---|---|
| 421 | MEDICAL BOOK ID | 000013 |
| 422 | PATH | 192.168.xxx.xxx/image/000013_23.png |
| 423 | IMAGE ID | 000013_23 |
| 424 | DEFINITELY DIAGNOSED DISEASE NAME | ASPERGILLOSIS |
| 425 | PAGE NUMBER | 210 |
| 426 | LINE NUMBER | 7 |

430

| 431 | MEDICAL BOOK ID | 000013 |
| --- | --- | --- |
| 432 | DISEASE NAME | ASPERGILLOSIS |
| 433 | DIFFERENTIAL ITEMS | (1) Upper lobe consolidation similar to tuberculosis<br>(2) Cavitation of nodule<br>(3) Enlargement of pleura |
| 434 | PAGE NUMBER | 206 |
| 435 | LINE NUMBER | 1 |

FIG. 11

| DISEASE NAME LIST | | 730 |
|---|---|---|
| MYCOSIS | 14 | 731 |
| ASPERGILLOSIS | 8 | 732 |
| CRYPTOCOCCOSIS | 6 | 733 |
| NEOPLASTIC | 13 | 734 |
| LUNG CANCER | 10 | 735 |
| METASTATIC LUNG CANCER | 3 | 736 |
| NONNEOPLASTIC | 6 | 737 |
| LUNG ABSCESS | 4 | 738 |
| SARCOIDOSIS | 1 | 739 |
| SEPTIC EMBOLI | 1 | 740 |
| MYCOBACTERIOSIS | 6 | 741 |
| NONTUBERCULOUS MYCOBACTERIA (NTM) | 4 | 742 |
| TUBERCULOSIS | 2 | 743 |
| OTHERS | 2 | 744 |
| BRONCHIECTASIS | 1 | 745 |
| ... | 1 | |

FIG. 18

62 RESULTS (713) ALL DISEASES AND DISORDERS (714)

DISEASE NAME LIST (730)

| MYCOSIS | 14 |
| --- | --- |
| ASPERGILLOSIS | 8 |
| CRYPTOCOCCOSIS | 6 |
| NEOPLASTIC | 13 |
| LUNG CANCER | 10 |
| METASTATIC LUNG CANCER | 3 |
| NONNEOPLASTIC | 6 |
| LUNG ABSCESS | 4 |
| INFLAMMATORY NODULES | 1 |

LESION DISTRIBUTION (750)

☐ DIFFUSE ☐ MULTIPLE
☒ SEGMENTAL ☒ SUBPLEURAL
☐ BRONCHIAL ☐ HEMATOGENOUS
☐ BILATERAL

DISPLAY (720)

(721, 722, 723, 724)

--- p.206 (763)

3. Aspergillosis

General Knowledge and CT Findings of Aspergillosis

■ Chronic necrotizing aspergillosis
(1) Upper lobe consolidation similar to tuberculosis
(2) Cavitation of nodule
(3) Enlargement of pleura
(4) Rapid progress with formation of a cavity in approx. 2 weeks ■ Angioinvasive aspergillosis
(1) Well-defined nodule with halo sign or localized consolidation
(2) Cavitated nodule with air crescent sign ■ Airway-invasive aspergillosis
(1) Patchy peribronchial consolidation
(2) Ill-defined nodule
(3) Centrilobular nodules
(4) Tree-in-bud
(5) Often occurring in immunosuppressed patients

--- p.210 (761, 760, 764, 770, K2)

Fig. 3-4  Example of Aspergillosis

A cavity tumor is observed in the right upper lobe, which is similar to cavernous tuberculosis. The patient is a 57-year-old male who developed severe neutropenia after undergoing chemotherapy in chronic myeloid leukemia.

Of the patients of 7 cases in which consolidation was identified, cavity formation was observed in 3 cases, and a nodular opacity was observed in 2 cases (Fig. 3-4). Histologically, intraalveolar hemorrhage was observed and aspergillosis was included. Further, various degrees of central necrosis were found and inflammatory ... (762)

LESION DISTRIBUTION  ╭─750
☑ DIFFUSE ─751    ☐ MULTIPLE ─755
▓ SEGMENTAL ─752  ▓ SUBPLEURAL ─756
☐ BRONCHIAL ─753  ☑ HEMATOGENOUS ─757
☐ BILATERAL ─754

| | | |
|---|---|---|
| 1100 | PATIENT ID | 123456 |
| 1200 | NAME | JOHN DOE |
| 1300 | AGE | 28 |
| 1400 | GENDER | MALE |
| 1500 | PAST MEDICAL HISTORY | NO |
| 1600 | FAMILY HISTORY | NO |
| 1700 | CHIEF COMPLAINT | COUGH |
| 1800 | TEST INFORMATION | (SEE FIG. 29) |
| 1900 | DEFINITE DIAGNOSIS | MYCOPLASMA PNEUMONIAE |

| | | |
|---|---|---|
| 1810 | TEST ID | 13227895 |
| 1820 | TEST DATE | 10:00 AM FEBRUARY 5, 20XX |
| 1830 | TEST TYPE | BLOOD TEST |
| 1840 | TEST RESULT | YYYY1 |

| | |
|---|---|
| TEST ID | 13227903 |
| TEST DATE | 11:00 AM FEBRUARY 5, 20XX |
| TEST TYPE | SIMPLE X-RAY (CHEST) |
| TEST RESULT | YYYY2 |

| | |
|---|---|
| TEST ID | 13227989 |
| TEST DATE | 9:00 AM FEBRUARY 9, 20XX |
| TEST TYPE | CT (CHEST) |
| TEST RESULT | YYYY3 |

| | | |
|---|---|---|
| 1810 — TEST ID | 13227989 | |
| 3100 — FINDINGS | MULTIPLE NODULES OF 0.5 TO 1.0 cm IN THE RIGHT LUNG FIELD WERE ... | |
| 3200 — DIAGNOSIS | INFLAMMATORY NODULES OR TUBERCULOSIS IS SUSPECTED. | |

| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ... | ... | ... | ... |
| 235982 | ... | ... | ... | ... |

800

| SERIES ID | DEFINITION | IMAGE |
|---|---|---|
|  |  |  |
|  |  |  |
|  |  |  |

| PATIENT ID | PATIENT NAME | TEST DATE | TEST ID | TEST TYPE |
|---|---|---|---|---|
| 443982 | RICHARD ROE | DEC 1, 20XX | 23982874 | MR (HEAD) |
| 123456 | JOHN DOE | MAY 8, 20XX | 13227989 | CT (CHEST) |
| 345455 | ... | ... | ... | ... |
| 235982 | ... | ... | ... | ... |

| SERIES ID | DEFINITION | IMAGE |
|---|---|---|
| CT152729 | PULMONARY CONDITION SLICE THICKNESS: 5 mm | |
| CT152730 | PULMONARY CONDITION SLICE THICKNESS: 1 mm | |
| CT152731 | MEDIASTINAL CONDITION SLICE THICKNESS: 5 mm | |

| NUMBER OF ROWS | 2 |
|---|---|
| NUMBER OF COLUMNS | 2 |

~ 4411

| POSITION | SLICE ID |
|---|---|
| FIRST ROW AND FIRST COLUMN | CT12353515 |
| FIRST ROW AND SECOND COLUMN | — |
| SECOND ROW AND FIRST COLUMN | — |
| SECOND ROW AND SECOND COLUMN | — |

| DISEASE NAME ID | MAJOR-CATEGORY DISEASE NAME | SUBCATEGORY DISEASE NAME | NUMBER OF RESULTS | SIMILAR CASE ID |
|---|---|---|---|---|
| DIS528 | NEOPLASTIC | LUNG CANCER | 10 | SIM258, SIM551, SIM1209, SIM2341, ... |
| DIS922 | MYCOSIS | ASPERGILLOSIS | 8 | ... |
| ... | MYCOSIS | CRYPTOCOCCOSIS | 6 | ... |
| ... | NONNEOPLASTIC | LUNG ABSCESS | 4 | ... |
| ... | MYCOBACTERIOSIS | NONTUBERCULOUS MYCOBACTERIA (NTM) | 4 | ... |
| ... | ... | ... | ... | ... |

FIG. 43

| DISEASE NAME LIST 730 | |
|---|---|
| LUNG CANCER | 10 |
| ASPERGILLOSIS | 8 |
| CRYPTOCOCCOSIS | 6 |
| LUNG ABSCESS | 4 |
| NONTUBERCULOUS MYCOBACTERIA (NTM) | 4 |
| METASTATIC LUNG CANCER | 3 |
| TUBERCULOSIS | 2 |
| INFLAMMATORY NODULES | 1 |
| SEPTIC EMBOLI | 1 |
| BRONCHIECTASIS | 1 |
| UNKNOWN | 1 |

FIG. 44

| DISEASE NAME LIST 730 | |
|---|---|
| MYCOSIS | 14 |
| NEOPLASTIC | 13 |
| NONNEOPLASTIC | 6 |
| MYCOBACTERIOSIS | 6 |
| OTHERS | 2 |

FIG. 45

| DISEASE NAME LIST | 730 |
|---|---|
| MYCOSIS | 14 |
| ASPERGILLOSIS | 8 |
| CRYPTOCOCCOSIS | 6 |
| NEOPLASTIC | 13 |
| LUNG CANCER | 10 |
| METASTATIC LUNG CANCER | 3 |
| NONNEOPLASTIC | 6 |
| LUNG ABSCESS | 4 |
| SARCOIDOSIS | 1 |
| SEPTIC EMBOLI | 1 |
| MYCOBACTERIOSIS | 6 |
| NONTUBERCULOUS MYCOBACTERIA (NTM) | 4 |
| TUBERCULOSIS | 2 |
| OTHERS | 2 |
| BRONCHIECTASIS | 1 |
| ... | 1 |

FIG. 47

| NAME OF DISTRIBUTION | NUMBER OF CASES | SIMILAR CASE ID |
|---|---|---|
| DIFFUSE | 3 | SIM2521, SIM4123, SIM5225 |
| SEGMENTAL | 0 | NO CASE |
| BRONCHIAL | 2 | SIM0006, SIM1892, SIM4399 |
| BILATERAL | 12 | ... |
| MULTIPLE | 22 | ... |
| SUBPLEURAL | 0 | NO CASE |
| HEMATOGENOUS | 5 | ... |

METHOD FOR CONTROLLING INFORMATION TERMINAL, AND RECORDING MEDIUM

BACKGROUND

1. Technical Field

The present disclosure relates to a method for controlling an information terminal for searching for similar medical images that are similar to a medical image to be interpreted, and to a recording medium.

2. Description of the Related Art

Medical imaging devices such as computed tomography (CT) and magnetic resonance imaging (MRI) devices have been developed and used widely in recent years. The advent of CT, MRI, and the like has enabled acquisition of a large number of high-definition digital medical images. In addition, medical images interpreted by radiologists are sequentially accumulated together with interpretation reports in picture archiving and communication systems (PACSs).

For instance, as disclosed in Japanese Unexamined Patent Application Publication No. 2011-118540, the development of a technique for image retrieval has been started. In this technique, previous medical images that are similar to a medical image to be interpreted are searched for in the records of previous cases accumulated in a PACS for the reference of new image interpretation.

However, further improvements have been needed.

SUMMARY

In one general aspect, the techniques disclosed here feature a method for controlling an information terminal for connection to a case search system that searches for a medical image with reference to a medical image database having medical images registered therein, the information terminal including a display and a computer. The method includes causing the computer of the information terminal to receive, from the case search system, a plurality of similar medical images each having a predetermined similarity to a target medical image that is a medical image to be interpreted, each of the plurality of similar medical images being a medical image contained in an electronic medical book and having additional information, the additional information of each of the plurality of similar medical images including a disease name corresponding to the similar medical image and a number of a page of the electronic medical book which contains the similar medical image, the page of the electronic medical book which contains the similar medical image describing diagnostic information related to the similar medical image and used to identify the disease name; causing the computer of the information terminal to display a display screen including a first display area and a second display area on the display, the first display area displaying the received plurality of similar medical images, the second display area displaying one or more disease names, each having additional information, the additional information of each of the one or more disease names displayed in the second display area including a number of a page of the electronic medical book which contains differential items corresponding to the disease name; causing the computer of the information terminal to, in a case where a user's selection detected for the first time after the display screen has been displayed is a selection of a similar medical image among the plurality of similar medical images displayed in the first display area, display, on the display screen, a page of the electronic medical book which contains the selected similar medical image; and causing the computer of the information terminal to, in a case where a user's selection detected for the first time after the display screen has been displayed is a selection of a disease name among the one or more disease names displayed in the second display area, display, on the display screen, a page of the electronic medical book which contains the differential items corresponding to the selected disease name.

In an aspect of the present disclosure, a further improvement is achievable.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram illustrating the data configuration of medical book data;

FIG. 5 is a diagram illustrating the data configuration of a medical book image data;

FIG. 11 is an enlarged view of a disease name list display area;

FIG. 18 is a diagram illustrating another example of the basic screen on which the similar case data display area is used in its entirety as a medical book display area;

FIG. 19 is a diagram illustrating an example of a basic screen on which a selected similar case is displayed in the medical book display area in a highlighted manner;

FIG. 26 is a diagram illustrating a distribution list display area in which a plurality of checkboxes are checked;

FIG. 28 is a diagram illustrating the data configuration of patient information;

FIG. 29 is a diagram illustrating the data configuration of test information registered in the patient information illustrated in FIG. 28;

FIG. 31 is a diagram illustrating the data configuration of a diagnostic report;

FIG. 35 is a view of a screen for a test list;

FIG. 36 is a view of a screen for a test list after a test has been selected;

FIG. 40 is a diagram illustrating the data configuration of display box management information;

FIG. 42 is a diagram illustrating the data configuration of a disease name list generated in S1300 in FIG. 41;

FIG. 43 is a diagram illustrating a first example display of a disease name list display area;

FIG. 44 is a diagram illustrating a second example display of the disease name list display area;

FIG. 45 is a diagram illustrating a third example display of the disease name list display area;

FIG. 47 is a diagram illustrating the data configuration of a distribution list generated in S1400 in FIG. 41;

DETAILED DESCRIPTION

Underlying Knowledge of Present Disclosure

Figure 1:
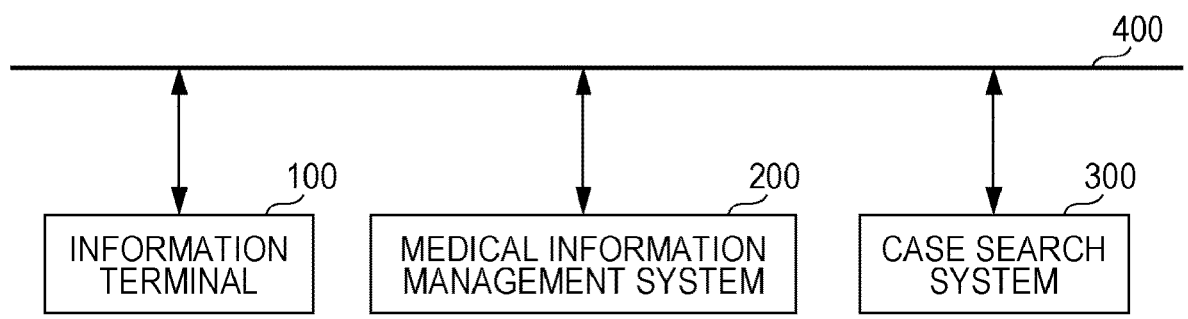
FIG. 1 is an overall configuration diagram of a hospital information system in which an information terminal according to this embodiment is used.

First, a description will be given of issues pertaining to an aspect of the present disclosure.

Japanese Unexamined Patent Application Publication No. 2011-118540 discloses a case search apparatus for providing a case search in which a comprehensive list of diseases is made. It is also disclosed that the case search apparatus searches through case images in an electronic medical book database (Claim 8 and paragraph [0030] in Japanese Unexamined Patent Application Publication No. 2011-118540). It is further disclosed that a display screen on which search results are displayed provides display of case information such as an image-based diagnostic name, and also provides display of medical information and the like included in an electronic medical book to which the case information is linked. It is also disclosed that a radiologist is able to select items to be displayed by using an operation device such as a keyboard (paragraph [0062] in Japanese Unexamined Patent Application Publication No. 2011-118540).

According to Japanese Unexamined Patent Application Publication No. 2011-118540, therefore, medical information to be displayed on the display screen can be determined in accordance with a selection made by a radiologist. That is, no medical information is displayed on the display screen until the radiologist selects the medical information that they desire. This requires the radiologist to perform an operation each time the radiologist desires to access medical information, which may cause a reduction in diagnostic efficiency. This can result in a reduction in diagnostic accuracy.

Japanese Unexamined Patent Application Publication No. 2014-39852 discloses an information processing apparatus for changing the way in which similar cases are displayed in accordance with the need for the presentation of the similar cases. The information processing apparatus displays medical reference information in the right portion of a diagnostic screen for displaying similar cases. In the case of easy diagnosis of a target image to be diagnosed, the information processing apparatus presents no similar cases when initially displaying the diagnostic screen but displays medical reference information for efficient use of an unused spare display area. When a similar case display button displayed on the diagnostic screen is pressed, the information processing apparatus replaces the medical reference information with similar cases for display (paragraph [0063] and FIG. 4 in Japanese Unexamined Patent Application Publication No. 2014-39852). This prevents a radiologist from getting annoyed due to unnecessary display of similar cases in the case of the ease of diagnosis of the target image to be diagnosed.

Accordingly, Japanese Unexamined Patent Application Publication No. 2014-39852 focuses on no similar cases being displayed on the diagnostic screen to prevent the radiologist from becoming annoyed. That is, Japanese Unexamined Patent Application Publication No. 2014-39852 does not describe the concept of effective presentation, to a radiologist who is searching for similar cases, of medical information of an electronic medical book which may be needed by the radiologist.

Japanese Unexamined Patent Application Publication No. 2008-102665 discloses a medical image interpretation support system for changing the number of similar case images to be displayed in accordance with the number of times an image-based diagnosis has been performed or the progress of the image-based diagnosis. It is disclosed that the medical image interpretation support system displays medical information on a monitor if the image to be interpreted is a target image of the first examination (Claim 2, paragraph [0057], and FIG. 8(a) in Japanese Unexamined Patent Application Publication No. 2008-102665).

Accordingly, image information regarding appropriate content is efficiently presented to a radiologist when the image to be interpreted is a target image of the first examination (paragraph [0059] in Japanese Unexamined Patent Application Publication No. 2008-102665).

According to Japanese Unexamined Patent Application Publication No. 2008-102665, whether to display medical information is determined in accordance with whether the image to be interpreted is a target image of the first examination. That is, there is no description of the concept that medical information which may be needed by a radiologist who is searching for similar cases is estimated from an enormous amount of medical information on the basis of information input from the radiologist and is presented to the radiologist.

As a result of the foregoing discussion, the present inventors have contemplated the following aspects.

An aspect of the present disclosure provides a method for controlling an information terminal for connection to a case search system that searches for a medical image with reference to a medical image database having medical images registered therein, the information terminal including a display and a computer, the method including:

causing the computer of the information terminal to receive, from the case search system, a plurality of similar medical images each having a predetermined similarity to a target medical image that is a medical image to be interpreted, each of the plurality of similar medical images being a medical image contained in an electronic medical book and having additional information, the additional information of each of the plurality of similar medical images including a disease name corresponding to the similar medical image and a number of a page of the electronic medical book which contains the similar medical image, the page of the electronic medical book which contains the similar medical image describing diagnostic information related to the similar medical image and used to identify the disease name;

causing the computer of the information terminal to display a display screen including a first display area and a second display area on the display, the first display area displaying the received plurality of similar medical images, the second display area displaying one or more disease names, each having additional information, the additional information of each of the one or more disease names displayed in the second display area including a number of a page of the electronic medical book which contains differential items corresponding to the disease name;

causing the computer of the information terminal to, in a case where a user's selection detected for the first time after the display screen has been displayed is a selection of a similar medical image among the plurality of similar medical images displayed in the first display area, display, on the display screen, a page of the electronic medical book which contains the selected similar medical image; and causing the computer of the information terminal to, in a case where a user's selection detected for the first time after the display screen has been displayed is a selection of a disease name among the one or more disease names displayed in the second display area, display, on the display screen, a page of the electronic medical book which contains the differential items corresponding to the selected disease name.

In general, in order to study a lesion appearing in a target medical image that is a medical image to be interpreted in which the name of the disease is unidentified, it is likely to be efficient to refer to a similar medical image that is similar to the target medical image among other medical images in which the names of the diseases are identified. In particular, medical books that radiologists use for the diagnosis of medical images describe the details of information necessary to identify the names of the diseases in medical images contained in the medical books in correspondence with the medical images. Thus, such information is useful to study the lesion in the medical image to be interpreted.

According to this aspect, a similar medical image which has a predetermined similarity to the target medical image and for which a disease name has already been identified is received from the case search system, and the received similar medical image is displayed on a display. Thus, a similar medical image which is usable for reference for studying the lesion appearing on the target medical image to identify the name of the disease can be efficiently extracted from among an enormous collection of medical images registered in the medical image database, and presented to a radiologist.

According to this aspect, furthermore, if a user's selection detected for the first time after a display screen displaying a similar medical image has been displayed on a display is a selection of a similar medical image displayed in the first display area, a page of the electronic medical book which contains the selected similar medical image is displayed on the display screen. On the other hand, if a user's selection detected for the first time after the display screen displaying a similar medical image has been displayed on the display is a selection of a disease name displayed in the second display area, a page of the electronic medical book which contains differential items corresponding to the selected disease name is displayed on the display screen.

Here, there may be mainly two situations where a radiologist searches for a similar medical image that is similar to the target medical image by using the case search system, as follows.

In the first situation, the radiologist wishes to see, for reference, disease names assigned to similar medical images that are similar to the target medical image because they do not come up with the disease name for the target medical image when viewing the target medical image. In this case, in a typical medical setting, the radiologist retrieves a medical image that is similar to the target medical image from among an enormous collection of medical images contained in medical books to determine the name of the disease in the target medical image by using, as a reference, the disease name assigned to the similar medical image.

Here, if a user's selection detected for the first time after a display screen that includes a first display area displaying the received plurality of similar medical images and a second display area displaying disease names has been displayed on the display is a selection of a similar medical image displayed in the first display area, it can be presumed the radiologist might not have come up with the disease name for the target medical image. In this case, a page of an electronic medical book which contains the selected similar medical image and which describes diagnostic information on the selected similar medical image may be displayed. This is because, when comparing a target medical image with a similar medical image, the radiologist compares the features of the medical images also taking into account diagnostic information concerning the similar medical image.

The diagnostic information includes, for example, a type of lesion pattern (such as nodal or diffuse) in the similar medical image, patient clinical information (such as gender, age, and blood test results) regarding the similar medical image, and the patient's follow-up information. That is, the diagnostic information is as important as or more important than similarity of features of medical images in terms of comparison between a target medical image and a similar medical image.

The diagnostic information is described in the electronic medical book at a location adjacent to the medical image.

According to this aspect, in response to the detection of a selection of a similar medical image displayed in the first display area, a page of the electronic medical book which contains the selected similar medical image is displayed on a display screen. Thus, when a similar medical image is selected, diagnostic information concerning the selected similar medical image can be automatically presented to the radiologist. In addition, since diagnostic information is automatically presented to the radiologist, overlooking of the diagnostic information can be avoided. In an actual diagnostic setting, even in a case where a target medical image and a selected similar medical image are similar to each other in terms of image features, it may be concluded that, as a result of consideration of the diagnostic information, the two images are images of different diseases. Thus, according to this aspect, overlooking of diagnostic information can be effectively avoided, leading to the prevention of misdiagnosis.

In the second situation, the radiologist comes up with a plurality of possible disease names for a target medical image when viewing the target medical image, and wishes to obtain information necessary to determine which of the possible disease names is correct. In this case, in a typical medical setting, the radiologist reads a medical book page for each of the plurality of disease names thought of by the radiologist, and checks differential items serving as information necessary to determine the name of the disease. By checking the target medical image and the differential items in detail, the radiologist eventually defines the name of the disease in the target medical image.

Here, if a user's selection detected for the first time after a display screen that includes a first display area displaying the received plurality of similar medical images and a second display area displaying disease names has been displayed on the display is a selection of a disease name displayed in the second display area, it can be presumed that the radiologist might have come up with a plurality of possible disease names for the target medical image. Thus, upon detection of the selection of a disease name displayed in the second display area, information necessary to determine which of the plurality of possible disease names is correct may be presented to the radiologist in view of efficient diagnosis. That is, differential items that are information necessary for determining a specific disease name may be presented.

According to this aspect, upon detection of the selection of a disease name displayed in the second display area, a page of the electronic medical book which contains the differential items corresponding to the selected disease name is displayed on a display screen. Thus, information necessary for diagnosis, which is desired by the radiologist, can be effectively presented.

As described above, it is presumably determined which of the two situations described above is the current situation in accordance with the content of the user's selection detected for the first time after a display screen that includes a first display area displaying the received plurality of similar medical images and a second display area displaying disease names has been displayed on the display.

In addition, information necessary for diagnosis, which is suitable for each situation, can be presented to the radiologist. This can save the radiologist time and labor involved in searching for necessary information from electronic medical books. In addition, making the radiologist concentrate on making a decision about diagnosis and treatment can improve the accuracy of the decision about diagnosis and treatment.

In addition, in the aspect described above, for example, a page of the electronic medical book to be displayed on the display screen may be displayed in a portion of the first display area.

In addition, in the aspect described above, for example, in a case where the page of the electronic medical book which contains the differential items corresponding to the selected disease name is to be displayed on the display screen, the plurality of similar medical images displayed in the first display area may be removed and the page of the electronic medical book which contains the differential items corresponding to the selected disease name may be displayed in an entire area of the first display area.

In this aspect, the page of the electronic medical book which contains the differential items corresponding to the selected disease name is displayed on the display screen in a case where a user's selection detected for the first time after a display screen that includes a first display area displaying the received plurality of similar medical images and a second display area displaying disease names has been displayed on the display is a selection of a disease name displayed in the second display area. That is, it can be presumed that a radiologist who has viewed the target medical image might have come up with a plurality of possible disease names for the target medical image. It can also be presumed that the radiologist might wish to check every differential item for the plurality of disease names thought of by the radiologist. In this case, similar medical images are less likely to need to be displayed on the display screen.

According to this aspect, in a case where the page of the electronic medical book which contains the differential items corresponding to the selected disease name is to be displayed on the display screen, the similar medical images displayed in the first display area are removed and the page of the electronic medical book is displayed in an entire area of the first display area. This can result in effective presentation of information desired by a radiologist, and can lead to effective use of a display screen with a limited display area.

In addition, in the aspect described above, for example, the page of the electronic medical book which contains the differential items corresponding to the selected disease name and a page of the electronic medical book which contains a medical image corresponding to the selected disease name may be arranged side by side in the first display area.

According to this aspect, a page of an electronic medical book is displayed in the entire first display area. Thus, a plurality of pages of an electronic medical book can be displayed in the first display area. According to this aspect, the page of the electronic medical book which contains the differential items corresponding to the selected disease name and a page of the electronic medical book which contains a medical image corresponding to the selected disease name are displayed side by side in the first display area. This can result in effective presentation of information useful for a radiologist to diagnose.

In addition, in the aspect described above, for example, the medical image database may have registered therein medical images contained in a plurality of electronic medical books, the additional information of each of the plurality of similar medical images may further include medical book identification information that identifies the electronic medical book which contains the similar medical image, and in response to detection of a selection of an electronic medical book from among the plurality of electronic medical books, a similar medical image contained in the selected electronic medical book may be displayed in the first display area.

In general, there are a variety of kinds of electronic medical books, and electronic medical books to which radiologists wish to refer differ. For example, electronic medical books mainly include electronic medical books used for educational purposes and electronic medical books used for diagnostic purposes. The electronic medical books used for educational purposes describe in detail differential items that are information necessary for determining a disease name. In contrast, the electronic medical books used for diagnostic purposes contain a large number of diverse medical images corresponding to specific disease names. Thus, there is a need for a radiologist to select either electronic medical book to efficiently obtain information necessary for diagnosis.

According to this aspect, upon detection of the selection of one of a plurality of electronic medical books, a similar medical image corresponding to the selected electronic medical book is displayed in the first display area. This enables efficient presentation of information required by the radiologist.

In addition, in the aspect described above, for example, cover images each representing a cover of one of the plurality of electronic medical books may be displayed on the display screen, and the received plurality of similar medical images may be displayed in the first display area so that electronic medical books containing the received plurality of similar medical images are distinguishable from one another.

According to this aspect, cover images each representing a cover of one of a plurality of electronic medical books are displayed on the display screen. In addition, the received plurality of similar medical images are displayed in the first display area so that electronic medical books containing the received plurality of similar medical images are distinguishable from one another. This enables the user to more easily select the medical book to which they wish to refer.

In addition, in the aspect described above, for example, in a case where the page of the electronic medical book which contains the selected similar medical image is to be displayed on the display screen, the selected similar medical image contained on the page of the electronic medical book may be displayed in a highlighted manner.

In general, a page of an electronic medical book often contains a plurality of medical images. Thus, even if a page of an electronic medical book is displayed on the display screen, it may be difficult for a radiologist to immediately determine which medical image matches the selected similar medical image.

According to this aspect, the selected similar medical image is displayed in a highlighted manner. This can save time and labor involved in searching for the selected similar medical image from among a plurality of medical images contained on a page of an electronic medical book. As a result, it is possible to make the radiologist concentrate on diagnosing, leading to an improvement in the accuracy of diagnosis and treatment.

In addition, in the aspect described above, for example, in a case where the page of the electronic medical book which contains the selected similar medical image is to be displayed on the display screen, the selected similar medical image contained on the page of the electronic medical book may be displayed at a predetermined position on the display screen.

In general, a page of an electronic medical book often contains a plurality of medical images. Thus, even if a page of an electronic medical book is displayed on the display screen, it may be difficult for a radiologist to immediately determine which medical image matches the selected similar medical image.

According to this aspect, the selected similar medical image is displayed at a predetermined position on the display screen. This can save time and labor involved in searching for the selected similar medical image from among a plurality of medical images contained on a page of an electronic medical book. As a result, it is possible to make the radiologist concentrate on diagnosing, leading to an improvement in the accuracy of diagnosis and treatment.

In addition, in the aspect described above, for example, the method may further include:

causing the computer of the information terminal to detect designation information indicating a region of interest in the target medical image;

causing the computer of the information terminal to transmit information indicating a feature value of the region of interest to the case search system; and causing the computer of the information terminal to receive a similar medical image having the predetermined similarity to the feature value of the region of interest from the case search system.

In addition, in the aspect described above, for example, the method may further include:

causing the computer of the information terminal to detect designation information indicating a region of interest in the target medical image;

causing the computer of the information terminal to transmit the target medical image and the designation information to the case search system; and causing the computer of the information terminal to receive, from the case search system, a similar medical image having the predetermined similarity to a feature value of the region of interest, which is obtained from the target medical image and the designation information.

In addition, in the aspect described above, for example, the target medical image may be a medical image of a lung, each of the plurality of similar medical images may be a medical image of a lung and has a corresponding region of interest indicating a lesion in the similar medical image, the display screen may include first distribution information for selection of a similar medical image in which the corresponding region of interest belongs to a first range indicating that a size of the corresponding region of interest is wide relative to a lung area, second distribution information for selection of a similar medical image in which the corresponding region of interest belongs to a second range lower than the first range, the second range indicating that a size of the corresponding region of interest is a portion of the lung area, and third distribution information for selection of a similar medical image in which the corresponding region of interest includes a pleura, and in response to detection of a selection of distribution information from among the first distribution information, the second distribution information, and the third distribution information, a similar medical image corresponding to the selected distribution information may be selected and displayed in the first display area.

According to this aspect, it is possible to further classify a plurality of similar medical images displayed in the first display area according to the distribution pattern of the corresponding region of interest. This enables efficient selection of, for example, a similar medical image for which the pattern of lesion distribution is similar to that for the target medical image from among a large number of displayed similar medical images.

In addition, in the aspect described above, for example, the first display area may include a plurality of individual areas, each displaying one of the received plurality of similar medical images, in response to detection of a selection of the first distribution information, a similar medical image corresponding to the first distribution information may be displayed at an initial display size in the corresponding one of the plurality of individual areas, in response to detection of a selection of the second distribution information, a similar medical image corresponding to the second distribution information may be enlarged and displayed in the corresponding one of the plurality of individual areas so as to be centered on the corresponding region of interest in the similar medical image corresponding to the second distribution information, and in response to detection of a selection of the third distribution information, a similar medical image corresponding to the third distribution information may be enlarged and displayed in the corresponding one of the plurality of individual areas so as to be centered on the corresponding region of interest in the similar medical image corresponding to the third distribution information, in such a manner that the corresponding region of interest includes the pleura.

According to this aspect, when similar medical images are classified according to the distribution pattern of the corresponding region of interest, the similar medical images are displayed in accordance with the distribution pattern in addition to the similar medical images being classified. This enables a radiologist to classify the similar medical images according to the distribution pattern of the corresponding region of interest without performing further operations such as enlarging the similar medical images in accordance with the distribution pattern or centering the corresponding region of interest. Accordingly, a complicated process of repeatedly performing similar operations on each of a large number of classified similar medical images even after classification according to the distribution pattern of the corresponding region of interest has been completed can be significantly reduced. This results in a significant reduction in the risk of radiologist's thoughts or radiologist's concentration on making a decision about diagnosis and treatment being interrupted by such a complicated process, helping the radiologist maintain their thoughts or concentration on making their own decision about diagnosis and treatment. The accuracy of the decision about diagnosis and treatment can thus be improved.

In addition, in the aspect described above, for example, the first distribution information may be information indicating a distribution that belongs to a category of bilateral, multiple, diffuse, or hematogenous, the second distribution information may be information indicating a distribution that belongs to a category of segmental or bronchial, and the third distribution information may be information indicating a distribution that belongs to a category of subpleural.

According to this aspect, for a distribution that belongs to the category of bilateral, multiple, diffuse, or hematogenous, similar medical images are displayed at an initial display size. For a distribution that belongs to the category of segmental or bronchial, similar medical images are enlarged and displayed. For a distribution that belongs to the category of subpleural, similar medical images are enlarged and displayed in such a manner that the pleura is included.

In the case of a distribution that belongs to the category of bilateral, multiple, diffuse, or hematogenous, a lesion may occupy the entire lung or a lesion may occupy a large area of the lung. Thus, there is a need, based on the medical knowledge, that a similar medical image be displayed at an initial display size, or without any enlargement of the similar medical. In the case of a distribution that belongs to the category of segmental or bronchial, in contrast, the above possibility is less likely to occur. Thus, selecting a distribution that belongs to the category of segmental or bronchial to resulting in the enlargement and display of similar medical images can remove the step of enlarging and displaying similar medical images, preventing the radiologist's concentration from being interrupted. In the case of a distribution that belongs to the category of subpleural, the positional relationship between the pleura and the lesion is an important index for diagnosis. Thus, there is a need, based on the medical knowledge, that a similar medical image be enlarged and displayed in such a manner that the pleura is included.

A control method according to another aspect of the present disclosure includes obtaining position information indicating a position selected on a display by a user for the first time after an image which includes a plurality of disease names including a first disease name and a plurality of thumbnails including a first thumbnail has been displayed on the display, the plurality of disease names being displayed in a disease name list display area in the image, the plurality of thumbnails corresponding to the plurality of disease names, the plurality of thumbnails corresponding to a plurality of similar medical images related to a target medical image that is a medical image to be interpreted, the plurality of similar medical images including a first similar medical image corresponding to the first thumbnail; instructing, in a case where the obtained position information indicates that the selected position is a position at which the first disease name is displayed in the disease name list display area, the display to display part or all of a first page including differential items for a disease identified by the first disease name; and instructing, in a case where the obtained position information indicates that the selected position is a position at which the first thumbnail is displayed, the display to display part or all of a second page including the first similar medical image. In a case where the first disease name corresponds to the first thumbnail, identical electronic content includes the first page and the second page.

EMBODIMENTS

An embodiment of the present disclosure will now be described hereinafter with reference to the drawings. In the drawings, the same or substantially the same components are represented by the same numerals.

FIG. 1 is an overall configuration diagram of a hospital information system in which an information terminal according to this embodiment is used. As illustrated in FIG. 1, the hospital information system includes an information terminal 100, a medical information management system 200, and a case search system 300.

The information terminal 100, the medical information management system 200, and the case search system 300 are connected to one another via a network 400 so as to be capable of communicating with one another.

The medical information management system 200 and the case search system 300 may not necessarily be located in the hospital, and may be implemented by software operating on a data center, a private cloud server, a public cloud server, or the like located outside the hospital. In a case where the medical information management system 200 and the case search system 300 are located in the hospital, the network 400 may be a local area network (LAN). Examples of the LAN include wired LANs specified by the Institute of Electrical and Electronics Engineers (IEEE) 802.3 series standards, wireless LANs specified by the IEEE 802.11 series standards, and networks including both such wired and wireless LANs. In a case where the medical information management system 200 and the case search system 300 are implemented by using a server located outside the hospital, the network 400 may be the Internet.

The information terminal 100 may be a personal computer or an information terminal such as a tablet terminal. The medical information management system 200 may be a picture archiving and communication system (PACS), an electronic medical record system, or the like.

Figure 2:
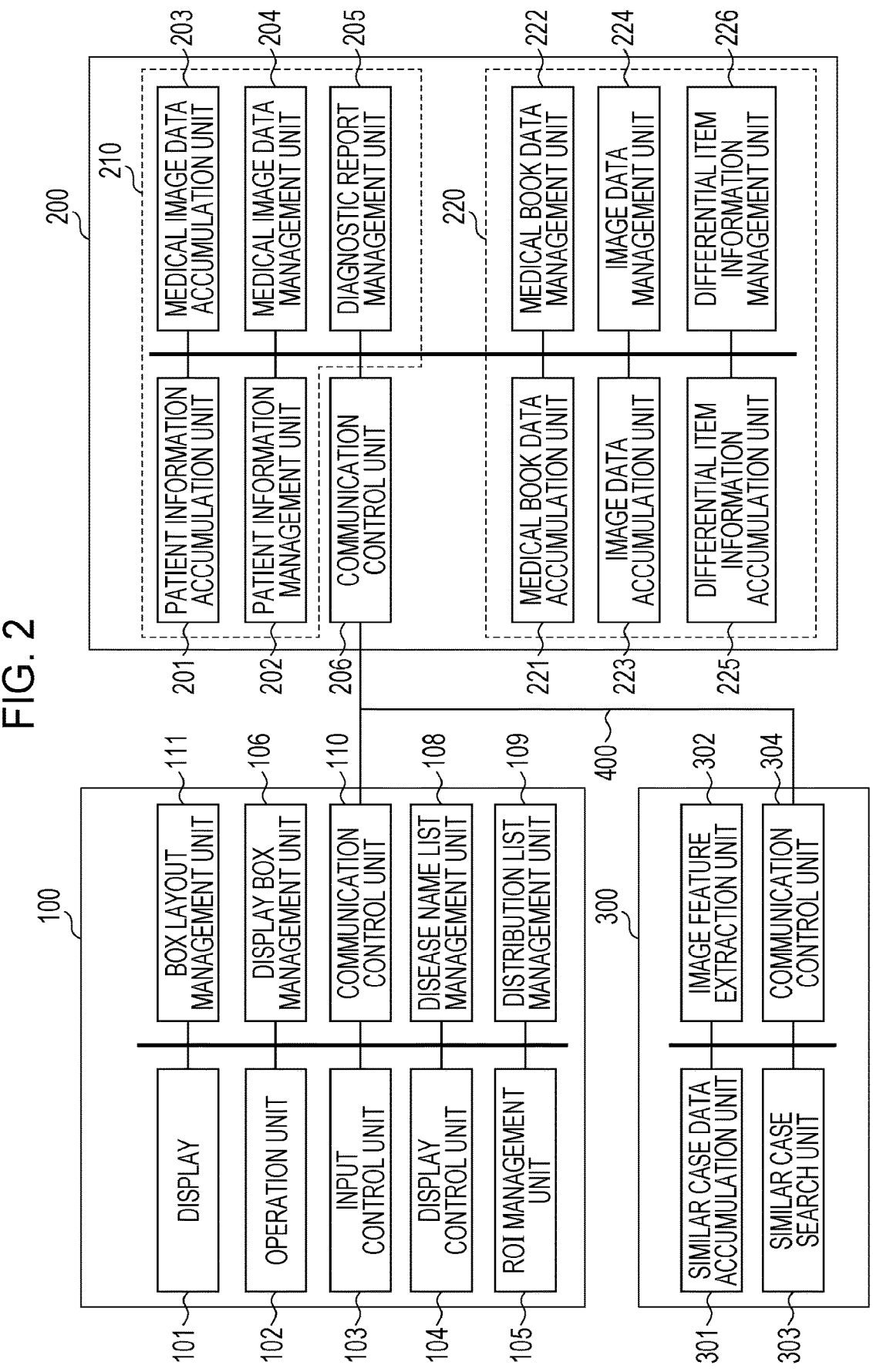
FIG. 2 is a block diagram illustrating the configuration of the information terminal, a medical information management system, and a case search system.

FIG. 2 is a block diagram illustrating the configuration of the information terminal 100, the medical information management system 200, and the case search system 300. As illustrated in FIG. 2, the information terminal 100 includes a display 101, an operation unit 102, an input control unit 103, a display control unit 104, a region of interest (ROI) management unit 105, a display box management unit 106, a disease name list management unit 108, a distribution list management unit 109, a communication control unit 110, and a box layout management unit 111.

The display 101 may be formed of, for example, a liquid crystal monitor. The display 101 displays a medical chart image and a medical image to be diagnosed, and also displays a report input image or the like in which diagnostic results are entered. While at least one display 101 is required, two to three displays 101 are typically used for image-based diagnosis. In this embodiment, two displays 101 are used. One of the displays 101 is referred to as a display 101a, and the other display 101 is referred to as a display 101b (see FIG. 3).

Figure 3:
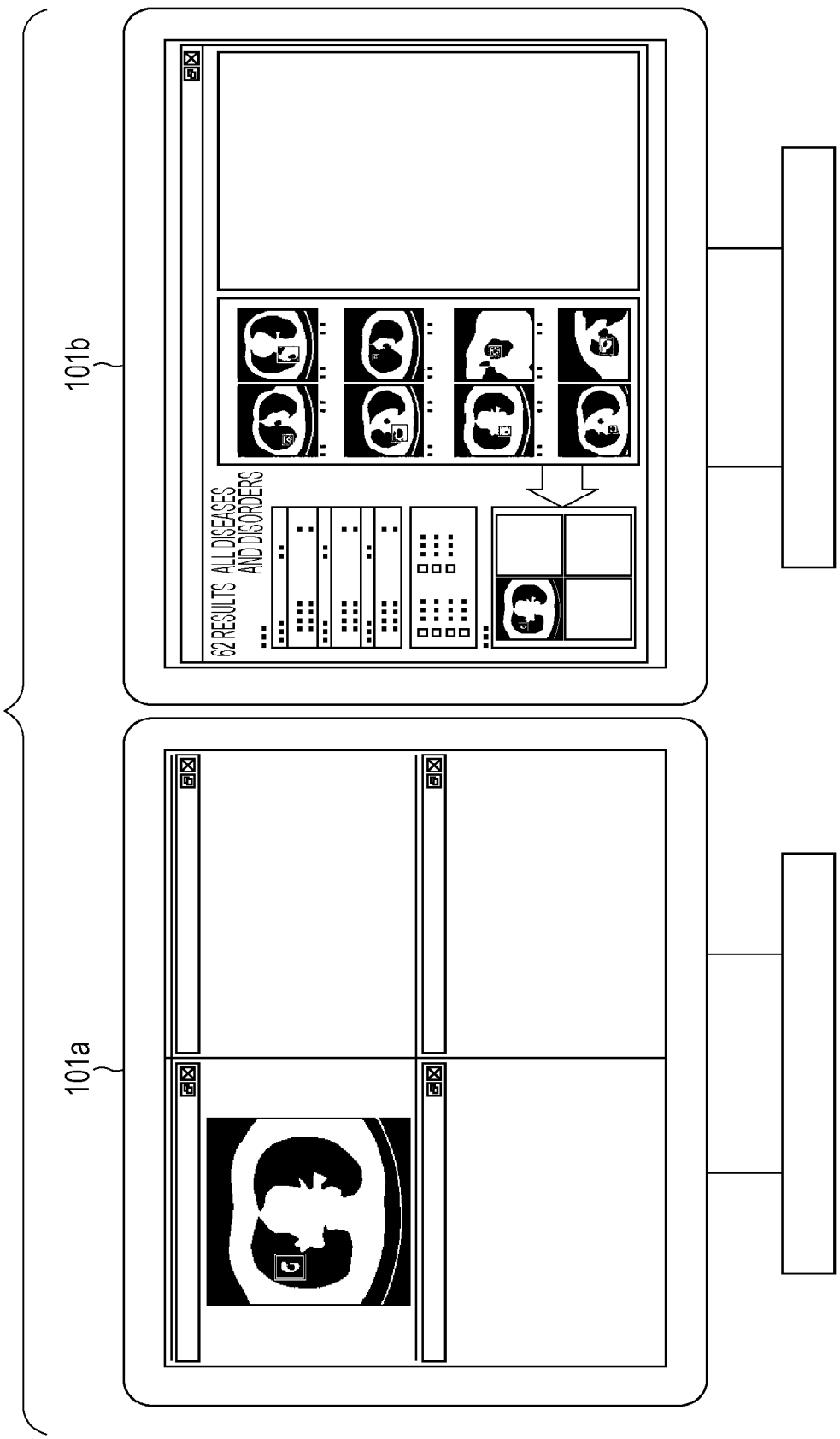
FIG. 3 illustrates external views of two displays.

FIG. 3 illustrates external views of the two displays 101a and 101b. In FIG. 3, four medical image viewers arranged in two rows and two columns are displayed on the display 101a, and a screen for the case search system 300 is displayed on the display 101b. In a case where a single display 101 is used, the two display screens are displayed in separate areas on the display screen of the single display 101.

Referring back to FIG. 2, the operation unit 102 includes, for example, a keyboard and a mouse, and accepts a variety of operations input by a user on the information terminal 100. For example, the operation unit 102 accepts operations such as an operation performed by the user on a medical image and a medical chart image displayed on the display 101, and an operation for entering diagnostic results in the report input screen.

Upon detection of an operation performed by the user on the operation unit 102, the input control unit 103 interprets the operation, and notifies the other components of the content of the operation. For example, the input control unit 103 detects the position of the mouse pointer on the display 101 by using coordinate data output from the mouse serving as the operation unit 102, and causes the mouse pointer to be displayed on the display 101. If a graphical user interface (GUI) component (e.g., a GUI button) generated by the display control unit 104 is being displayed at the display position of the mouse pointer when a click of the mouse is detected, the input control unit 103 determines that the user has selected the GUI component, and notifies the other components that the GUI component has been selected by the user.

The display control unit 104 generates a GUI of the information terminal 100, and displays the GUI on the display 101.

When performing a similar case search, the ROI management unit 105 generates region-of-interest information indicating a region of interest (ROI) set on a search query image described below, and stores the region-of-interest information in a memory to manage the region-of-interest information.

The display box management unit 106 stores display box management information 4410 described below (FIG. 40) in the memory to manage the display box management information 4410.

The disease name list management unit 108 generates a disease name list (FIG. 42) that is a list of the names of diseases of similar cases displayed in a case display area 710 (FIG. 9), and stores the disease name list in the memory to manage the disease name list.

The distribution list management unit 109 generates a distribution list (FIG. 47) that is a list of patterns of lesion distribution in the similar cases displayed in the case display area 710, and stores the distribution list in the memory to manage the distribution list.

The communication control unit 110 includes, for example, a communication device that connects the information terminal 100 to the network 400, and controls communication between the information terminal 100 and the medical information management system 200 and communication between the information terminal 100 and the case search system 300. Further, the communication control unit 110 accepts, from other blocks, requests for transmitting various kinds of data, and transmits data to the medical information management system 200 or the case search system 300. In addition, the communication control unit 110 receives data transmitted from the medical information management system 200 or the case search system 300, and passes the data to the corresponding block.

The box layout management unit 111 generates layout management information, and stores the layout management information in the memory to manage the layout management information.

As illustrated in FIG. 2, the medical information management system 200 includes a hospital data section 210, a medical book data section 220, and a communication control unit 206. The hospital data section 210 includes a patient information accumulation unit 201, a patient information management unit 202, a medical image data accumulation unit 203, a medical image data management unit 204, and a diagnostic report management unit 205.

The patient information accumulation unit 201 accumulates patient information 1000 (FIG. 28) in which personal information on each patient, such as gender and age, clinical information such as the past medical history that the patient has, and test information on medical tests that the patient has undergone, such as a blood test, are registered.

The patient information management unit 202 performs processes, such as a process for registering data input by a user in the patient information 1000 (FIG. 28) accumulated in the patient information accumulation unit 201 to update the patient information 1000 and a process for outputting the patient information 1000 to the display control unit 104, to manage the patient information 1000.

The medical image data accumulation unit 203 accumulates medical image data representing test images of the patient. The medical image data management unit 204 accumulates the medical image data in the medical image data accumulation unit 203 to manage the medical image data.

The diagnostic report management unit 205 manages a diagnostic report 3000 (FIG. 31) which shows the diagnostic results provided by the radiologist for each test given to the patient.

The communication control unit 206 includes, for example, a communication device that connects the medical information management system 200 to the network 400. The communication control unit 206 accepts, from other blocks, requests for transmitting various kinds of data, and transmits data to the information terminal 100 or the case search system 300. In addition, the communication control unit 206 receives data transmitted from the information terminal 100 or the case search system 300, and passes the data to the corresponding block.

As illustrated in FIG. 2, the medical book data section 220 includes a medical book data accumulation unit 221, a medical book data management unit 222, an image data accumulation unit 223, an image data management unit 224, a differential item information accumulation unit 225, and a differential item information management unit 226.

The medical book data accumulation unit 221 accumulates medical book data 410 (FIG. 4). The medical book data 410 is data representing an electronic medical book. The medical book data management unit 222 manages the medical book data 410 accumulated in the medical book data accumulation unit 221. The medical book data management unit 222 performs processes, such as a process for updating the medical book data 410 to new one and a process for outputting every piece of information included in the medical book data 410 to the display control unit 104.

FIG. 4 is a diagram illustrating the data configuration of the medical book data 410 accumulated in the medical book data accumulation unit 221. As illustrated in FIG. 4, the medical book data 410 includes a medical book ID 411, a path to a medical book 412, a book title 413, and a path to a cover image 414. The medical book ID 411 is an identifier specific to the medical book. The path to the medical book 412 indicates a path to a storage location of data scanned from the medical book (an electronic medical book created as electronic content). The book title 413 indicates the title of the medical book. The path to the cover image 414 indicates a path to a location where scanned data of a thumbnail image of the cover of the medical book is stored.

Referring back to FIG. 2, the image data accumulation unit 223 accumulates medical book image data 420 (FIG. 5). The medical book image data 420 is data representing a medical image contained in an electronic medical book.

The image data management unit 224 manages the medical book image data 420 accumulated in the image data accumulation unit 223. The image data management unit 224 performs processes, such as a process for updating the medical book image data 420 to new one and a process for outputting every piece of information included in the medical book image data 420 to the display control unit 104.

FIG. 5 is a diagram illustrating the data configuration of the medical book image data 420 accumulated in the image data accumulation unit 223. As illustrated in FIG. 5, the medical book image data 420 includes a medical book ID 421, a path 422, an image ID 423, a definitely diagnosed disease name 424, a page number 425, and a line number 426. The medical book ID 421 is an identifier specific to a medical book. The path 422 indicates a path to a storage location of image data of an image identified by the image ID 423. The image ID 423 is an identifier specific to a medical image contained in the medical book. The definitely diagnosed disease name 424 indicates the name of the disease definitely diagnosed for the corresponding medical image. The page number 425 indicates the number of the page of the medical book which contains the corresponding medical image. The line number 426 indicates the number of the line in which the corresponding medical image first appears on the page of the medical book. The medical book image data 420 is an example of additional information of a similar medical image, and the medical book ID 421 is an example of medical book identification information.

Figures 6, 7:
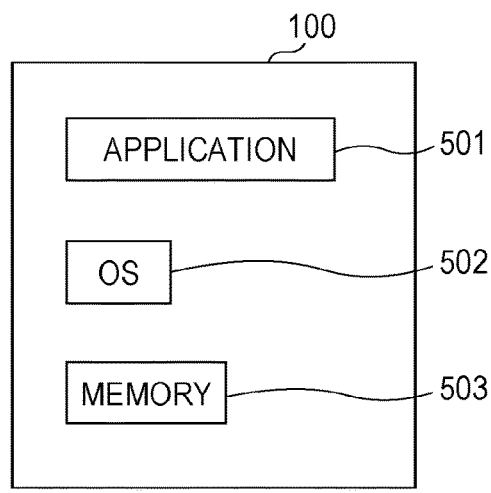
FIG. 6 is a diagram illustrating the data configuration of differential item information.
FIG. 7 is a diagram illustrating an example configuration of an implementation of the information terminal.

Referring back to FIG. 2, the differential item information accumulation unit 225 accumulates differential item information 430 (FIG. 6). The differential item information 430 includes differential items contained in an electronic medical book. The differential item information management unit 226 manages the differential item information 430 accumulated in the differential item information accumulation unit 225. The differential item information management unit 226 performs processes, such as a process for updating the differential item information 430 to new one and a process for outputting every piece of information included in the differential item information 430 to the display control unit 104.

FIG. 6 is a diagram illustrating the data configuration of the differential item information 430 accumulated in the differential item information accumulation unit 225. As illustrated in FIG. 6, the differential item information 430 includes a medical book ID 431, a disease name 432, differential items 433, a page number 434, and a line number 435. The medical book ID 431 is an identifier specific to a medical book. The disease name 432 indicates the name of a disease related to information included in the differential item information 430.

The differential items 433 indicate items necessary to define the diagnosis of the disease designated by the disease name 432. After narrowing down the names of possible diseases that the patient for whom image interpretation is to be performed might have to some extent, the radiologist checks each of the differential items 433 against the medical images of the patient, follow-up information about the patient, and the like to finally define the name of the disease of the patient. The page number 434 indicates the number of the page of the medical book which contains the differential items 433. The line number 435 indicates the number of the line in which the differential items 433 first appear on the page of the medical book. The differential item information 430 is an example of additional information of a disease name.

Referring back to FIG. 2, the case search system 300 includes a similar case data accumulation unit 301, an image feature extraction unit 302, a similar case search unit 303, and a communication control unit 304.

The similar case data accumulation unit 301 accumulates, in advance, similar case data 4000 (FIG. 32) in which image features extracted from a large number of similar cases selected as target data for a similar case search from among the similar cases managed in the medical information management system 200 (in this embodiment, for example, the medical book data section 220 in the medical information management system 200), generated thumbnail images, and the like are registered.

The image feature extraction unit 302 extracts an image feature in region-of-interest information on the search query image transmitted from the communication control unit 110 of the information terminal 100. The region-of-interest information is an example of designation information indicating a region of interest.

The similar case search unit 303 compares the image feature extracted by the image feature extraction unit 302 with each of image features in one or more similar cases accumulated in the similar case data accumulation unit 301 to generate similar case search results.

The communication control unit 304 is formed of, for example, a communication device that connects the case search system 300 to the network 400. The communication control unit 304 accepts, from other blocks, requests for transmitting various kinds of data, and transmits data to the information terminal 100 or the medical information management system 200. In addition, the communication control unit 304 receives data transmitted from the information terminal 100 or the medical information management system 200, and passes the data to the corresponding block.

FIG. 7 is a diagram illustrating an example configuration of an implementation of the information terminal 100. As illustrated in FIG. 7, the information terminal 100 includes an application 501, an operating system (OS) 502, a memory 503, and other hardware (not illustrated).

The application 501 is application software for causing a personal computer or a tablet terminal to function as the information terminal 100, and is executed by a processor of the information terminal 100. The information terminal 100 may implement the application 501 by reading the application 501 from a computer-readable recording medium, or may implement the application 501 by downloading the application 501 from a network.

The application 501 includes a medical information management application and a similar case search application. The medical information management application is an application for allowing the information terminal 100 to operate in coordination with the medical information management system 200, and the similar case search application is an application for allowing the information terminal 100 to operate in coordination with the case search system 300. The medical information management application and the similar case search application transmit and receive data to and from each other so that services provided by the medical information management system 200 and the case search system 300 are integrated in the information terminal 100.

The OS 502 is basic software of the information terminal 100, and is executed by a processor of the information terminal 100. The memory 503 includes storage devices such as a random access memory (RAM) and a read-only memory (ROM), which are included in the information terminal 100, and stores pieces of data included in the application 501.

The processor of the information terminal 100 executes the application 501 to implement the functions of the input control unit 103, the display control unit 104, the ROI management unit 105, the display box management unit 106, the disease name list management unit 108, the distribution list management unit 109, the communication control unit 110, and the box layout management unit 111, which are illustrated in FIG. 2.

In this embodiment, the information terminal 100 may be implemented solely by the application 501, or may be implemented by the application 501 and the OS 502. Alternatively, the information terminal 100 may be implemented by the application 501, the OS 502, and the memory 503, or may be implemented by the application 501, the OS 502, the memory 503, and any other hardware (not illustrated). The information terminal 100 according to this embodiment is achievable through any of the implementations described above.

Figure 8:
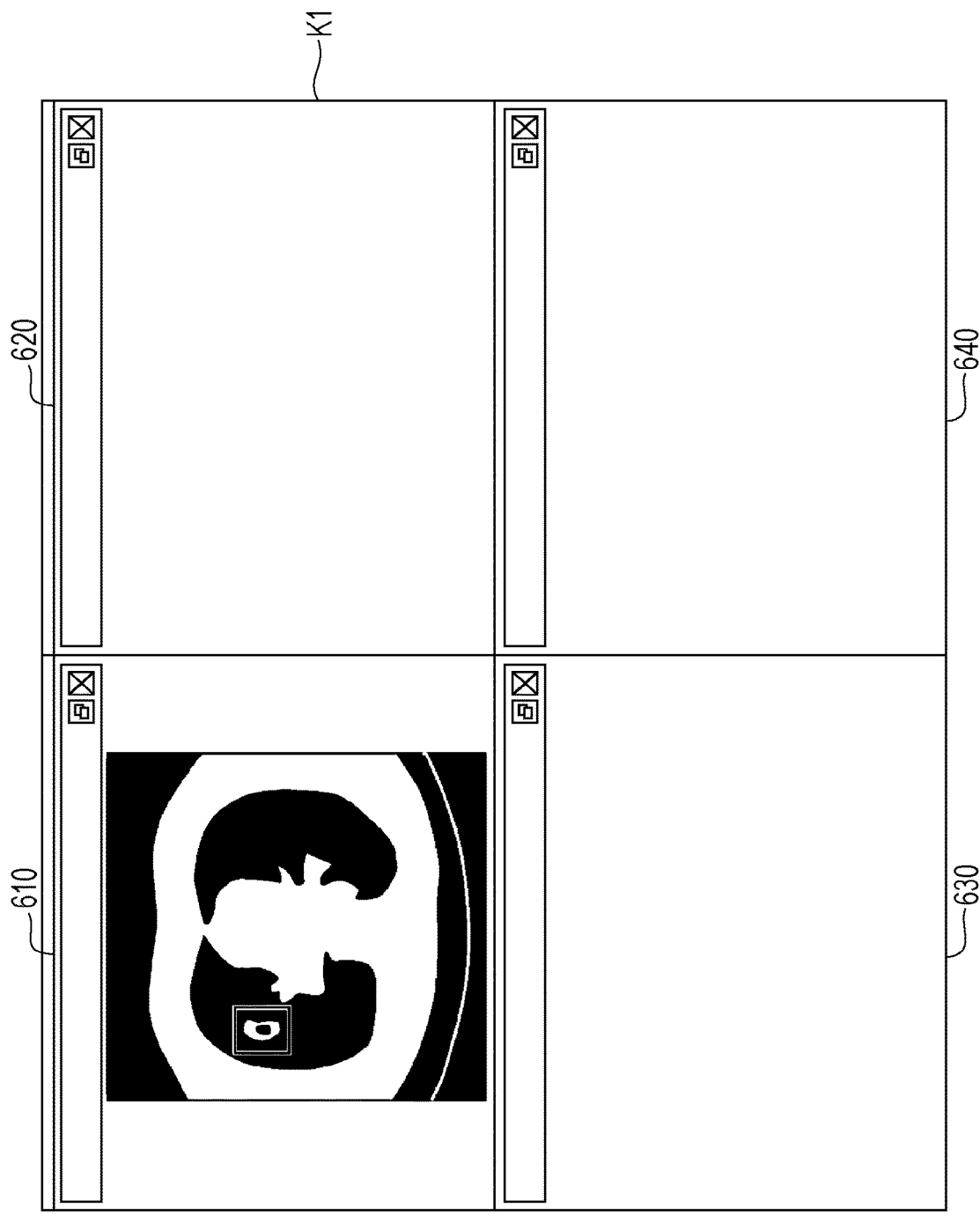
FIG. 8 is a diagram illustrating an example of a basic screen displayed on a display immediately after a similar case search application has been started on the information terminal.

FIG. 8 is a diagram illustrating an example of a basic screen K1 displayed on the display 101a immediately after the similar case search application has been started on the information terminal 100. The basic screen K1 illustrated in FIG. 8 includes four medical image viewers 610 to 640. Typical medical images are recorded in Digital Imaging and Communication in Medicine (DICOM) format, and the medical image viewers 610 to 640 are DICOM-compatible viewers. The medical images as used in this embodiment are chest CT images constituted by a large number of tomographic images (hereinafter referred to as "slice images") in DICOM format. However, this is merely an example, and CT images of any other body part (e.g., the head, abdomen, legs, or arms) may be used.

Each of the chest CT images displayed in the medical image viewers 610 to 640 is switched from one slice image to another through an operation with the mouse or keyboard. The slice images constituting the chest CT images are arranged in order from, for example, the neck toward the abdomen.

For example, when the input control unit 103 detects a rotation of the mouse wheel while the mouse pointer is on the medical image viewer 610, the display control unit 104 switches the slice image currently displayed in the medical image viewer 610 in accordance with the amount of rotation which is detected. For example, when the mouse wheel is rotated rearward (or toward the user of the mouse) by an amount corresponding to one click while the mouse is on the medical image viewer 610, the display control unit 104 switches the currently displayed slice image to the slice image corresponding to the next slice position. For example, when the mouse wheel is rotated forward (or away from the user of the mouse) by an amount corresponding to one click while the mouse is on the medical image viewer 610, the display control unit 104 switches the currently displayed slice image to the slice image corresponding to the preceding slice position. Accordingly, the user, such as a radiologist, retrieves the desired slice images while rotating the mouse wheel forward or rearward to appropriately switch between slice images to be displayed in the medical image viewer 610.

In place of chest CT images, magnetic resonance imaging (MRI) images or simple X-ray images may be used as medical images. Furthermore, four medical image viewers are used in the example illustrated in FIG. 8. This is merely an example, and a different number of medical image viewers, such as six or eight medical image viewers, may be used. As the number of medical image viewers used increases, the number of images to be simultaneously compared also increases whilst the area of each image that can be displayed decreases.

Accordingly, the number of medical image viewers may be made variable, as desired, in accordance with the display size of the display 101a. It is assumed here that the number of medical image viewers can be changed by the user or an administrator as desired.

Before the similar case search application is started, a slice image of a chest CT image of a given patient is displayed in the entire area of the display 101a. When the similar case search application is started in this situation by the user such as a person who undertakes image interpretation, the slice image being displayed in the entire area of the display 101a is displayed in the medical image viewer 610. That is, a search query image being displayed in the entire area of the display 101a when the user starts the similar case search application is initially displayed in the medical image viewer 610. The display control unit 104 may superimpose the region of interest (ROI) of the target to be subjected to a similar case search on the search query image for display. The search query image is an example of a target medical image that is a medical image to be interpreted.

In FIG. 8, no images are displayed in the medical image viewers 620 to 640. If there are a plurality of test images of a patient to be diagnosed and a plurality of test images have been displayed on the display 101a before the similar case search application is started, the display control unit 104 may directly display the plurality of test images in the medical image viewers 620 to 640.

Figure 9:
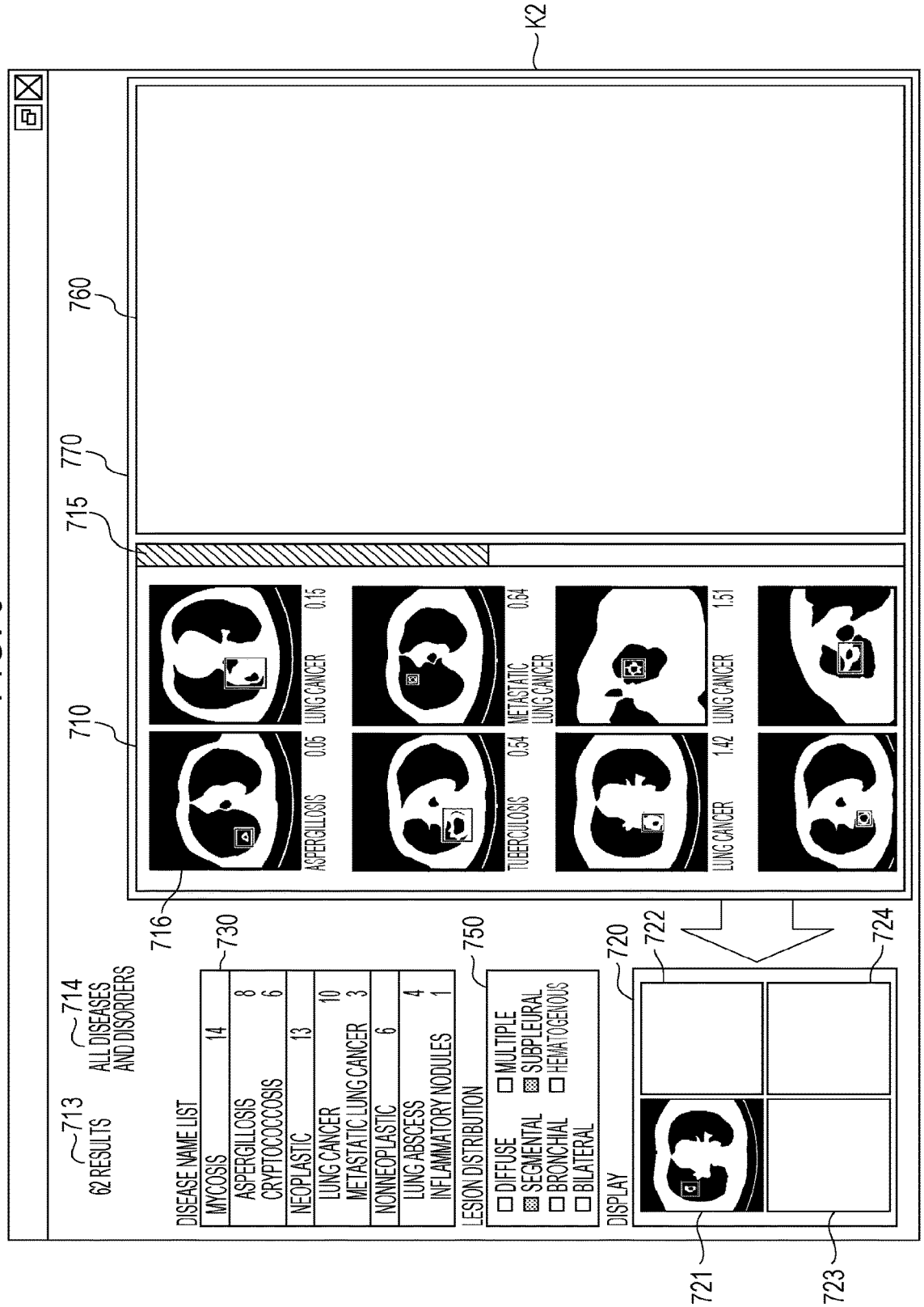
FIG. 9 is a diagram illustrating an example of a basic screen displayed on a display immediately after the similar case search application has been started on the information terminal.

FIG. 9 is a diagram illustrating an example of a basic screen K2 displayed on the display 101b immediately after the similar case search application has been started on the information terminal 100. The basic screen K2 illustrated in FIG. 9 includes a similar case data display area 770, a layout area 720, a disease name list display area 730, and a distribution list display area 750. The similar case data display area 770 includes a case display area 710 located in the left portion thereof, and a medical book display area 760 located in the right portion thereof.

The basic screen K2 is an example of a display screen. The similar case data display area 770 is an example of a first display area, and the disease name list display area 730 is an example of a second display area.

The case display area 710 of the similar case data display area 770 is an area where thumbnail images of similar cases that are similar to the search query image are displayed in order of similarity. A thumbnail image of a similar case is an example of a similar medical image.

Since the case display area 710 shows a large number of similar cases, further processing for resolution conversion or pixel-value conversion will take time. To avoid this inconvenience, the thumbnail images are created in advance from the original slice images, and are stored in the case search system 300.

A further description will now be given of resolution conversion and pixel-value conversion. Original slice images contained in a medical book (in this embodiment, accumulated in the image data accumulation unit 223, for example) typically have a resolution of 512 pixels by 512 pixels, whereas thumbnail images have a lower resolution. Thus, resolution conversion is needed. Accordingly, each of the thumbnail images is generated through the resolution reduction and grayscale conversion of the corresponding one of the original slice images.

For example, a grayscale conversion process is performed in the following way. Slice images obtained by CT imaging have pixel values (CT values) of 2000 grayscale values from −1000 to +1000 (expressed in Hounsfield units (HU)), and will not be directly displayed on a standard 8-bit grayscale display. Even if such slice images can be displayed, it is difficult for a person to distinguish the areas of pulmonary emphysema (with a CT value of −1000 HU), normal lung tissue (with a CT value of approximately −900 HU), the area of ground-glass opacity (with a CT value of −800 HU), soft tissue (with a CT value of −100 to −50 HU), water (with a CT value of 0 HU), and bone (with a CT value of 1000 HU), in the range of the 2000 grayscale values, from one another with the naked eye.

Thus, slice images are typically reconstructed with 8-bit pixel values for display on a display, where a window level and a window width are set for each pixel value. The window level represents the CT value of the center of the window, and the window width represents the difference between the upper limit and lower limit of a range centered about the center of the window.

For example, in a case where a DICOM image is reconstructed with the pulmonary condition, the window level is set to −550 to −800 and the window width is set to 1000 to 1600. Thus, a thumbnail image is also generated through the processes described above by reducing the pixel values of the original slice image to 8-bit pixel values.

The thumbnail images displayed in the case display area 710 are thumbnail images representing similar cases for which the distance from the feature vector of the case to be diagnosed is less than or equal to a predetermined threshold value. Here, the distance is a Euclidean distance, by way of example. Any other distance measure, such as city block, may be used as the distance. As the distance between the two images to be compared decreases, the similarity between them increases. The feature vectors are not obtained from the thumbnail images but are obtained from the original images, that is, the slice images.

Figure 10:
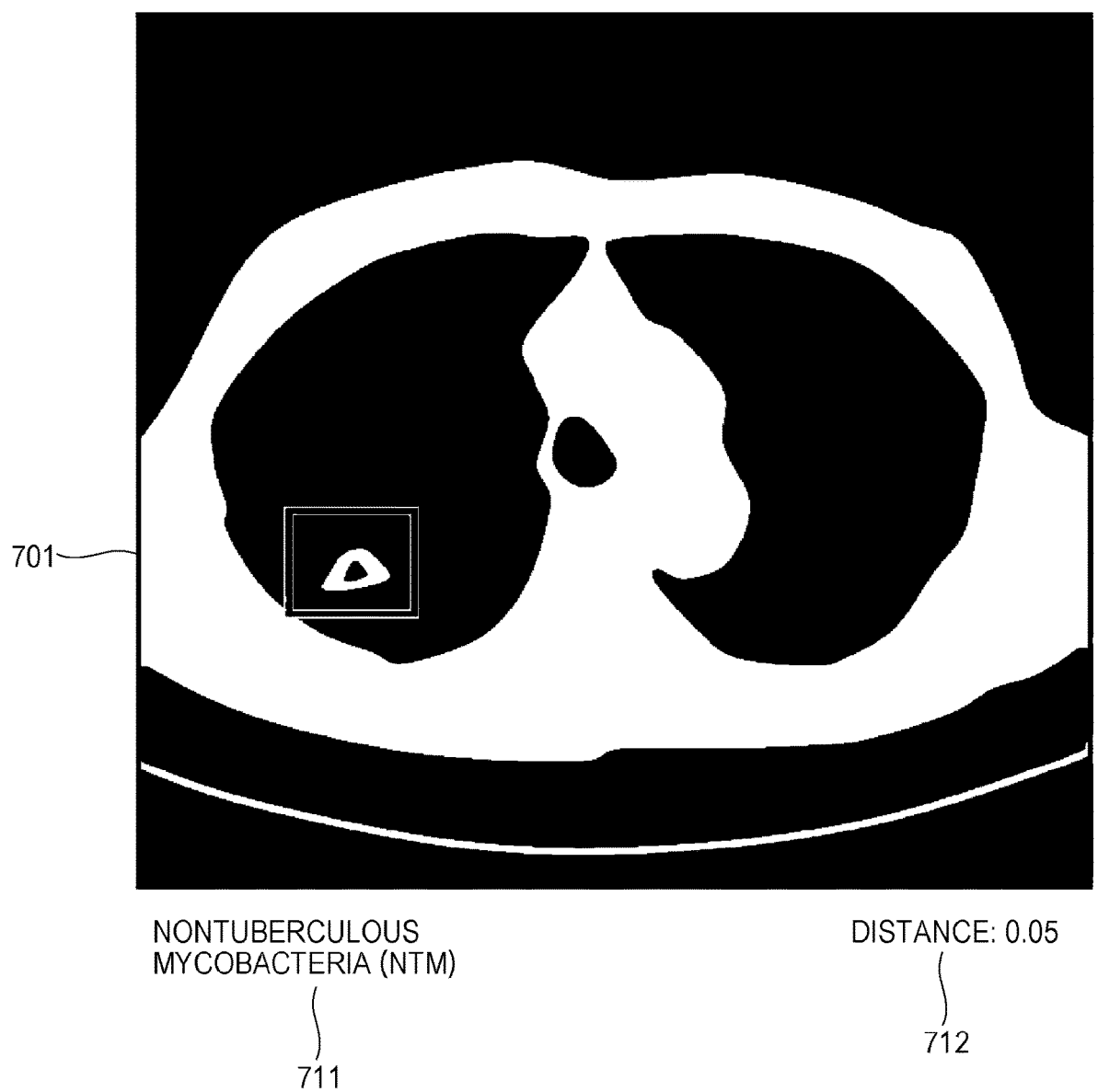
FIG. 10 is a diagram illustrating an extracted display area for one similar case displayed in a case display area.

FIG. 10 is a diagram illustrating a certain similar case display area 701 (an example of an individual area) extracted from among similar case display areas displayed in the case display area 710. A thumbnail image is displayed in the similar case display area 701, and a definitely diagnosed disease name display area 711 and a distance display area 712 are placed below the thumbnail image. The definitely diagnosed disease name display area 711 shows a definitely diagnosed disease name of the target similar case. The definitely diagnosed disease name refers to the name of a disease as which the target similar case has been definitely diagnosed. The distance display area 712 shows a distance between the feature vector for the slice image of the target similar case and the feature vector for the search query image. In the example illustrated in FIG. 10, the definitely diagnosed disease name display area 711 shows "nontuberculous mycobacteria (NTM)". Thus, the illustrated thumbnail image is a thumbnail image of a similar case definitely diagnosed as "nontuberculous mycobacteria (NTM)". The distance display area 712 shows "0.05", which indicates that the distance between the slice image of the similar case and the search query image is "0.05".

Referring back to FIG. 9, the basic screen K2 has a number-of-search-result display area 713 in the upper left portion thereof, for example. The number-of-search-result display area 713 shows the number of similar cases that are similar to the case to be diagnosed. The number of similar cases is obtained from the case search system 300 as a result of the search process.

If the number of similar cases is very large, it will be difficult to display all the similar cases in the case display area 710 at the same time. To address this difficulty, the case display area 710 has in the right portion thereof a scrollbar 715 that is vertically long, for example. The display control unit 104 vertically scrolls through thumbnail images displayed in the case display area 710 in accordance with the amount of movement of the scrollbar 715. This enables the user to display currently invisible similar cases in the case display area 710 so that the user can observe the similar cases.

The scrollbar 715 may be horizontally long. In this case, it is desirable that the display control unit 104 horizontally scroll through thumbnail images displayed in the case display area 710 in accordance with the amount of movement of the scrollbar 715. Alternatively, the display control unit 104 may be configured to, in response to the depression of any direction key on the keyboard while the mouse pointer is on the case display area 710, scroll through thumbnail images displayed in the case display area 710 in a direction corresponding to the key being pressed.

The information terminal 100 is configured to obtain, from the case search system 300, thumbnail images whose distances from the search query image are less than or equal to a predetermined threshold value. However, this is merely an example. For example, the information terminal 100 may constantly obtain a certain number of thumbnail images from the case search system 300 in order of decreasing similarity. Alternatively, the information terminal 100 may obtain thumbnail images from the case search system 300 so that the thumbnail images constantly include a certain number of thumbnail images of a certain definitely diagnosed disease name.

The thumbnail images may be displayed in the case display area 710 in such a manner that, for example, the thumbnail images are displayed from left to right in order of ascending distance such that the thumbnail image whose distance from the search query image is the shortest is displayed at the left end in the top row and, once the right end in the same row is reached, the next thumbnail image is displayed at the left end in the second row from the top. That is, the following display technique may be used: The thumbnail images are displayed in the case display area 710, from left to right, top to bottom, in order of increasing distance.

It is anticipated that any other display technique may be used in this embodiment. For example, the thumbnail images may be displayed from top to bottom in order of ascending distance such that the thumbnail image whose distance from the search query image is the shortest is displayed at the top in the first column from the left and, once the bottom in the same column is reached, the next thumbnail image is displayed at the top in the second column from the left. Alternatively, a configuration may be adopted in which the user can switch between the plurality of display techniques described above.

In the example described above, distance is used as similarity measure. Any index indicating the similarity between images, such as cosine similarity, may be used. In a case where cosine similarity is used, as the value approaches 1, the similarity between two images to be compared increases.

The similar cases to be displayed in the case display area 710 can be refined according to a disease name displayed in the disease name list display area 730 or according to a lesion distribution displayed in the distribution list display area 750, which will be described in detail below. A currently set condition under which the similar cases are refined is displayed in a display condition display area 714. The example illustrated in FIG. 9 shows the state immediately after a similar case search has been performed, and no refinement is performed. Thus, "all diseases and disorders" is displayed in the display condition display area 714.

The layout area 720 is located in, for example, the lower left portion of the basic screen K2 illustrated in FIG. 9. The layout area 720 is used to display, in a medical image viewer on the display 101a, an image that the user wishes to observe in more detail among the thumbnail images of the similar cases displayed in the case display area 710. As illustrated in FIG. 8, the four medical image viewers 610 to 640 are displayed on the display 101a so as to be arranged in two rows and two columns. Further, the layout area 720 has four display boxes 721 to 724 arranged in two rows and two columns. In the manner described above, the number and layout of the medical image viewers 610 to 640 displayed on the display 101a are consistent with the number and layout of the display boxes 721 to 724 in the layout area 720. In accordance with the display of the search query image in the medical image viewer 610 in the manner illustrated in FIG. 8, the thumbnail image of the search query image is initially displayed in the display box 721.

Each of the other display boxes 722 to 724 shows a thumbnail image of a similar case in accordance with an image displayed in the corresponding one of the medical image viewers 620 to 640. That is, when the input control unit 103 detects a drag-and-drop of one of the thumbnail images displayed in the case display area 710 onto one of the display boxes 722 to 724, the display control unit 104 causes the thumbnail image to be displayed in the corresponding display box, and also causes the slice image corresponding to the thumbnail image to be displayed in the medical image viewer corresponding to the display box. Accordingly, the medical image viewers 610 to 640 are associated with the display boxes 721 to 724 in a one-to-one correspondence. In the example illustrated in FIG. 9, the display boxes 722 to 724 are blank, and the medical image viewers 620 to 640 illustrated in FIG. 8 are also blank accordingly.

The user performs a drag-and-drop operation using the mouse to move the thumbnail image that the user wishes to observe in more detail from the case display area 710 to the layout area 720. For example, when the user moves a thumbnail image to the display box 722, the slice image corresponding to the thumbnail image is displayed in the medical image viewer 620 corresponding to the display box 722. Also, when the user moves a thumbnail image to the display box 723, the slice image corresponding to the thumbnail image is displayed in the medical image viewer 630 corresponding to the display box 723. That is, in response to the movement of a thumbnail image to any display box among the display boxes 722 to 724, a thumbnail image of a similar case is displayed adjacent to the thumbnail image of the search query image. This enables the user to compare the case to be diagnosed with the similar case at a thumbnail image level and to quickly judge the similarity between the two cases. Since thumbnail images have a smaller amount of information than slice images, the user is able to roughly estimate how much the case to be diagnosed and the similar case which are adjacent to each other in the layout area 720 are similar. This enables the user to efficiently narrow a large number of similar cases displayed in the case display area 710 down to a final set of candidates of similar cases to be compared with the case to be diagnosed in more detail at a slice image level.

The search query image and slice images of similar cases are also displayed on the display 101a in the same position and layout as those in the layout area 720. After the completion of narrowing down to a final set of candidates of similar cases in the layout area 720, the case to be diagnosed and similar cases obtained as the final set of candidates are displayed on the display 101a at a slice image level without input of any operation. This guides the user smoothly to the next operation step of detailed image interpretation of the case to be diagnosed and the similar cases obtained as the final set of candidates.

The disease name list display area 730 with the heading "disease name list" is located in the upper left portion of the basic screen K2 illustrated in FIG. 9. The disease name list display area 730 shows definitely diagnosed disease names of all the similar cases obtained as a result of the similar case search. The case to be diagnosed is assigned a definitely diagnosed disease name after the completion of a diagnosis, and is then accumulated in the case search system 300 as a similar case. Thus, each similar case is assigned a definitely diagnosed disease name obtained through a diagnosis beforehand.

FIG. 11 is an enlarged view of the disease name list display area 730. In FIG. 11, definitely diagnosed disease names are classified into major-category disease names (731, 734, 737, 741, and 744) and subcategory disease names (732, 733, 735, 736, 738, 739, 740, 742, 743, and 745) for display. In the example illustrated in FIG. 11, "mycosis" 731, "neoplastic" 734, "nonneoplastic" 737, "mycobacteriosis" 741, and "others" 744 are displayed as major-category disease names.

In the example illustrated in FIG. 11, furthermore, "aspergillosis" 732 and "cryptococcosis" 733 are displayed as subcategory disease names of the "mycosis" 731. Further, "lung cancer" 735 and "metastatic lung cancer" 736 are displayed as subcategory disease names of the "neoplastic" 734. Further, "lung abscess" 738, "sarcoidosis" 739, and "septic emboli" 740 are displayed as subcategory disease names of the "nonneoplastic" 737. Further, "nontuberculous mycobacteria (NTM)" 742 and "tuberculosis" 743 are displayed as subcategory disease names of the "mycobacteriosis" 741. Further, "bronchiectasis" 745 is displayed as a subcategory disease name of the "others" 744.

Figure 12:
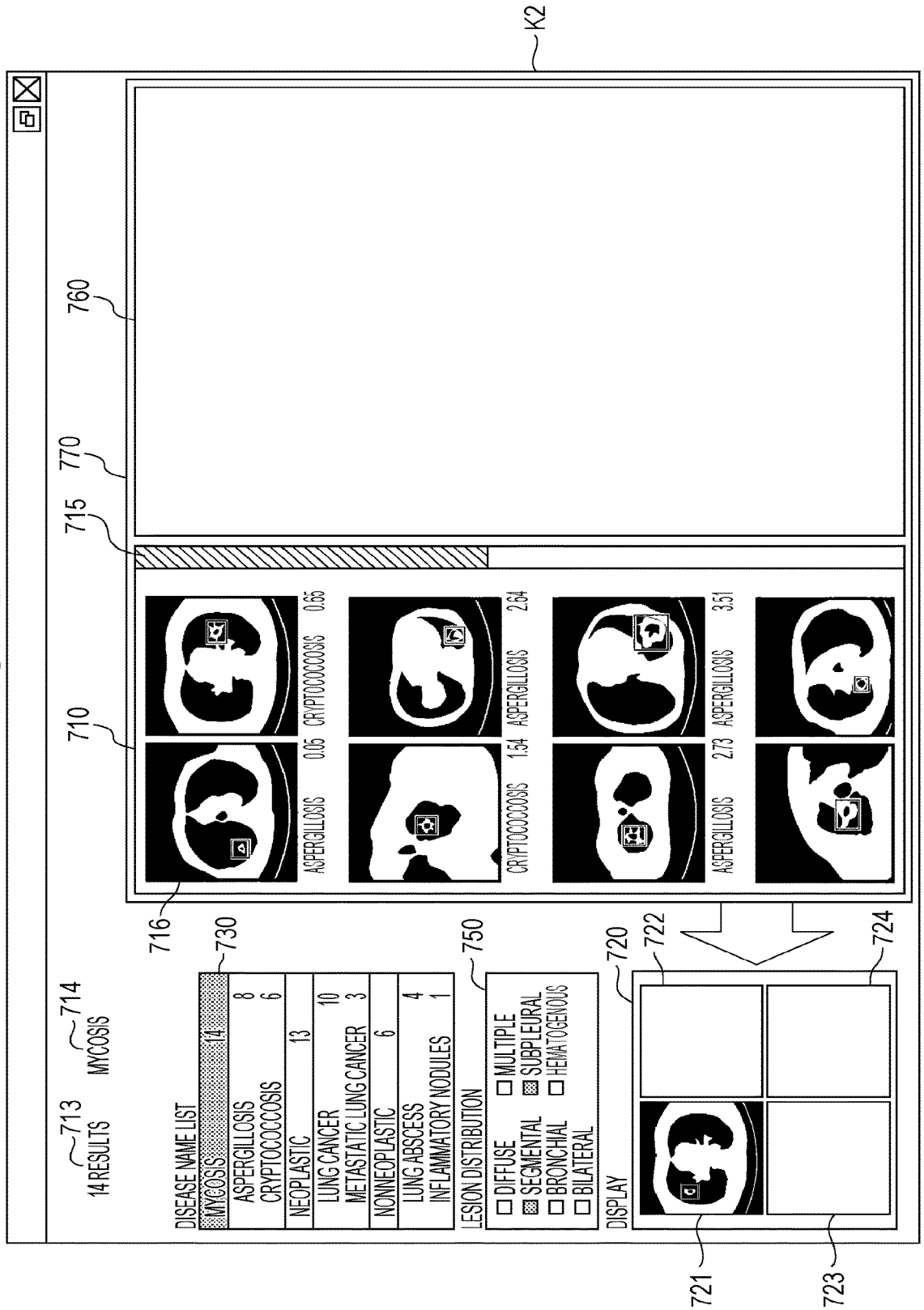
FIG. 12 is a diagram illustrating a basic screen obtained when similar cases are refined by "mycosis"
Figure 13:
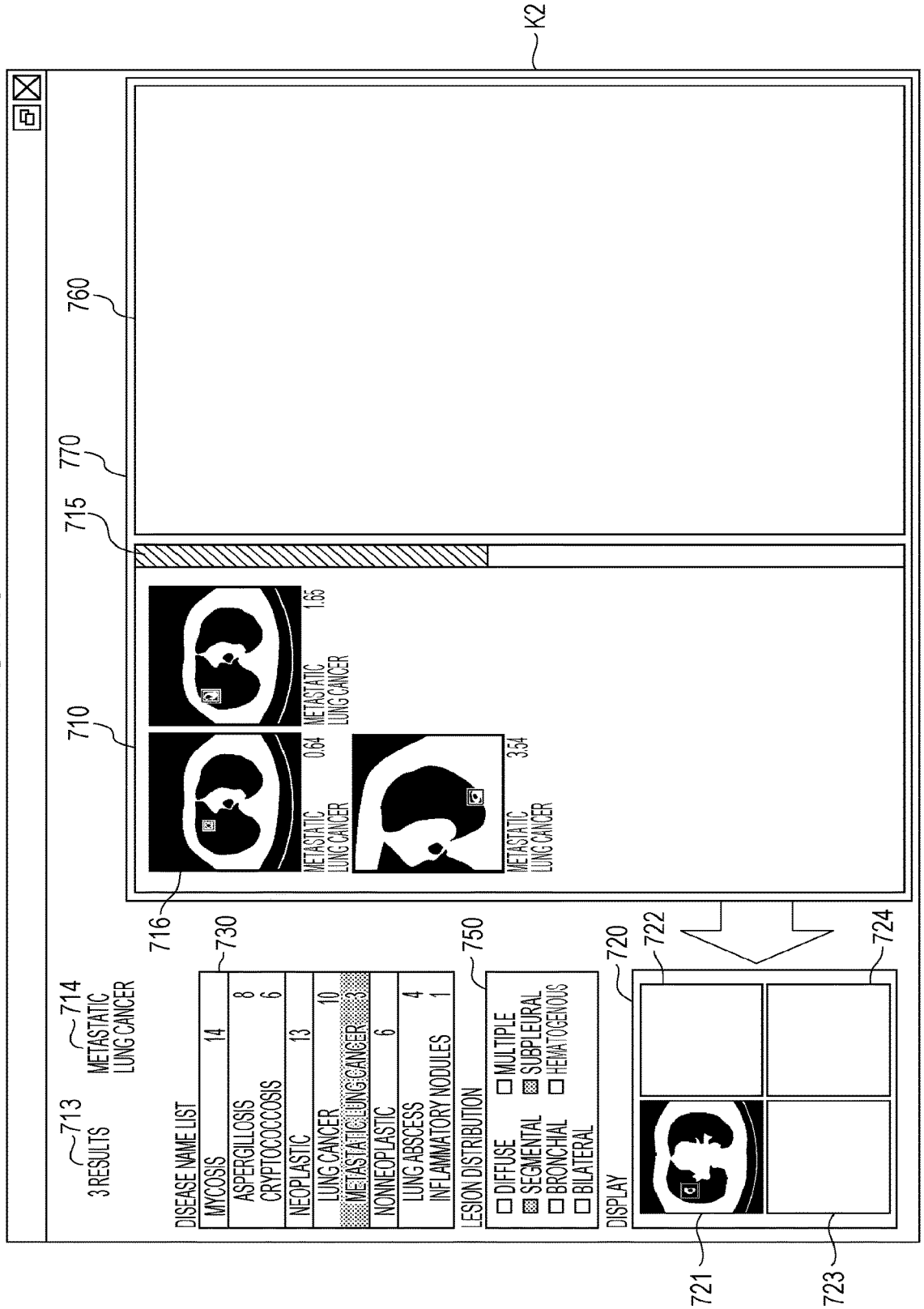
FIG. 13 is a diagram illustrating a basic screen obtained when similar cases are refined by "metastatic lung cancer"

Further, next to the major-category disease names and the subcategory disease names are the numbers of cases of the diseases indicated by the respective disease names. By selecting a row corresponding to any of the major-category disease names or subcategory disease names in the disease name list display area 730, the user can refine the similar cases to be displayed in the case display area 710. As illustrated in FIG. 9, immediately after a similar case search has been performed, 62 similar cases including diverse diseases and disorders are set as targets to be displayed. As a result of clicking on the row corresponding to the "mycosis" 731 in FIG. 11 with the mouse, as illustrated in FIG. 12, the display control unit 104 displays similar cases of mycoses in the case display area 710. Further, as a result of clicking on the row corresponding to the "metastatic lung cancer" 736 in FIG. 11 with the mouse, as illustrated in FIG. 13, the display control unit 104 displays similar cases of metastatic lung cancer in the case display area 710.

In this case, the display control unit 104 displays a disease name used for refinement in the display condition display area 714 so that the user can identify the refinement condition under which the similar cases currently being displayed in the case display area 710 have been obtained. FIG. 12 is a diagram illustrating the basic screen K2 obtained when similar cases are refined by "mycosis". FIG. 13 is a diagram illustrating the basic screen K2 obtained when similar cases are refined by "metastatic lung cancer".

In the example illustrated in FIG. 12, the term "Mycosis" is displayed in the display condition display area 714 since refinement is performed by "mycosis". In the example illustrated in FIG. 13, the term "Metastatic lung cancer" is displayed in the display condition display area 714 since refinement is performed by "metastatic lung cancer".

In this case, furthermore, the display control unit 104 displays, in the number-of-search-result display area 713, the number of similar cases currently being displayed in the case display area 710 so that the user can identify the number of similar cases currently being displayed in the case display area 710. In the example illustrated in FIG. 12, since there are 14 similar cases of mycoses, "14 results" is displayed in the number-of-search-result display area 713. In the example illustrated in FIG. 13, since there are three similar cases of metastatic lung cancer, "3 results" is displayed in the number-of-search-result display area 713.

With the function described above, similar cases of a disease estimated by a radiologist as a target to be diagnosed with imaging are displayed in the case display area 710, enabling the radiologist to easily confirm whether the case to be diagnosed is consistent with the estimated disease.

On the basic screen K2 illustrated in FIG. 9, the medical book display area 760 is located in the right portion of the similar case data display area 770. The medical book display area 760 is an area where a page of a certain medical book is displayed in accordance with the selection of the user.

Figure 14:
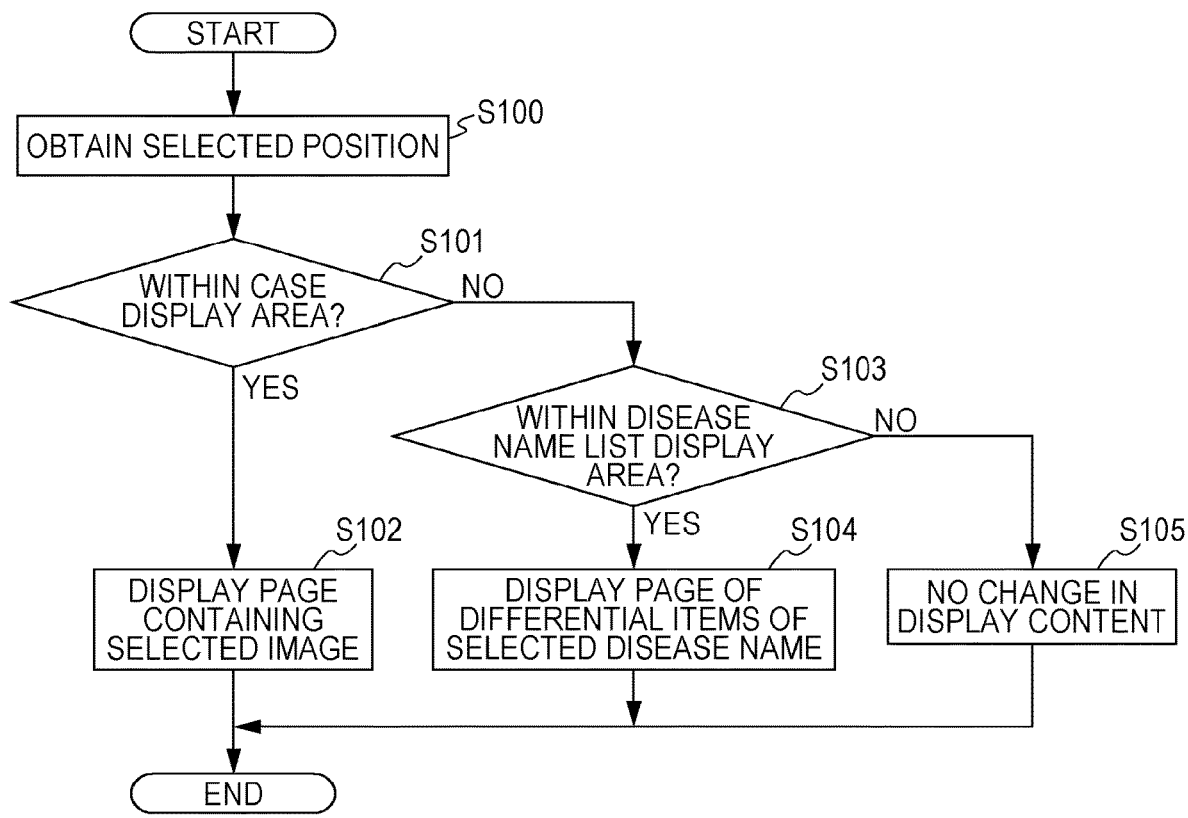
FIG. 14 is a flowchart illustrating a process performed by a display control unit or the like for display control of a medical book display area.

FIG. 14 is a flowchart illustrating a process performed by the display control unit 104 or the like for display control of the medical book display area 760. The display control of the medical book display area 760 will be described in detail hereinafter with reference to FIG. 14.

First, in S100, the input control unit 103 detects the position of a screen selected by the user on the basic screen K2. The display control unit 104 obtains the position of the screen selected by the user on the basic screen K2 from the input control unit 103.

Then, in S101, the display control unit 104 determines whether or not the position of the screen obtained in S100 is within the case display area 710. If the position of the screen obtained in S100 is within the case display area 710 (YES in S101), the process proceeds to S102. If the position of the screen is outside the case display area 710 (NO in S101), the process proceeds to S103.

Then, in S102, the display control unit 104 obtains similar case data 4000 (FIG. 32) corresponding to the selected similar case from the similar case data accumulation unit 301 on the basis of the position of the screen within the case display area 710 selected by the user on the basic screen K2, which is obtained from the input control unit 103. The display control unit 104 extracts an image ID 4200 from the obtained similar case data 4000.

The display control unit 104 obtains, from the image data management unit 224, the medical book image data 420 (FIG. 5) corresponding to the extracted image ID 4200. The display control unit 104 extracts the medical book ID 421 and the page number 425 from the obtained medical book image data 420. The display control unit 104 displays, in the medical book display area 760, the page corresponding to the extracted page number 425 of the medical book corresponding to the extracted medical book ID 421. Then, the process ends.

Figure 15:
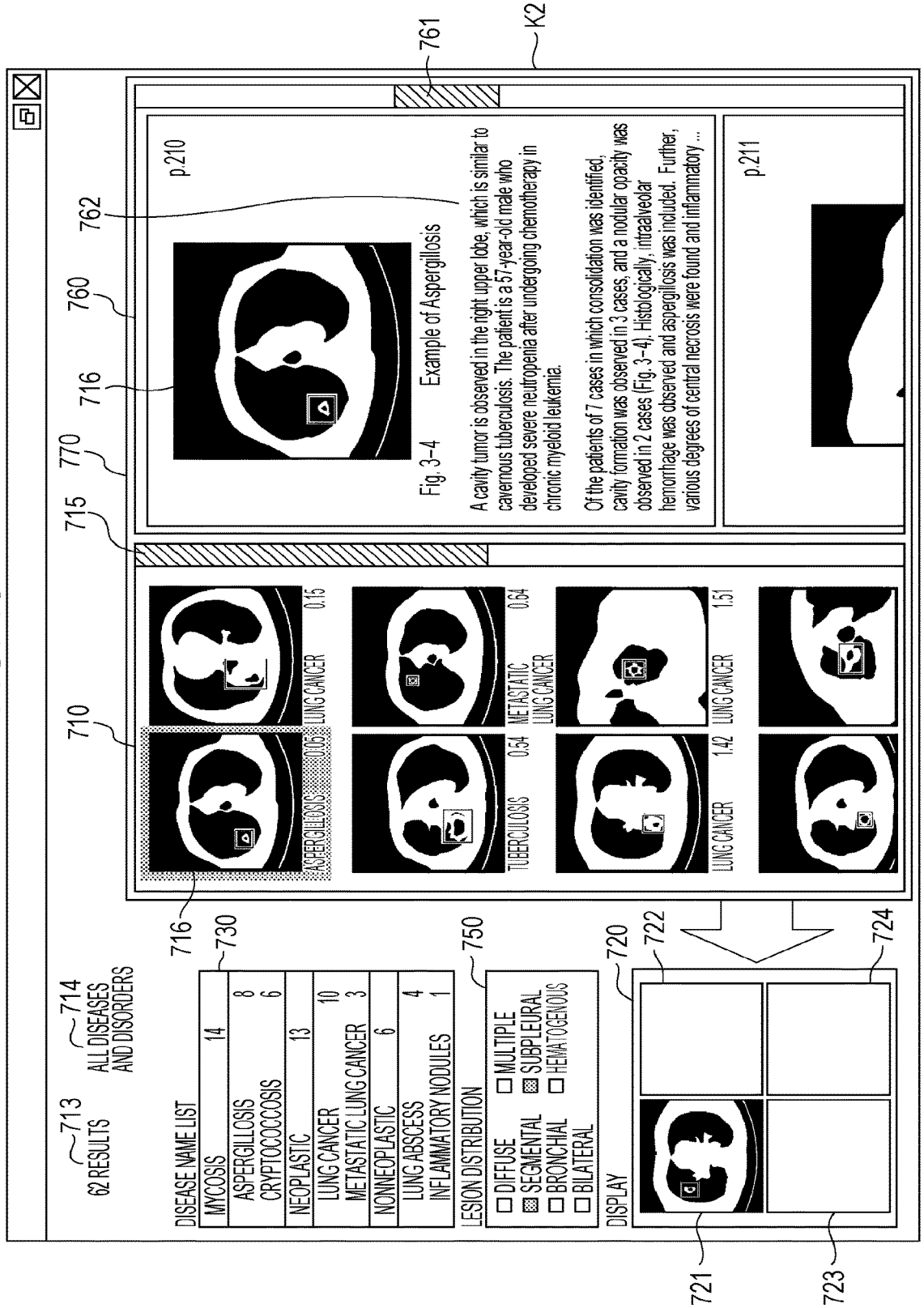
FIG. 15 is a diagram illustrating an example of a basic screen obtained when a selection is made in the case display area.

FIG. 15 is a diagram illustrating an example of the basic screen K2 displayed in S102 when the user selects a similar case 716 located in the upper left portion of the case display area 710 illustrated in FIG. 9. The medical book display area 760 shows a page of a medical book which contains an original image based on which the similar case 716 (thumbnail image) is generated.

Diagnostic information 762 on the similar case 716 is described on the page of the medical book illustrated in FIG. 15.

It is difficult to display all pages of the medical book in the medical book display area 760 at the same time. To address this difficulty, the medical book display area 760 has in the right portion thereof a scrollbar 761 that is vertically long, for example. The display control unit 104 vertically scrolls through page after page of the medical book displayed in the medical book display area 760 in accordance with the amount of movement of the scrollbar 761, which is detected by the input control unit 103. This enables the user to display a currently invisible page of the medical book in the medical book display area 760 so that the user can find the preceding and following descriptions.

Referring back to FIG. 14, in S103, the display control unit 104 determines whether or not the position of the screen obtained in S100 is within the disease name list display area 730. If the position of the screen obtained in S100 is within the disease name list display area 730 (YES in S103), the process proceeds to S104. If the position of the screen obtained in S100 is outside the disease name list display area 730 (NO in S103), the process proceeds to S105.

In S104, the display control unit 104 determines a selected disease name on the basis of the position of the screen within the disease name list display area 730 selected by the user on the basic screen K2, which is obtained from the input control unit 103. The display control unit 104 obtains, from the differential item information management unit 226, the differential item information 430 (FIG. 6) corresponding to the determined name of the disease (disease name). The display control unit 104 extracts the medical book ID 431 and the page number 434 from the obtained differential item information 430. The display control unit 104 displays the page corresponding to the extracted page number 434 of the medical book corresponding to the extracted medical book ID 431 in the medical book display area 760. Then, the process ends.

Figure 16:
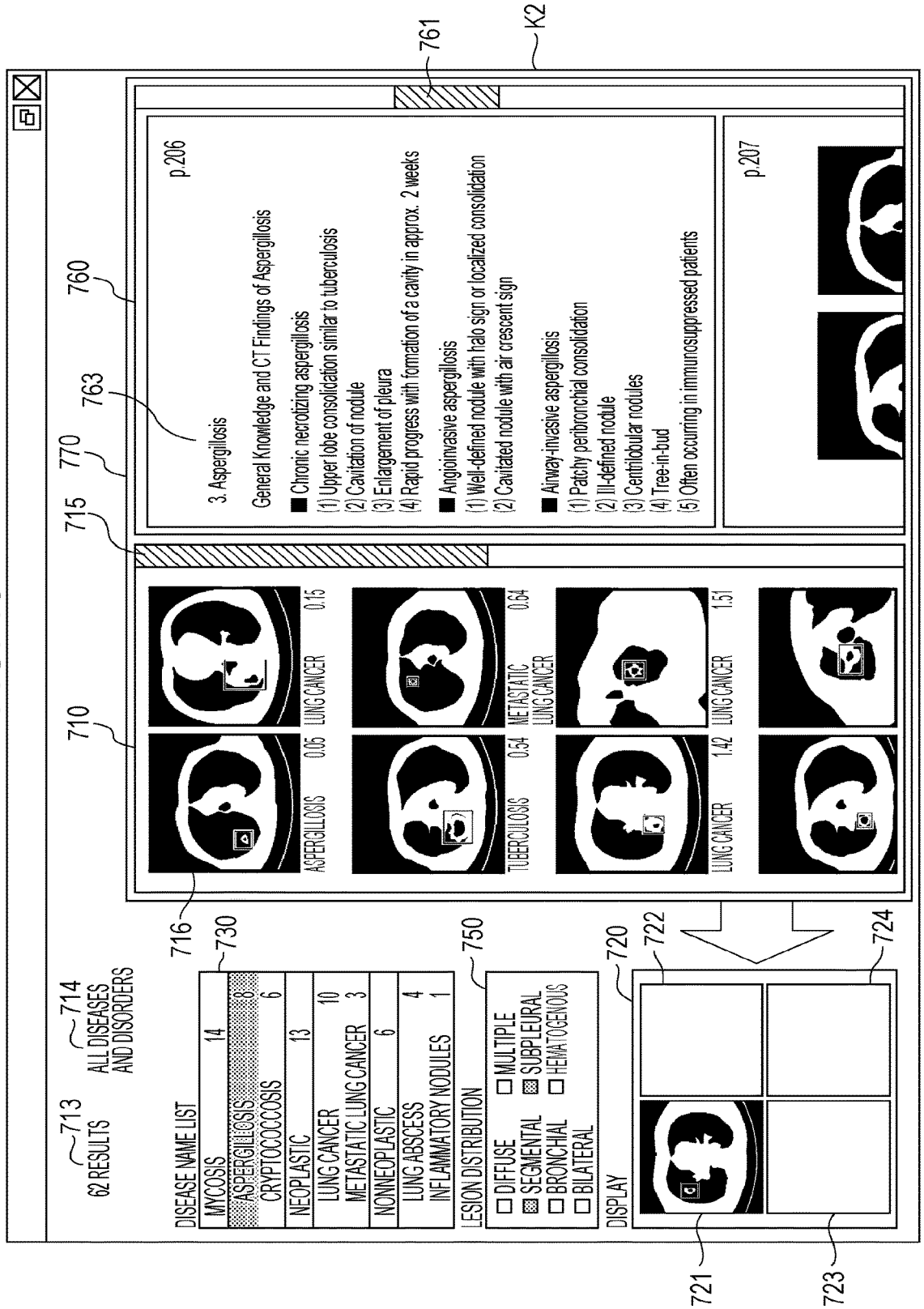
FIG. 16 is a diagram illustrating an example of a basic screen obtained when a selection is made in the disease name list display area.

FIG. 16 is a diagram illustrating an example of the basic screen K2 displayed in S104 when the user selects "aspergillosis" in the disease name list display area 730 illustrated in FIG. 9. The medical book display area 760 shows a page of a medical book which contains differential items 763 for defining the diagnosis of aspergillosis.

Referring back to FIG. 14, in S105, the display control unit 104 does not change the display of the medical book display area 760, and then the process ends. If the position of the screen selected by the user on the basic screen K2, which is obtained from the input control unit 103 in S100, is not within the case display area 710 (NO in S101) or not within the disease name list display area 730 (NO in S103), the display control unit 104 does not change the content displayed in the medical book display area 760.

A description will now be given of the reason why the content displayed in the medical book display area 760 changes between when the user (radiologist) selects a similar case (thumbnail image) in the case display area 710 and when the user (radiologist) selects a disease name in the disease name list display area 730.

There may be mainly two situations where the user (radiologist) searches for a thumbnail image (similar medical image) of a similar case that is similar to a search query image (target medical image) by using the case search system 300.

In the first situation, the radiologist wishes to see, for reference, disease names assigned to similar medical images that are similar to the target medical image because they do not come up with the disease name for the target medical image when viewing the target medical image. In this case, in a typical medical setting, the radiologist retrieves a medical image that is similar to the target medical image from among an enormous collection of medical images contained in medical books to determine the name of the disease in the target medical image by using, as a reference, the disease name assigned to the similar medical image.

As illustrated in FIG. 9, first, the basic screen K2 that includes the similar case data display area 770 including the case display area 710 displaying a plurality of similar medical images and the disease name list display area 730 displaying disease names is displayed on the display 101. When the radiologist makes a selection on the basic screen K2 using a contact member (e.g., the radiologist's finger), the input control unit 103 detects the selection. If the user's selection detected by the input control unit 103 for the first time after the basic screen K2 has been displayed is the selection of a similar medical image displayed in the case display area 710, it can be presumed the radiologist might not have come up with the disease name for the target medical image.

In this case, a page of an electronic medical book which contains the selected similar medical image and which describes diagnostic information on the selected similar medical image may be displayed in the medical book display area 760. This is because, when comparing a target medical image with a similar medical image, the radiologist compares the features of the images also taking into account diagnostic information concerning the similar medical image.

The diagnostic information includes, for example, a type of lesion pattern (such as nodal or diffuse) in the similar medical image, patient clinical information (such as gender, age, and blood test results) regarding the similar medical image, and the patient's follow-up information. In the example illustrated in FIG. 15, the diagnostic information 762 includes "cavernous" as the pattern of the lesion, "57-year-old male" as patient clinical information, and "the patient developed severe neutropenia after undergoing chemotherapy in chronic myeloid leukemia" as the patient's follow-up information.

If the radiologist does not come up with the name of the disease of the patient for whom image interpretation is to be performed, the radiologist matches diagnostic information against the patient's medical image, follow-up information, and the like to identify the name of the disease of the patient. As such, the diagnostic information is as important as or more important than similarity of features of images in terms of comparison between a target medical image and a similar medical image. The diagnostic information is described in the electronic medical book at a location adjacent to the medical image.

In this embodiment, when the input control unit 103 detects a selection of a similar medical image displayed in the case display area 710 by a user (YES in S101 in FIG. 14), the display control unit 104 displays, in the medical book display area 760, a page of the electronic medical book which contains the selected similar medical image (S102 in FIG. 14). Thus, in this embodiment, when a user selects a similar medical image displayed in the case display area 710, the diagnostic information 762 concerning the selected similar medical image can be presented to the user.

Furthermore, when a user selects a similar medical image displayed in the case display area 710, the diagnostic information 762 is presented to the user. This can prevent the user from overlooking the diagnostic information 762. In an actual diagnostic setting, even in a case where a target medical image and a selected similar medical image are similar to each other in terms of image features, it may be concluded that, as a result of consideration of the diagnostic information 762, the two images are images of different diseases. Thus, this embodiment can effectively prevent overlooking of the diagnostic information 762, and can also lead to the prevention of misdiagnosis.

In the second situation, the radiologist comes up with a plurality of possible disease names for a target medical image when viewing the target medical image, and wishes to obtain information necessary to determine which of the possible disease names is correct. In this case, in a typical medical setting, the radiologist reads a medical book page for each of the plurality of disease names thought of by the radiologist, and checks differential items serving as information necessary to determine the name of the disease. By checking the target medical image and the differential items in detail, the radiologist definitively diagnose the disease in the target medical image.

As illustrated in FIG. 9, the basic screen K2 that includes the similar case data display area 770 including the case display area 710, and the disease name list display area 730 is displayed on the display 101. If a user's selection detected by the input control unit 103 for the first time after the basic screen K2 illustrated in FIG. 9 has been displayed is the selection of a disease name displayed in the disease name list display area 730, it can be presumed that the radiologist might have come up with a plurality of possible disease names for the target medical image.

Accordingly, when the selection of a disease name displayed in the disease name list display area 730 is detected, information necessary to determine which of a plurality of possible disease names that the radiologist has come up with is correct may be presented to the radiologist in view of efficient diagnosis. That is, the differential items 763 (FIG. 16), which are information necessary for determining a specific disease name, may be presented to the radiologist.

In this embodiment, when the input control unit 103 detects the selection of a disease name displayed in the disease name list display area 730 (YES in S103 in FIG. 14), as illustrated in FIG. 16, the display control unit 104 displays, in the medical book display area 760, a page of an electronic medical book which contains differential items corresponding to the selected disease name (S104 in FIG. 14). Accordingly, this embodiment enables information necessary for diagnosis, which is desired by a radiologist, to be effectively presented to the radiologist.

As described above, it is presumably determined which of the two situations described above is the current situation in accordance with the content of the user's selection detected for the first time after the basic screen K2 that includes the similar case data display area 770 including the case display area 710 displaying a plurality of similar medical images and the disease name list display area 730 displaying disease names has been displayed on the display 101.

In addition, information necessary for diagnosis, which is suitable for each situation, can be presented to the radiologist. This can save the radiologist time and labor involved in searching for necessary information from electronic medical books. In addition, making the radiologist concentrate on making a decision about diagnosis and treatment can improve the accuracy of the decision about diagnosis and treatment.

For example, in FIG. 15, the medical book display area 760 is located in a portion of the similar case data display area 770 on the basic screen K2. However, the present disclosure is not limited thereto. In order to display, in the medical book display area 760 on the basic screen K2, pages of an electronic medical book which contain differential items corresponding to a selected disease name, as illustrated in FIG. 17, the display control unit 104 may use the similar case data display area 770 in its entirety as the medical book display area 760 and may remove the case display area 710 from the similar case data display area 770.

Figure 17:
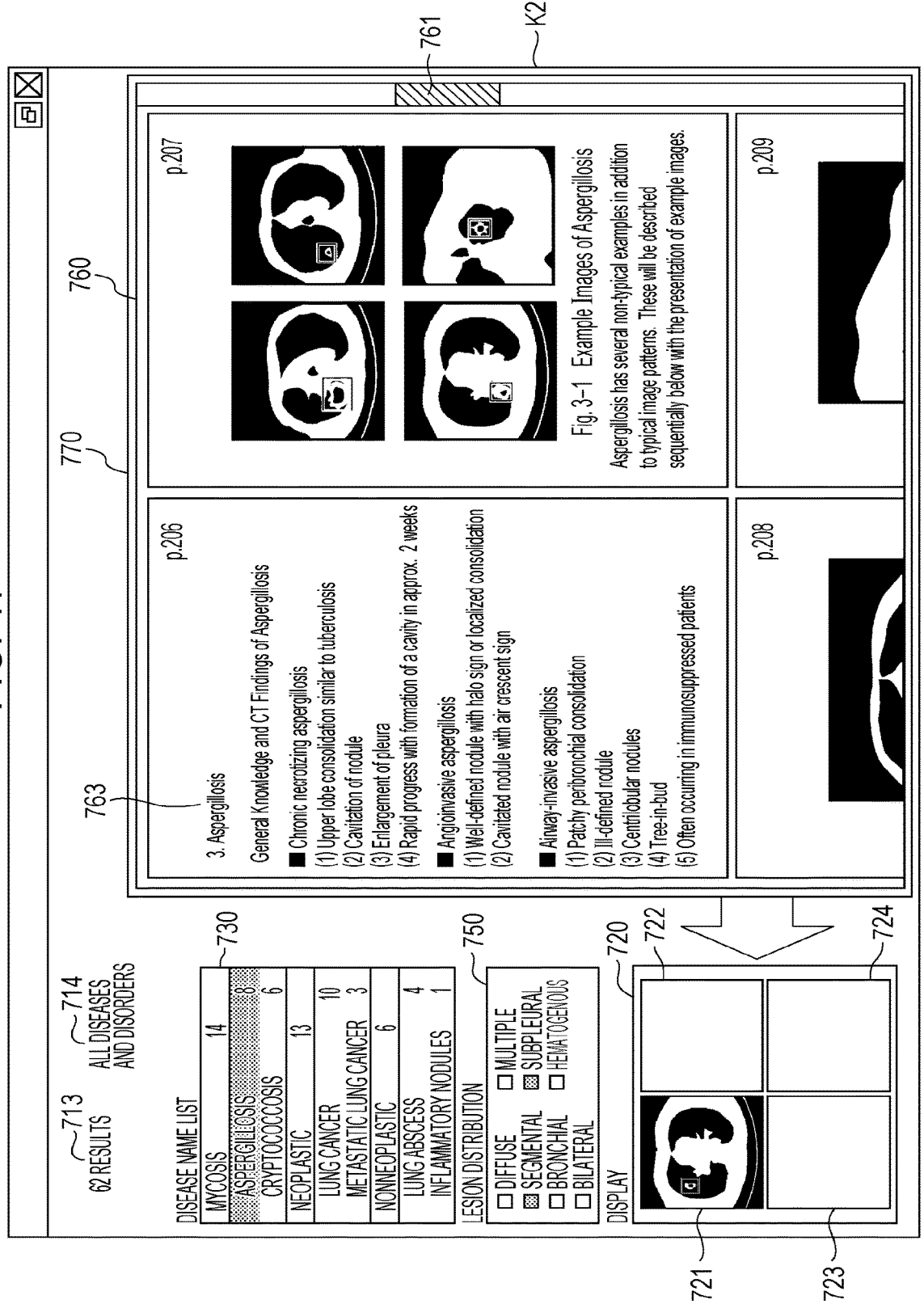
FIG. 17 is a diagram illustrating an example of a basic screen on which a similar case data display area is used in its entirety as a medical book display area.

FIG. 17 is a diagram illustrating an example of the basic screen K2 on which the similar case data display area 770 is used in its entirety as the medical book display area 760. As illustrated in FIG. 17, the case display area 710 has been removed from the similar case data display area 770.

In FIG. 17, the display control unit 104 displays, in the upper left portion of the medical book display area 760, the page containing the differential items 763 displayed illustrated in FIG. 16. The display control unit 104 further displays the next page in the upper right portion of the medical book display area 760, an upper portion of the subsequent page in the lower left portion of the medical book display area 760, and an upper portion of the subsequent page in the lower right portion of the medical book display area 760.

A page of an electronic medical book which contains differential items corresponding to a selected disease name is displayed in the medical book display area 760 in the following case: The user's selection detected by the input control unit 103 for the first time after the basic screen K2 that includes the case display area 710 displaying a plurality of similar medical images and the disease name list display area 730 has been displayed on the display 101 is the selection of a disease name displayed in the disease name list display area 730.

In this case, it can be presumed that a radiologist who has viewed the target medical image might have come up with a plurality of possible disease names for the target medical image. It can also be presumed that the radiologist might wish to check every differential items corresponding to the plurality of disease names thought of by the radiologist. In this case, similar medical images are less likely to need to be displayed on the basic screen K2.

Accordingly, the display control unit 104 may display, in the medical book display area 760, pages of an electronic medical book which contain differential items corresponding to a selected disease name, by, as illustrated in FIG. 17, using the similar case data display area 770 in its entirety as the medical book display area 760. That is, the case display area 710 is removed from the similar case data display area 770, and no similar medical images are displayed on the basic screen K2. This can result in effective presentation, to a radiologist, of information desired by the radiologist, and can lead to effective use of the basic screen K2 with a limited display area.

Alternatively, in a case where the similar case data display area 770 is used in its entirety as the medical book display area 760, the display control unit 104 may display a basic screen K2 illustrated in FIG. 18.

FIG. 18 is a diagram illustrating an example of the basic screen K2 on which a page of an electronic medical book which contains the differential items 763 corresponding to the selected disease name (FIG. 16) and a page of the electronic medical book which contains a medical image 764 corresponding to the selected disease name are displayed side by side in the medical book display area 760.

For example, when a user selects "aspergillosis" in the disease name list display area 730 using a contact member (e.g., the user's finger) while the basic screen K2 illustrated in FIG. 9 is being displayed, the input control unit 103 detects the selected position. The display control unit 104 obtains the detected selected position from the input control unit 103. The display control unit 104 determines "aspergillosis" on the basis of the obtained selected position.

The display control unit 104 obtains the differential item information 430 (FIG. 6) in which the disease name 432 is "aspergillosis" from the differential item information management unit 226. The display control unit 104 extracts the medical book ID 431 and the page number 434 from the obtained differential item information 430. The display control unit 104 displays, in the medical book display area 760, the page corresponding to the page number 434 (in the example illustrated in FIG. 18, page 206) of the medical book corresponding to the extracted medical book ID 431.

The display control unit 104 further obtains, using the definitely diagnosed disease name "aspergillosis" and the medical book ID 431 extracted from the differential item information 430, the medical book image data 420 (FIG. 5) in which the medical book ID 421 and the definitely diagnosed disease name 424 match the medical book ID 431 and the definitely diagnosed disease name "aspergillosis", respectively, from the image data management unit 224. The display control unit 104 extracts the page number 425 from the obtained medical book image data 420. The display control unit 104 displays the page corresponding to the extracted page number 425 (in the example illustrated in FIG. 18, page 210) in the medical book display area 760 so that the page corresponding to the extracted page number 425 and the page containing the differential items 763 are arranged side by side.

In FIG. 18, as in FIG. 17, the similar case data display area 770 is used in its entirety as the medical book display area 760. Thus, as in FIG. 17, the embodiment illustrated in FIG. 18 enables a plurality of pages of an electronic medical book to be displayed in the medical book display area 760 without being significantly reduced in size.

In FIG. 18, the page of the electronic medical book which contains the differential items 763 corresponding to the selected disease name (in the example illustrated in FIG. 18, page 206) and the page containing the medical image 764 corresponding to the selected disease name (in the example illustrated in FIG. 18, page 210) are displayed side by side in the medical book display area 760. This enables the viewer to simultaneously check the differential items 763 necessary to define diagnosis and their actual example, namely, the medical image 764. This can result in effective presentation of information useful for a radiologist to diagnose.

Furthermore, for example, in response to the user's selection of a similar case in the case display area 710 on the basic screen K2 illustrated in FIG. 9, as illustrated in FIG. 15, a page of a medical book which contains the similar case (thumbnail image) is displayed in the medical book display area 760. In this case, the display control unit 104 may display the similar case (thumbnail image) selected in the case display area 710 in a highlighted manner.

Figure 19:
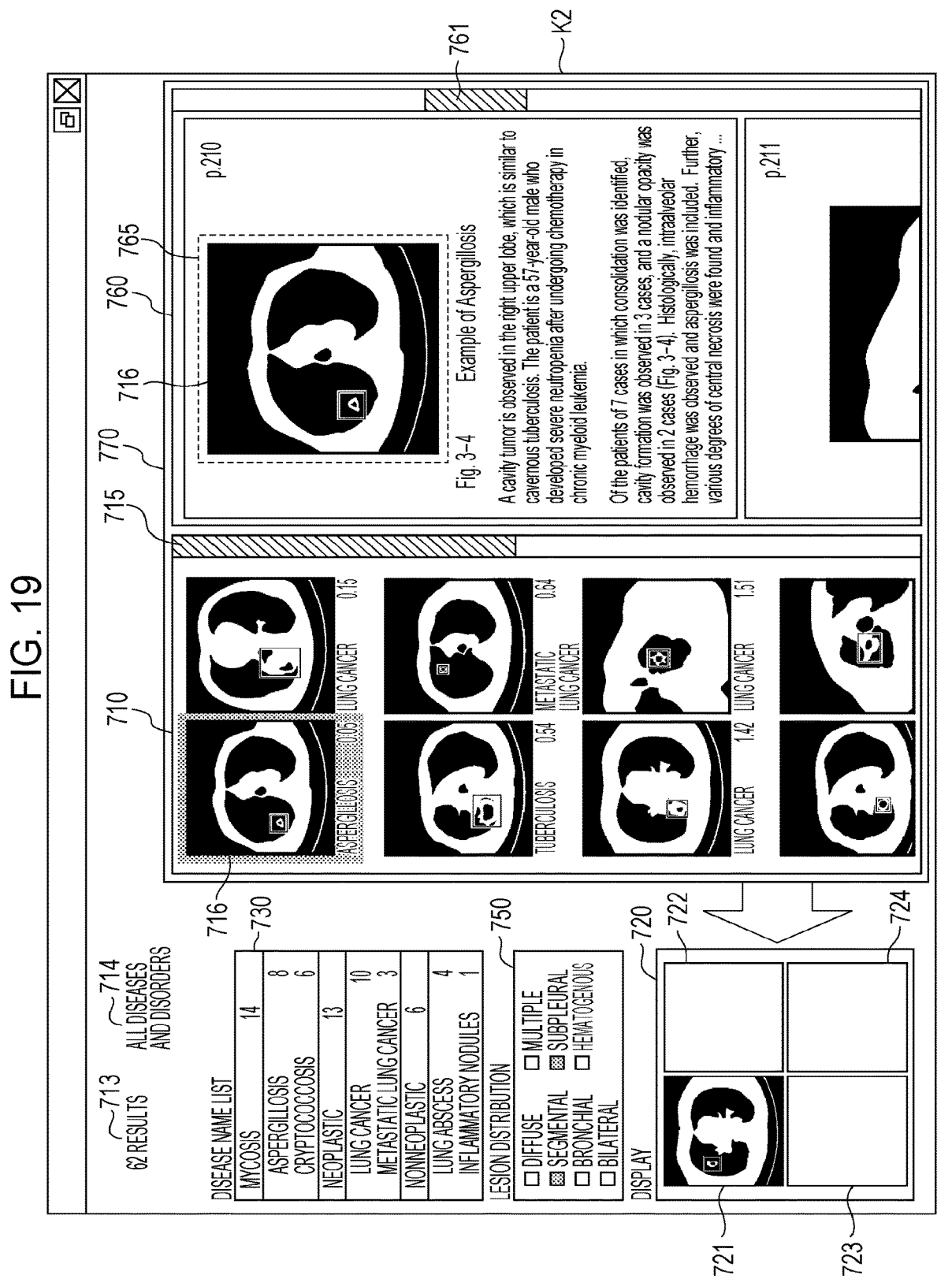
Figure 20:
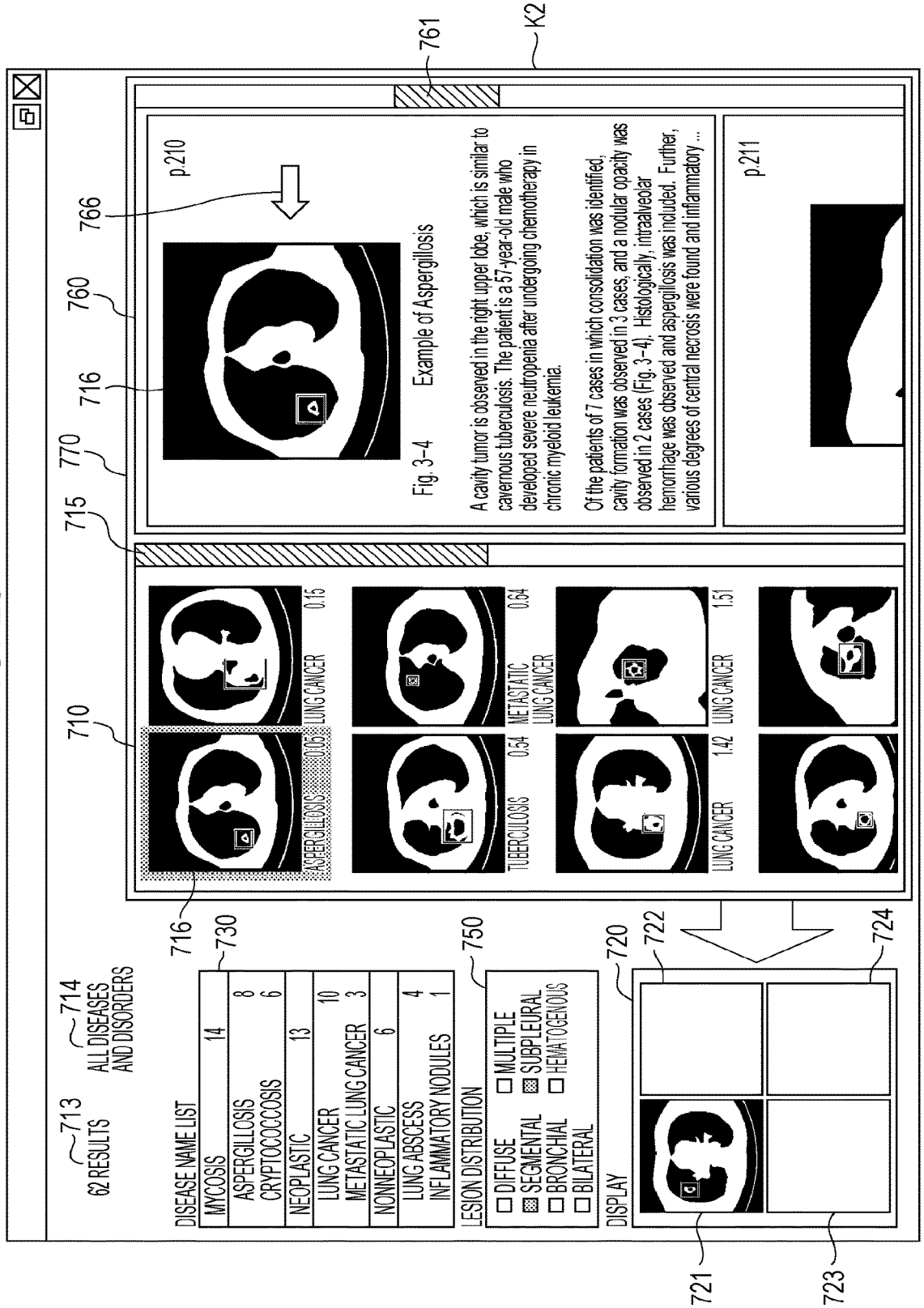
FIG. 20 is a diagram illustrating another example of a basic screen on which a selected similar case is displayed in the medical book display area in a highlighted manner.

FIG. 19 and FIG. 20 are diagrams illustrating examples of the basic screen K2 on which the similar case 716 (thumbnail image) selected in the case display area 710 is displayed in the medical book display area 760 in a highlighted manner. Examples of the method for highlighted display include a method in which, as illustrated in FIG. 19, the display control unit 104 displays a frame 765, such as a dotted-line frame, surrounding the selected similar case 716 (thumbnail image).

The display control unit 104 may also display a frame in a different color such as red or yellow or display a blinking frame to highlight the selected similar case 716 (thumbnail image). Alternatively, as illustrated in FIG. 20, the display control unit 104 may highlight the selected similar case 716 (thumbnail image) by displaying an annotation 766 such as an arrow.

In general, a page of an electronic medical book often contains a plurality of medical images. Thus, even if a page of an electronic medical book is displayed in the medical book display area 760, it is difficult for a radiologist to immediately determine which medical image matches the selected similar case 716 (thumbnail image).

In the embodiments illustrated in FIG. 19 and FIG. 20, the selected similar case 716 (thumbnail image) is highlighted and displayed. This can save time and labor involved in searching for the selected similar case 716 (thumbnail image) from among a plurality of medical images contained on a page of an electronic medical book. As a result, it is possible to make the radiologist concentrate on diagnosing, leading to an improvement in the accuracy of diagnosis and treatment.

In addition, when a page of an electronic medical book which contains the selected similar case 716 (thumbnail image) is to be displayed in the medical book display area 760, the display control unit 104 may display the selected similar case 716 (thumbnail image) contained on the page of the electronic medical book at a predetermined position within the medical book display area 760.

Figure 21:
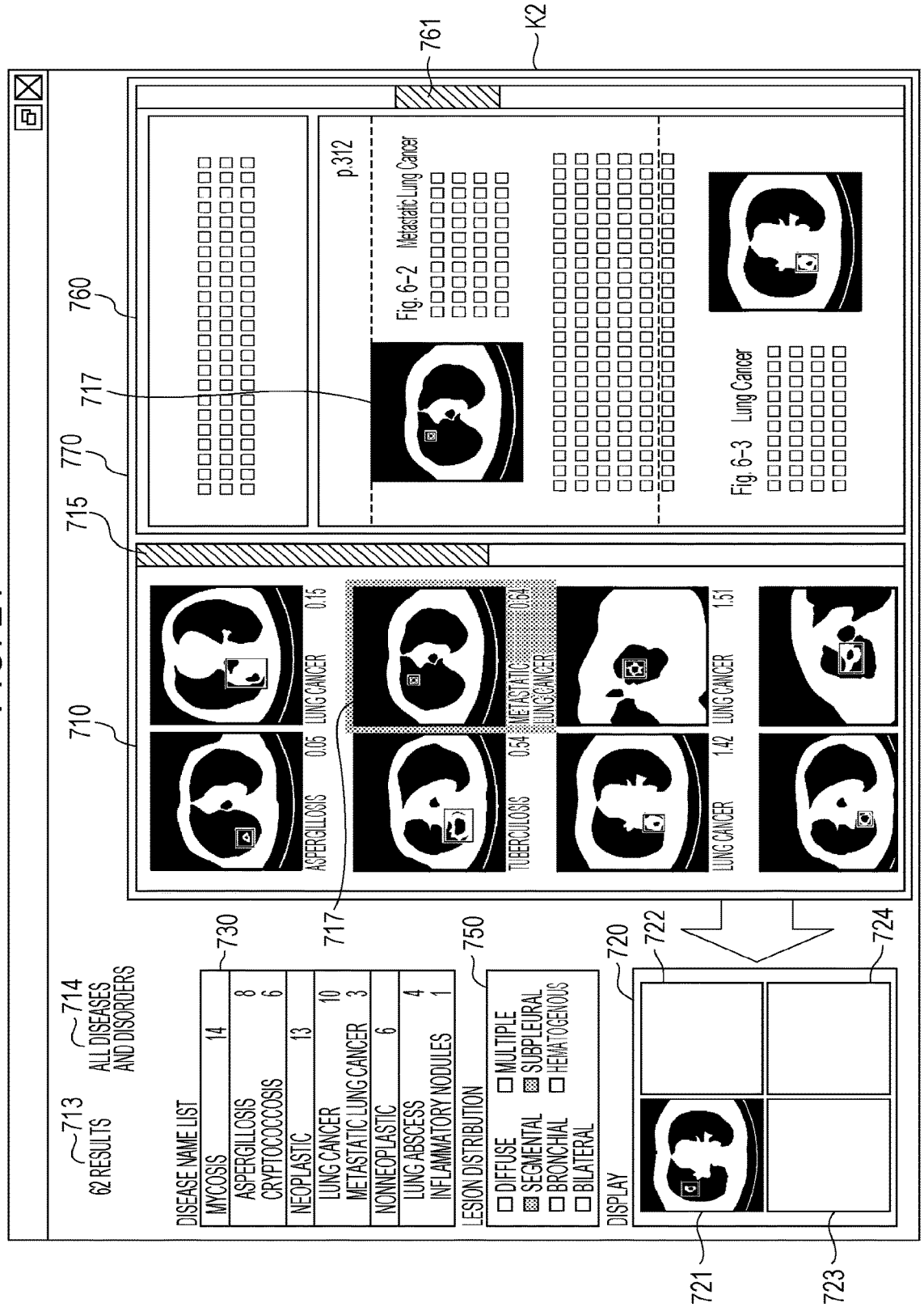
FIG. 21 is a diagram illustrating an example in which a selected similar case is displayed at a predetermined position within the medical book display area.
Figure 22:
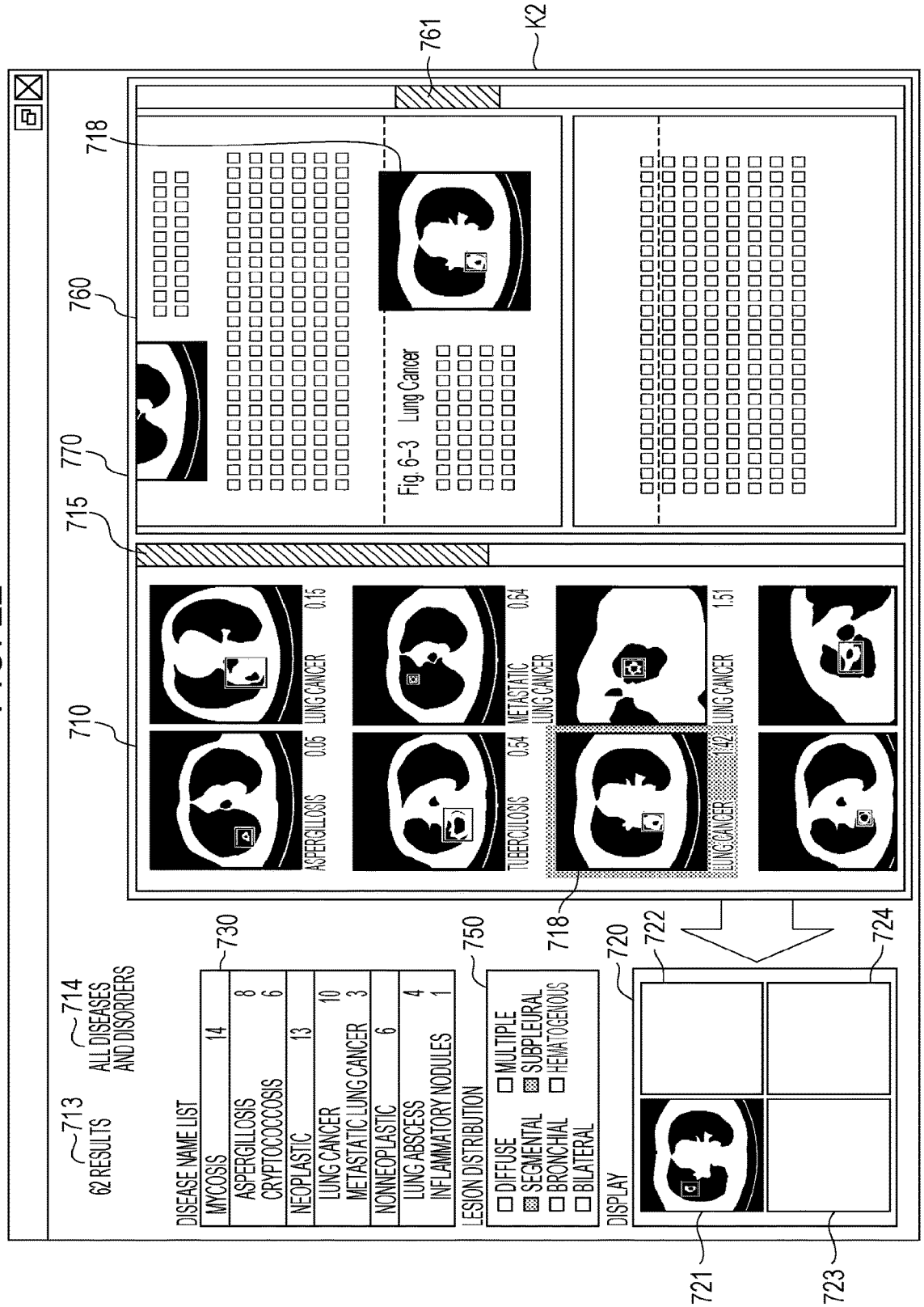
FIG. 22 is a diagram illustrating an example in which a selected similar case is displayed at a predetermined position in the medical book display area.

FIG. 21 and FIG. 22 are diagrams illustrating examples in which the selected similar case 716 (thumbnail image) is displayed at a predetermined position within the medical book display area 760. FIG. 21 illustrates an example of the basic screen K2 on which, in response to the selection of a similar case 717 at the second row and the second column in the case display area 710, the selected similar case 717 is displayed starting at a position about one third from the top of the medical book display area 760.

For example, when a user selects the similar case 717 at the second row and the second column in the case display area 710 using a contact member (e.g., the user's finger) while the basic screen K2 illustrated in FIG. 9 is being displayed, the input control unit 103 detects the selected position. The display control unit 104 obtains the detected selected position from the input control unit 103. The display control unit 104 determines the similar case 717 at the second row and the second column on the basis of the obtained selected position, and obtains the similar case data 4000 (FIG. 32) corresponding to the determined similar case 717 from the similar case data accumulation unit 301. The display control unit 104 extracts the image ID 4200 from the obtained similar case data 4000. The display control unit 104 obtains the medical book image data 420 (FIG. 5) corresponding to the extracted image ID 4200 from the image data management unit 224.

The display control unit 104 extracts the medical book ID 421, the page number 425, and the line number 426 from the obtained medical book image data 420. The display control unit 104 searches for the medical book corresponding to the extracted medical book ID 421. The display control unit 104 searches for the page corresponding to the page number 425 of the medical book found as a result of the search. The display control unit 104 displays the page in the medical book display area 760 so that the line corresponding to the line number 426 on the page found as a result of the search is located at a position about one third from the top of the medical book display area 760.

FIG. 22 illustrates an example of the basic screen K2 on which, in response to the selection of a similar case 718 at the third row and the first column in the case display area 710, the selected similar case 718 is displayed starting at a position about one third from the top of the medical book display area 760.

In FIG. 21 and FIG. 22, the line corresponding to the line number 426 associated with the image ID 423 of a selected similar case (thumbnail image) is located at a position about one third from the top. However, the present disclosure is not limited thereto. The position may be determined in advance by a designer or may be set by a user.

In general, a page of an electronic medical book often contains a plurality of medical images. Thus, even if a page of an electronic medical book is displayed in the medical book display area 760, it is difficult for a radiologist to immediately determine which medical image matches the selected similar case (thumbnail image).

In the embodiments illustrated in FIG. 21 and FIG. 22, the display control unit 104 displays a similar case (thumbnail image) selected by a user at a predetermined position within the medical book display area 760. This can save time and labor involved in searching for the selected similar case (thumbnail image) from among a plurality of medical images contained on a page of an electronic medical book. As a result, it is possible to make the radiologist concentrate on diagnosing, leading to an improvement in the accuracy of diagnosis and treatment.

Referring back to FIG. 9, the distribution list display area 750 with the heading "lesion distribution" is located in the left middle portion of the basic screen K2. The distribution list display area 750 shows some types of lesion distribution seen in all the similar cases obtained from the case search system 300 as a result of the similar case search.

Figure 23:
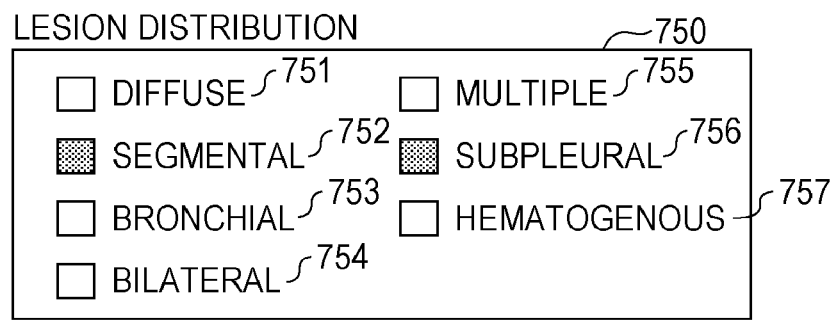
FIG. 23 is an enlarged view of a distribution list display area.

FIG. 23 is an enlarged view of the distribution list display area 750. In the example illustrated in FIG. 23, the names of seven lesion distributions are displayed, and checkboxes are placed to the left of the respective names of the lesion distributions. In the example illustrated in FIG. 23, "diffuse" 751, "segmental" 752, "bronchial" 753, "bilateral" 754, "multiple" 755, "subpleural" 756, and "hematogenous" 757 are displayed as lesion distributions.

The lesion distributions described above are defined in advance, and each similar case is given in advance a distribution flag value ("1" for Applicable or "0" for Not Applicable) indicating the applicability of the similar case to each of the "diffuse" 751 to the "hematogenous" 757. In some similar cases, the distribution flag values for all the lesion distributions may be set to Not Applicable ("0"), and, in other similar cases, the distribution flag values for a plurality of lesion distributions may be set to Applicable ("1").

The case search system 300 according to this embodiment searches for a similar case that has a region of interest similar to a region of interest set by a user on a slice image of the case to be diagnosed. A lesion may be present in a slice image other than the slice image on which the region of interest has been set by the user. In some cases, furthermore, the user may wish to, after searching for a similar case using the slice image on which the region of interest has been set, compare a slice image other than the slice image on which the region of interest has been set with the similar case found as a result of the search. In these cases, the user inputs a slice-to-slice switching operation on the medical image viewer 610 to display a different slice image, and compares the displayed slice image with the found similar case. If a similar case related to the lesion of interest among all the similar cases found as a result of the search is displayed in the case display area 710, the operation of extracting a slice image having the desired lesion from among slice images other than the slice image on which the region of interest has been set can be smoothly performed. Accordingly, this embodiment provides a function of refining the found similar cases according to the desired lesion distribution to make the operation described above smoother.

In this embodiment, the lesion distributions indicated by the "diffuse" 751 to the "hematogenous" 757 illustrated in FIG. 23 are used as lesion distributions in the pulmonary field. In addition, as illustrated in FIG. 23, the display control unit 104 displays the checkboxes and the names of the lesion distributions in such a manner that a lesion distribution available for refinement is active and a lesion distribution not available for refinement is inactive. Here, the "active" state refers to a state having a higher luminance than the "inactive" state, and the "inactive" state refers to a state having a lower luminance than the "active" state.

In the example illustrated in FIG. 23, the "diffuse" 751, the "bronchial" 753 to the "multiple" 755, and the "hematogenous" 757 are displayed as active, whereas the "segmental" 752 and the "subpleural" 756 are displayed as inactive. This is because the distribution flag values for the "diffuse" 751, the "bronchial" 753 to the "multiple" 755, and the "hematogenous" 757 are currently set to "1" (Applicable) in at least one similar case among all the similar cases obtained as a result of the similar case search, whereas the distribution flag values for the "segmental" 752 and the "subpleural" 756 are currently set to "O" (Not Applicable) in all the obtained similar cases.

When the input control unit 103 detects that one or more of the checkboxes that are active have been checked, the display control unit 104 causes similar cases that meet a lesion condition or conditions for which the checkbox or checkboxes have been checked to be displayed in the case display area 710.

Note that the distribution flag values for the "segmental" 752 and the "subpleural" 756 are set to "O" (Not Applicable) in any of the similar cases obtained as a result of the search. Thus, if the checkboxes for the "segmental" 752 and the "subpleural" 756 are allowed to be checked, even though the checkboxes for such lesion distributions are checked, no similar cases will be displayed in the case display area 710. In this case, it is meaningless to check the checkboxes. To avoid this situation, in this embodiment, a lesion distribution for which the distribution flag value is set to "O" (Not Applicable) in any of the similar cases obtained as a result of the search is displayed as inactive.

Figure 24:
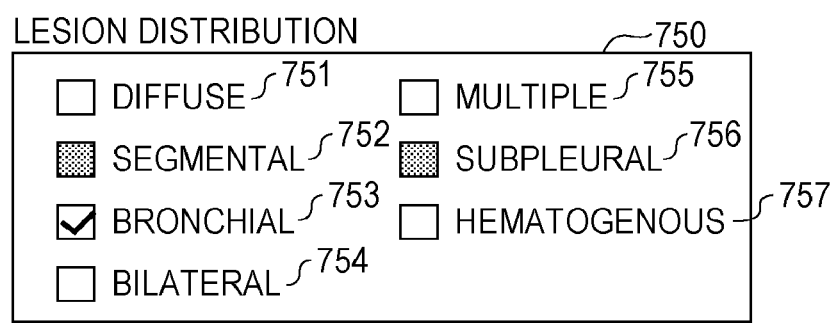
FIG. 24 is a diagram illustrating a distribution list display area in which a checkbox is checked.
Figure 25:
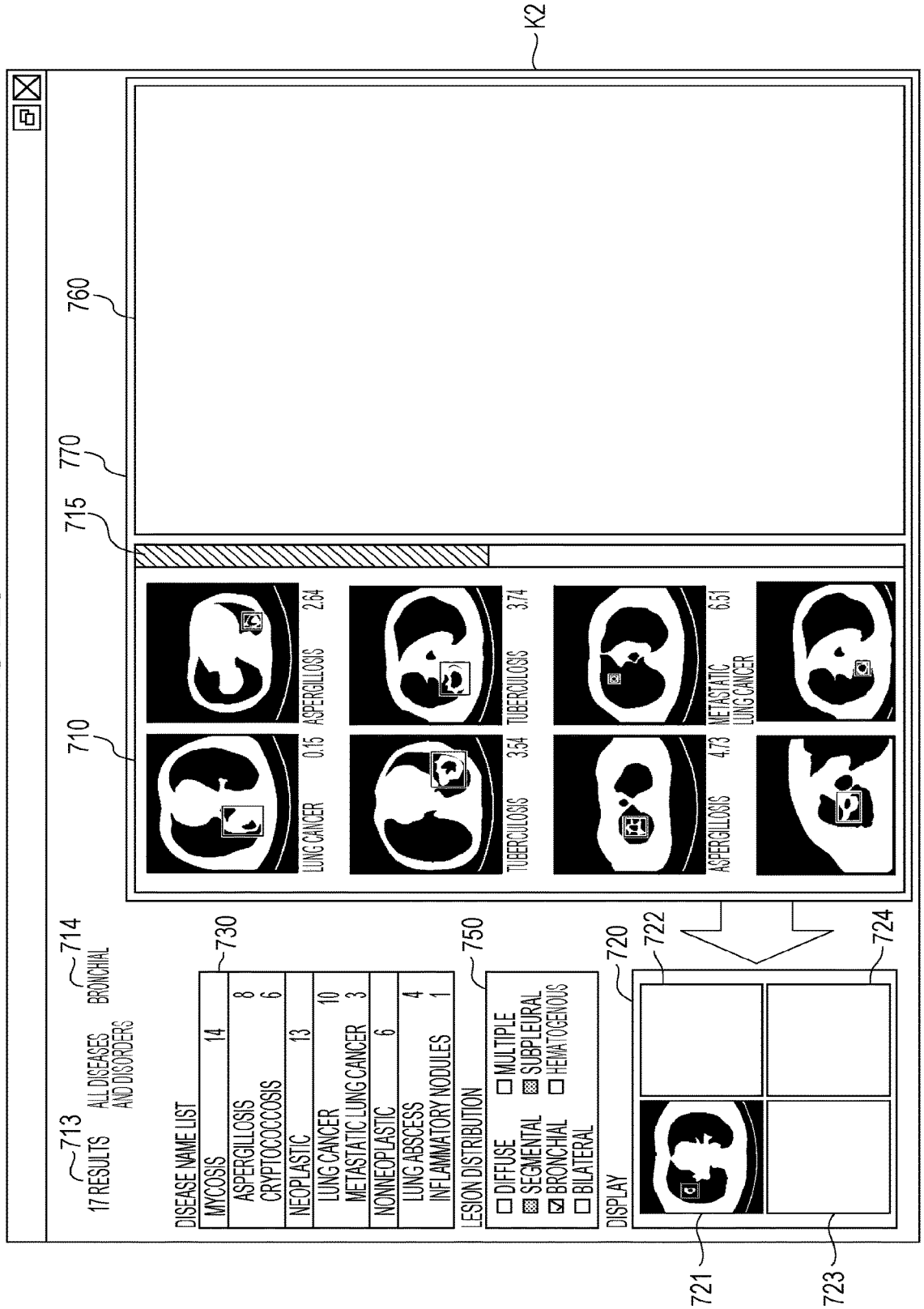
FIG. 25 is a diagram illustrating a basic screen on which refinement is performed by a bronchial lesion distribution.

FIG. 24 is a diagram illustrating the distribution list display area 750 in which some checkboxes are checked. FIG. 25 is a diagram illustrating a basic screen K2 on which refinement is performed according to the bronchial lesion distribution. As illustrated in FIG. 24, when the checkbox for the "bronchial" 753 is checked, as illustrated in FIG. 25, the display control unit 104 displays similar cases having the bronchial lesion distribution in the case display area 710. In the illustrated example, 17 similar cases have the bronchial lesion distribution. Thus, the display control unit 104 displays "17 results" in the number-of-search-result display area 713. The display control unit 104 further displays the disease name(s) to be displayed and the name of the lesion distribution, i.e., "bronchial", in the display condition display area 714. In the example illustrated in FIG. 25, there is no refinement according to a disease name given in the disease name list display area 730. Thus, "all diseases and disorders" is displayed in the display condition display area 714.

Figure 27:
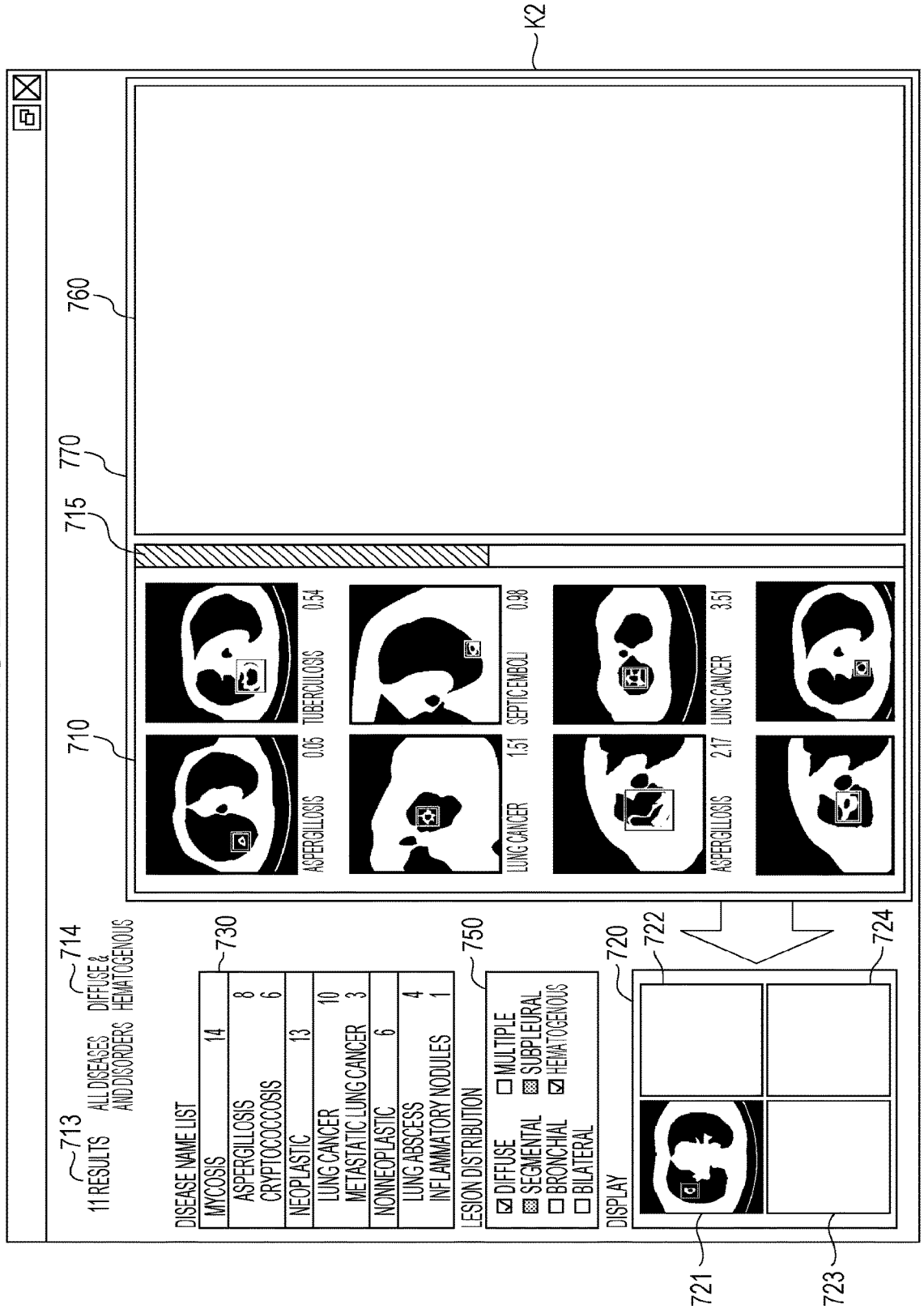
FIG. 27 is a diagram illustrating a basic screen on which refinement is performed by a plurality of lesion distributions.

FIG. 26 is a diagram illustrating a distribution list display area 750 in which a plurality of checkboxes are checked. FIG. 27 is a diagram illustrating a basic screen K2 on which refinement is performed according to a plurality of lesion distributions. In the example illustrated in FIG. 26, the checkboxes for the "diffuse" 751 and the "hematogenous" 757 are checked. Accordingly, as illustrated in FIG. 27, the display control unit 104 displays similar cases having the diffuse and hematogenous lesion distributions in the case display area 710. In the illustrated example, 11 similar cases have the diffuse and hematogenous lesion distributions. Thus, the display control unit 104 displays "11 results" in the number-of-search-result display area 713. The display control unit 104 further displays the disease name(s) to be displayed (here, "all diseases and disorders" since there is no refinement by disease name) and the names of the lesion distributions, i.e., "diffuse & hematogenous" in the display condition display area 714.

FIG. 28 is a diagram illustrating the data configuration of the patient information 1000. The patient information 1000 is accumulated in the patient information accumulation unit 201 on a patient-by-patient basis, and is managed by the patient information management unit 202 of the medical information management system 200. The patient information 1000 has registered therein personal information on each patient, such as gender and age, clinical information such as the past medical history that the patient has, and test information on medical tests that the patient has undergone, such as a blood test. As illustrated in FIG. 28, the patient information 1000 includes a patient ID 1100, a name 1200, an age 1300, a gender 1400, a past medical history 1500, a family history 1600, a chief complaint 1700, test information 1800, and a definite diagnosis 1900.

The patient ID 1100 is an identifier specific to each patient. The name 1200, the age 1300, the gender 1400, the past medical history 1500, the family history 1600, and the chief complaint 1700 are the name, age, gender, past medical history, family history, and chief complaint of the patient identified by the patient ID 1100, respectively. The test information 1800 indicates information concerning one or more medical tests that the patient has already undergone, as illustrated in FIG. 29.

FIG. 29 is a diagram illustrating the data configuration of the test information 1800 registered in the patient information 1000 illustrated in FIG. 28. The test information 1800 is information concerning tests performed on the patient, and a piece of test information is created for each test. The test information 1800 includes a test ID 1810, a test date 1820, a test type 1830, and a test result 1840. The test ID 1810 is an identifier specific to each test. The test date 1820 is the date on which the test was performed. The test type 1830 is the type of the test. Examples of the type of the test include blood tests, respiratory tests, endoscopic examinations, simple X-ray imaging tests, and CT imaging tests.

The test result 1840 includes the values of various indices, such as white blood cell count (or leukocyte count), lactate dehydrogenase (LDH), and glutamic-pyruvic transaminase (GPT) for a blood test. The test result 1840 also includes, for example, a decision made by a radiologist based on various indices. For an imaging test such as a simple X-ray imaging test or a CT imaging test, the test result 1840 includes pointer information on a pointer to a captured image and pointer information on a pointer to a report obtained as a result of image-based diagnosis. Images captured during tests are accumulated in DICOM format in the medical image data accumulation unit 203 of the medical information management system 200.

In a case where the test type 1830 indicates an imaging test such as simple X-ray, CT, MRI, or positron emission tomography (PET)), medical image data obtained through such imaging tests is accumulated in a medical image database 2000 stored in the medical image data accumulation unit 203 of the medical information management system 200.

Figure 30:
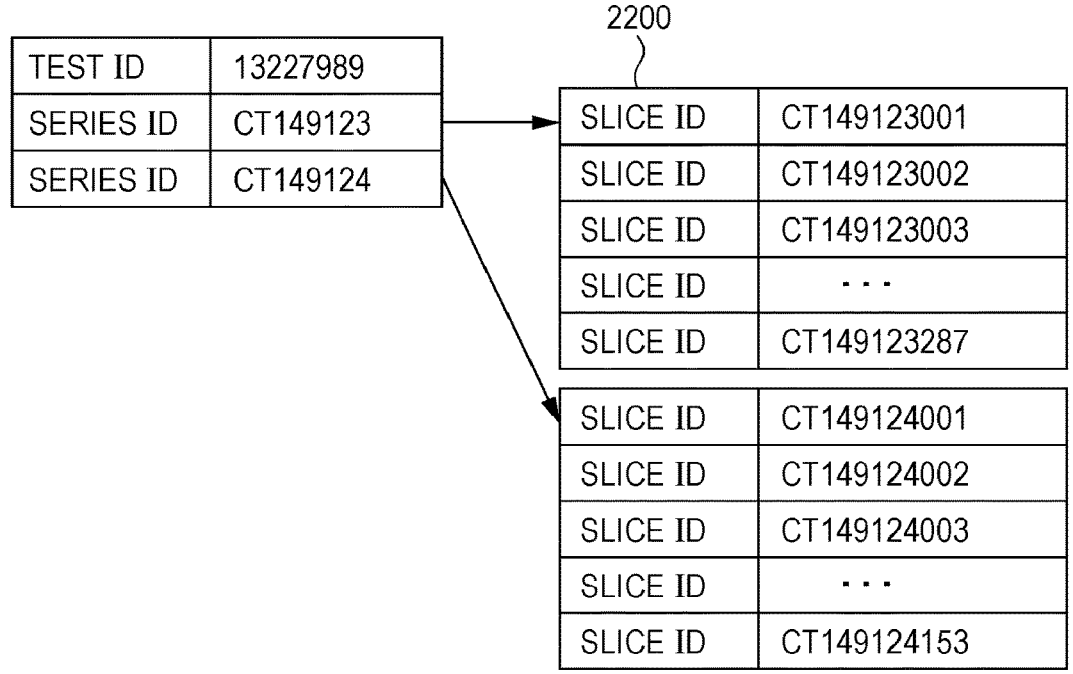
FIG. 30 is a diagram illustrating the data configuration of a medical image database.

FIG. 30 is a diagram illustrating the data configuration of the medical image database 2000. The medical image database 2000 includes a test ID 1810 and a series ID 2100. A plurality of series IDs 2100 may be associated with a single test ID 1810 since a plurality of types of imaging sessions (e.g., simple CT, contrast CT, etc.) may be performed in a single test. That is, a number of series corresponding to the number of types of imaging sessions are obtained.

A series is also obtained for each condition of the reconstruction of captured images, as well as for each type of imaging session. For example, when captured images are reconstructed under the pulmonary condition and the mediastinal condition, one series is obtained for each of these conditions. In images reconstructed under the pulmonary condition, blood vessels in the lungs, bronchi, alveoli, and the like are displayed in a highlighted manner. In images reconstructed under the mediastinal condition, the mediastinal structures, such as blood vessels and lymph nodes, are displayed in a highlighted manner. The pulmonary condition and the mediastinal condition are obtained by the reconstruction of images obtained in single imaging sessions. Thus, two imaging sessions, or simple CT and contrast CT, are performed, and images are reconstructed under the pulmonary condition and the mediastinal condition in each of the two imaging sessions, thereby obtaining two series for the pulmonary condition and two series for the mediastinal condition.

For imaging tests for CT and MRI, a plurality of slice images are obtained in a single imaging session. Thus, a plurality of slice IDs 2200 are associated with one series ID 2100. In FIG. 30, two series IDs "CT149123" and "CT149124" are associated with the test ID "13227989". Thus, it is found that CT images of two series have been obtained through the test. It is also found that a plurality of slice IDs 2200 are associated with each of the series IDs "CT149123" and "CT49124".

In a case where the test type 1830 indicates an imaging test for simple X-ray, CT, MRI, PET, or the like, a diagnostic report 3000 as illustrated in FIG. 31 is accumulated in the diagnostic report management unit 205 of the medical information management system 200. The diagnostic report 3000 has registered therein diagnostic results from a radiologist for each test. FIG. 31 is a diagram illustrating the data configuration of the diagnostic report 3000.

The diagnostic report 3000 includes a test ID 1810, findings 3100, and a diagnosis 3200. The test ID 1810 is the same as the test ID 1810 illustrated in FIG. 29. Accordingly, the diagnostic report 3000 and the test information 1800 are associated with each other. The findings 3100 have registered therein a note indicating a radiologist's findings of the test. The diagnosis 3200 has registered therein a note indicating a radiologists diagnosis for the test.

Figure 32:
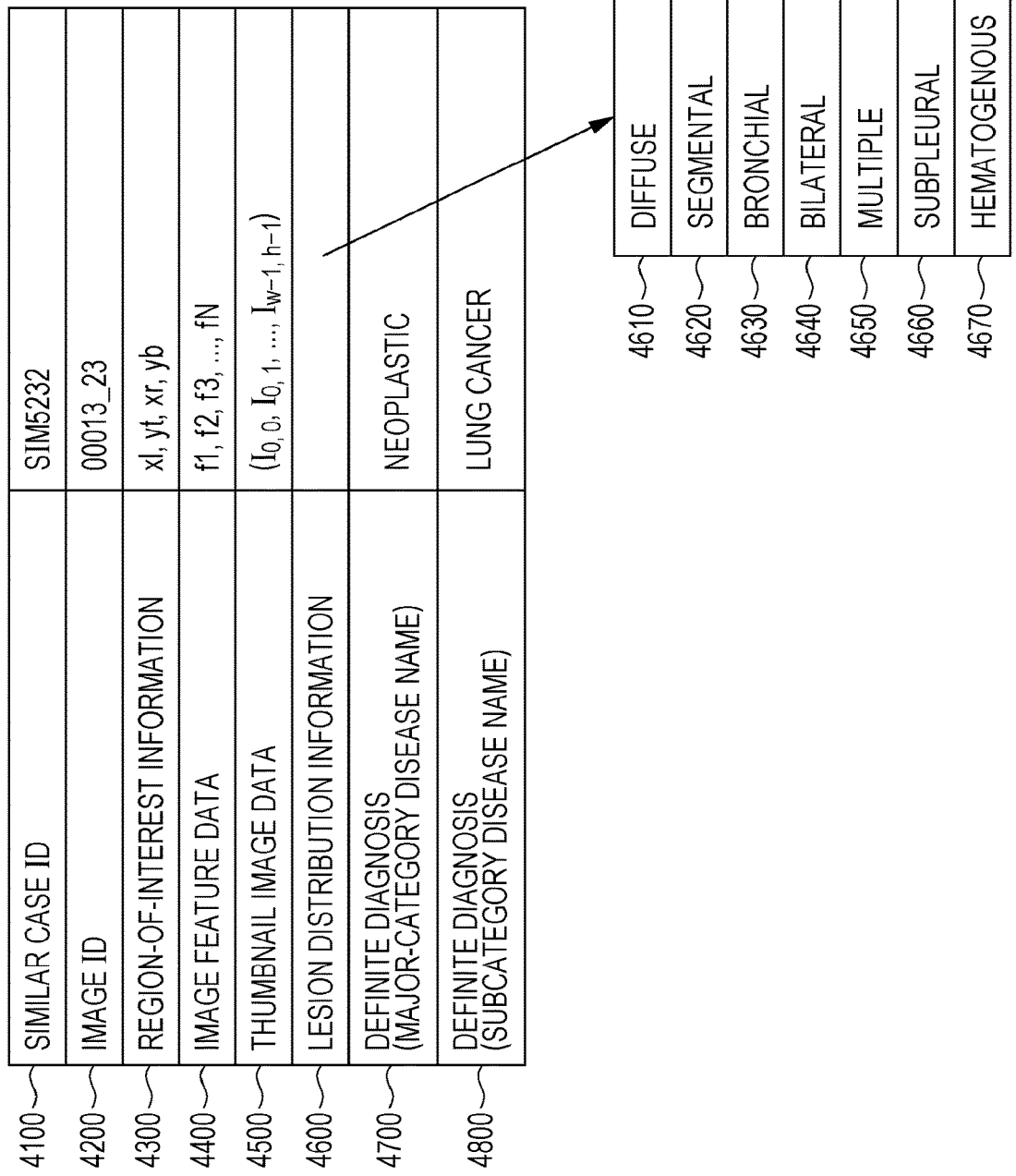
FIG. 32 is a diagram illustrating the data configuration of similar case data.

FIG. 32 is a diagram illustrating the data configuration of the similar case data 4000. The similar case data 4000 is data to be referenced to search for a similar case that is similar to the case to be diagnosed, and a piece of similar case data is created for each similar case. The similar case data 4000 is accumulated for each similar case in the similar case data accumulation unit 301 of the case search system 300. As illustrated in FIG. 32, the similar case data 4000 includes a similar case ID 4100, an image ID 4200, region-of-interest information 4300, image feature data 4400, thumbnail image data 4500, lesion distribution information 4600, a definite diagnosis (major-category disease name) 4700, and a definite diagnosis (subcategory disease name) 4800.

The similar case ID 4100 is an identifier of the similar case data 4000. Since a piece of similar case data is generated for each region of interest set on a slice image of a similar case, the similar case ID 4100 can also be referred to as an identifier of the region of interest. In the example illustrated in FIG. 32, the similar case ID 4100 is constituted by a symbol sequence including "SIM" and a number which follows it.

Figure 33:
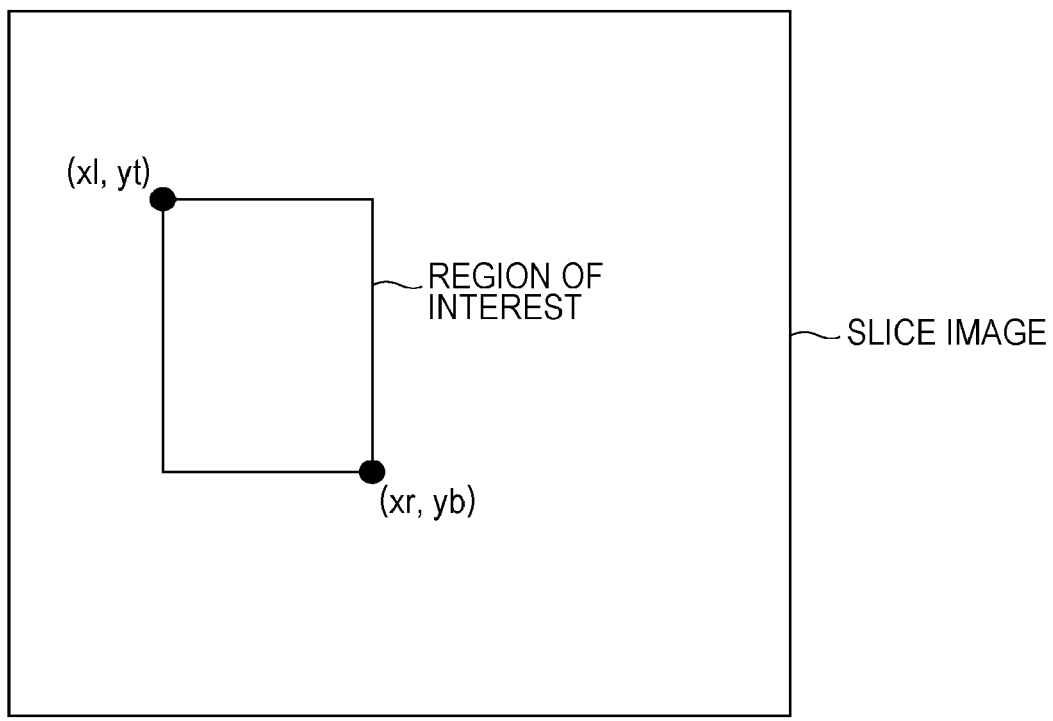
FIG. 33 is a diagram schematically illustrating a region of interest set on a slice image.

The image ID 4200 is an identifier specific to a medical image contained in a medical book on which a region of interest has been set. The image ID 4200 corresponds to the image ID 423 in the medical book image data 420 (FIG. 5). The region-of-interest information 4300 is information indicating the position of the region of interest set on the slice image. FIG. 33 is a diagram schematically illustrating a region of interest set on a slice image. In the example illustrated in FIG. 33, a region of interest is set to have a rectangular shape. Thus, the region-of-interest information 4300 includes four values, namely, the coordinates (xl, yt) of the upper left corner of the region of interest and the coordinates (xr, yb) of the lower right corner of the region of interest. The region of interest may be of any other shape than rectangular, in which case a parameter capable of uniquely identifying the region is used as the region-of-interest information 4300. For example, the region of interest may be circular. In this case, the coordinates of the center of the circular region and the radius of the circular region may be used as the region-of-interest information 4300.

The image feature data 4400 represents certain-number dimensional (here, N-dimensional) feature values extracted from the region of interest defined in the region-of-interest information 4300. The thumbnail image data 4500 is image data of a thumbnail image generated based on a DICOM slice image identified by a slice ID for display in the case display area 710. In the thumbnail image data 4500, for example, pixel values of the thumbnail image are arranged in raster scan order from the upper left corner to the lower right corner of the thumbnail image. As described previously, a DICOM image obtained through a CT test is an 11-bit image having a size of 512 pixels×512 pixels (with a pixel value of −1000 to +1000). In this embodiment, accordingly, to increase the speed of display of a thumbnail image, a DICOM image on which the thumbnail image is based is subjected to a resolution reduction process and a grayscale conversion process to create a thumbnail image with 8-bit pixel values in advance, and the thumbnail image is registered in the similar case data 4000. Thumbnail images may be created by, for example, the medical information management system 200, and transmitted to the case search system 300. Alternatively, thumbnail images may be created by the case search system 300 by obtaining DICOM images from the medical information management system 200.

The lesion distribution information 4600 is a distribution flag value ("1" for Applicable or "0" for Not Applicable) indicating the applicability of the target similar case to each of the predetermined lesion distributions identified by "diffuse" 4610, "segmental" 4620, "bronchial" 4630, "bilateral" 4640, "multiple" 4650, "subpleural" 4660, and "hematogenous" 4670.

The definite diagnosis (major-category disease name) 4700 indicates a disease name classified in a major category (hereinafter referred to as a "major-category disease name") which is definitely diagnosed for the target similar case.

The definite diagnosis (major-category disease name) 4700 is used to refine similar cases by a major-category disease name.

The definite diagnosis (subcategory disease name) 4800 indicates a disease name classified in a subcategory (hereinafter referred to as a "subcategory disease name") which is definitely diagnosed for the target similar case. The definite diagnosis (subcategory disease name) 4800 is used to refine similar cases by a subcategory disease name.

The image ID 423 in the medical book image data 420 (FIG. 5) is searched for using the image ID 4200 as a key. The definite diagnosis (subcategory disease name) 4800 is identified by the definitely diagnosed disease name 424 associated with the image ID 423 found as a result of the search.

In the definite diagnosis (major-category disease name) 4700, a major-category disease name that is uniquely associated with the definite diagnosis (subcategory disease name) 4800 is defined in advance. The definite diagnosis (major-category disease name) 4700 is stored in the similar case data 4000 using the association relationship with the definite diagnosis (subcategory disease name) 4800.

Next, a process flow from the start of image interpretation to the start of a similar case search by using the information terminal 100 in coordination with the medical information management system 200 and the case search system 300 will be described.

Figure 34:
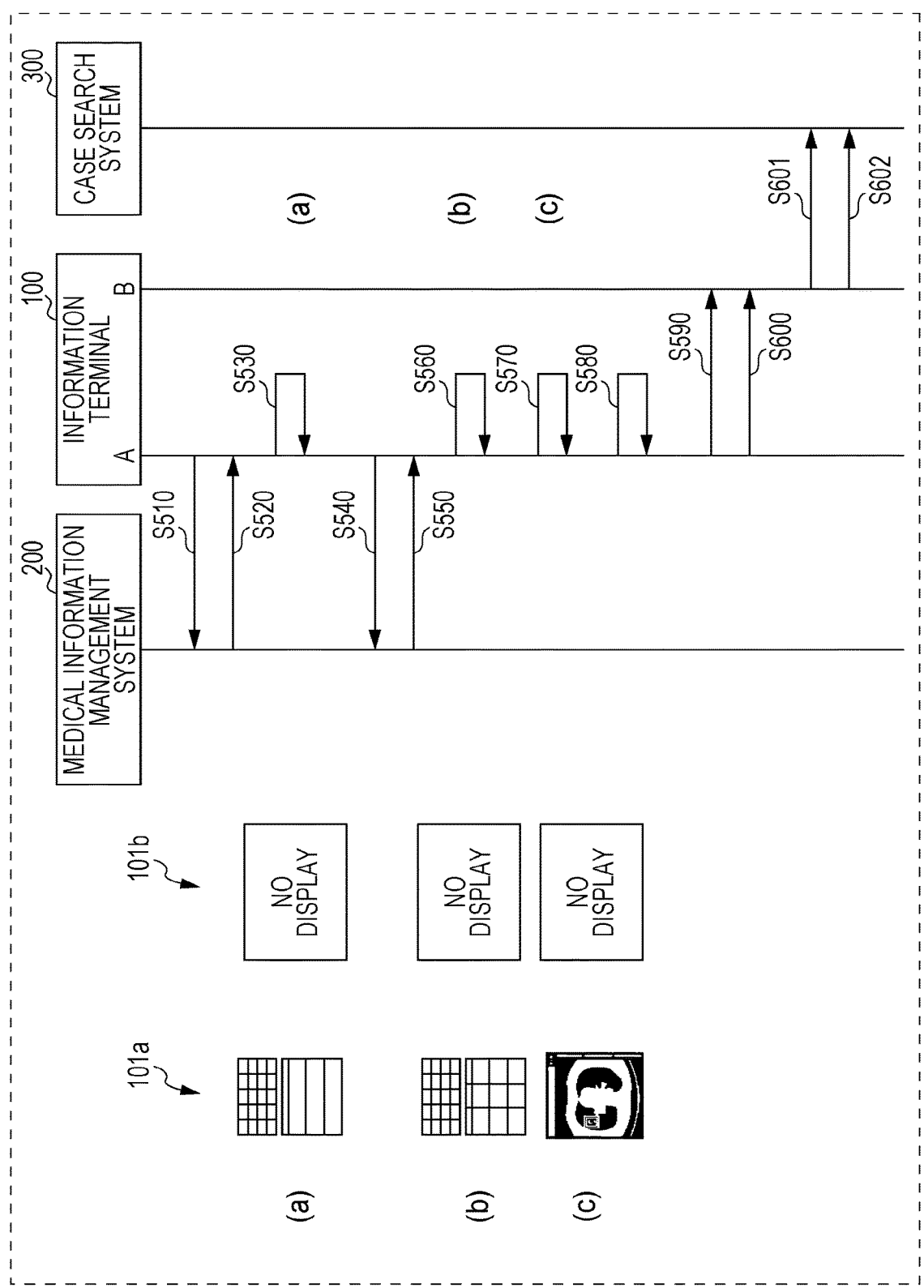
FIG. 34 is a sequence diagram illustrating a process performed until, after obtaining a case to be diagnosed from the medical information management system, the information terminal sends a similar case search request to the case search system and the case search system receives the similar case search request.

FIG. 34 is a sequence diagram illustrating a process performed until, after obtaining a case to be diagnosed from the medical information management system 200, the information terminal 100 sends a similar case search request to the case search system 300 and the case search system 300 receives the similar case search request. In FIG. 34, rectangular objects to the left of the sequence diagram, which are arranged side-by-side in two columns, represent screens displayed on the displays 101*a* and 101*b* through the processes of the respective steps. In FIG. 34, furthermore, in the information terminal 100, "A" represents the medical information management application and "B" represents the similar case search application. It is assumed that the medical information management application is started in advance before the commencement of the above-described sequence.

First, the information terminal 100 accepts a request for displaying a test list in which image interpretation is to be performed by a user (a radiologist who undertakes image interpretation) through the operation unit 102, and transmits the request for displaying the test list to the communication control unit 206 of the medical information management system 200 via the input control unit 103 and the communication control unit 110 (S510).

The patient information management unit 202 of the medical information management system 200 lists tests in which image interpretation has not been completed after the completion of an imaging test to generate a test list in which image interpretation is to be performed. Then, the patient information management unit 202 transmits the generated test list to the communication control unit 110 of the information terminal 100 via the communication control unit 206 (S520). The test list includes the patient information 1000 on the patient, and the test information 1800.

The display control unit 104 of the information terminal 100 displays the test list received by the communication control unit 110 on the display 101 (S530).

In this case, the test list is displayed on the display 101*a*, whereas nothing is displayed on the display 101*b*.

FIG. 35 is a view of a screen for a test list. The test list includes an area 800 where tests in which image interpretation has not been completed are displayed, and an area 810 where information concerning series included in a test is displayed. The area 800 has the following fields: "patient ID", "patient name", "test date", "test ID", and "test type". The "patient ID" and "patient name" fields show the items corresponding to the patient ID 1100 and the name 1200 registered in the patient information 1000, respectively. The "test date", "test ID", and "test type" fields show the items corresponding to the test date 1820, the test ID 1810, and the test type 1830 registered in the test information 1800, respectively. The area 810 is an area for displaying the details of a test selected by the user in the area 800, and has the following fields: "series ID", "definition", and "image". In FIG. 35, no test (corresponding to a row) is selected by the user in the area 800, and thus nothing is displayed in the area 810.

The user selects a test in which image interpretation is about to be performed from among the tests displayed in the area 800. When the selection of the test is detected by the input control unit 103, as illustrated in FIG. 34, the communication control unit 110 transmits a request for displaying all the series included in the test ID of the selected test to the medical information management system 200 (S540).

When the communication control unit 206 of the medical information management system 200 receives the request, the patient information management unit 202 refers to the medical image database 2000 illustrated in FIG. 30 to obtain all the slice images in all the series included in the test ID designated in the request, and transmits the slice images to the information terminal 100 via the communication control unit 206 (S550). For example, in the example illustrated in FIG. 30, when the test with the test ID "13227989" is selected by the user, all the slice images included in the series with the series IDs "CT149123" and "CT149124" are transmitted in S550.

When the communication control unit 110 of the information terminal 100 obtains the images in all the series, the display control unit 104 displays a series list in the area 810 to display information concerning all the series included in the designated test ID in list form (S560).

In this case, the area 810 for a test list, which is displayed on the display 101*a*, shows a list of series corresponding to the test selected in the area 800, whereas nothing is displayed on the display 101*b*.

FIG. 36 is a view of a screen for a test list obtained after a test has been selected. In the area 800 illustrated in FIG. 36, a selected row is highlighted. In the example illustrated in FIG. 36, the test for "John Doe" in the second row is selected in the area 800. Accordingly, the "series ID", "definition", and "image" fields for the selected test are displayed in the area 810. The series IDs associated with the test ID of the selected test in the medical image database 2000 are displayed in the "series ID" field, and thumbnail images of single typical slice images of the displayed series IDs are displayed in the "image" field. Each of the single typical slice images of the series IDs is an image corresponding to a predetermined slice position. The predetermined slice position may be the initial slice position or the center slice position. The "definition" field indicates an imaging condition or a reconstruction condition for the associated series. The content in the "definition" field is registered in association with, for example, a series ID in the medical image database 2000 illustrated in FIG. 30, although not illustrated in the drawings.

Figure 37:
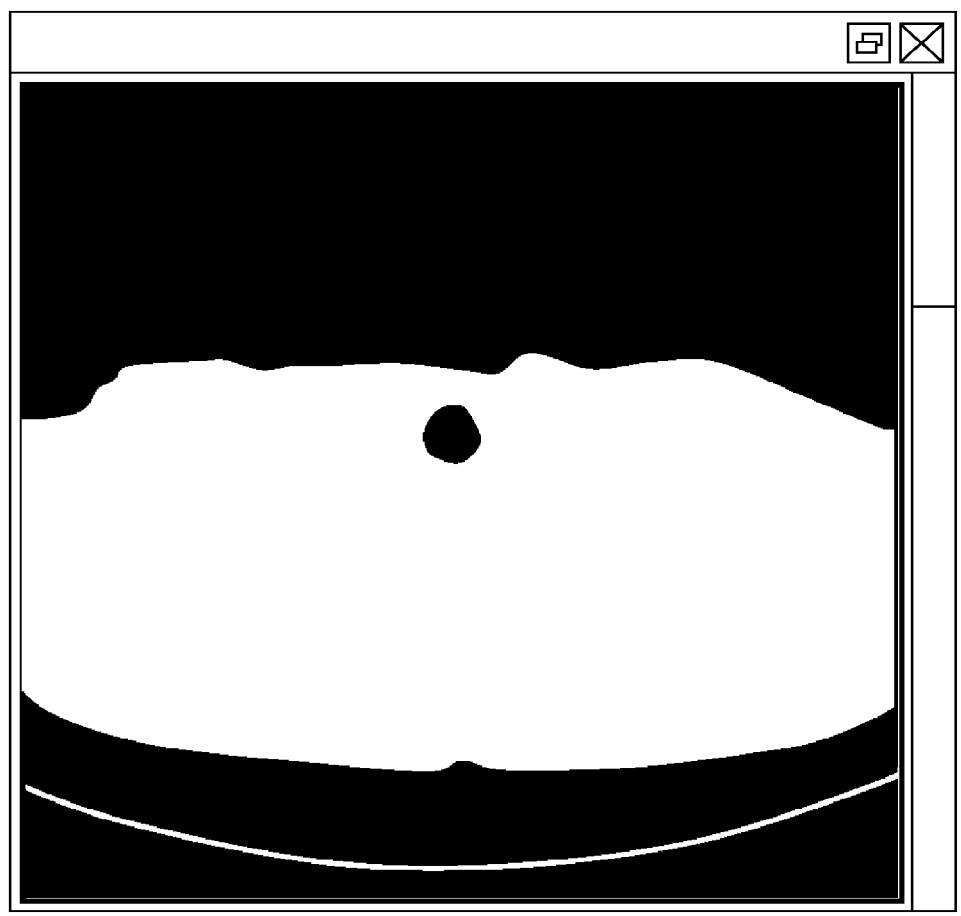
FIG. 37 is a diagram illustrating a slice image displayed on a display when a user selects a series.

When the user selects a series to be subjected to image interpretation in the area 810 and the selection of the series is detected by the input control unit 103, as illustrated in FIG. 37, the display control unit 104 displays the initial slice image in the selected series on the display 101*a* (S570). FIG. 37 is a diagram illustrating a slice image displayed on the display 101*a* when a user selects a series. FIG. 37 is a diagram illustrating the first slice in chest CT imaging, and illustrates a slice image of a shoulder part which is nearer the head than the apex of the lung. The display control unit 104 displays all the slice images in the selected series on the display 101a so that a series-to-series switching operation can be performed. Note that nothing is displayed on the display 101b. For example, the user inputs a slice-to-slice switching operation which involves rotating the mouse wheel while the mouse pointer is on the display 101a, and the input operation is detected by the input control unit 103. Then, the display control unit 104 switches the slice image displayed on the display 101a to a slice image corresponding to another slice position in accordance with the amount of rotation of the mouse wheel. The user performs an image-based diagnosis while inputting a slice-to-slice switching operation. When confused in the image-based diagnosis, the user starts the similar case search application.

The similar case search application may be started in response to the input of a predetermined shortcut key on the keyboard of the operation unit 102 or may be started by specifying a similar case search menu from a medical image viewer menu which is displayed by the right click of the mouse. When an instruction for starting the similar case search application is given, the management of the information terminal 100 is passed to the ROI management unit 105, and the information terminal 100 waits for a region of interest (ROI) to be accepted.

Figure 38:
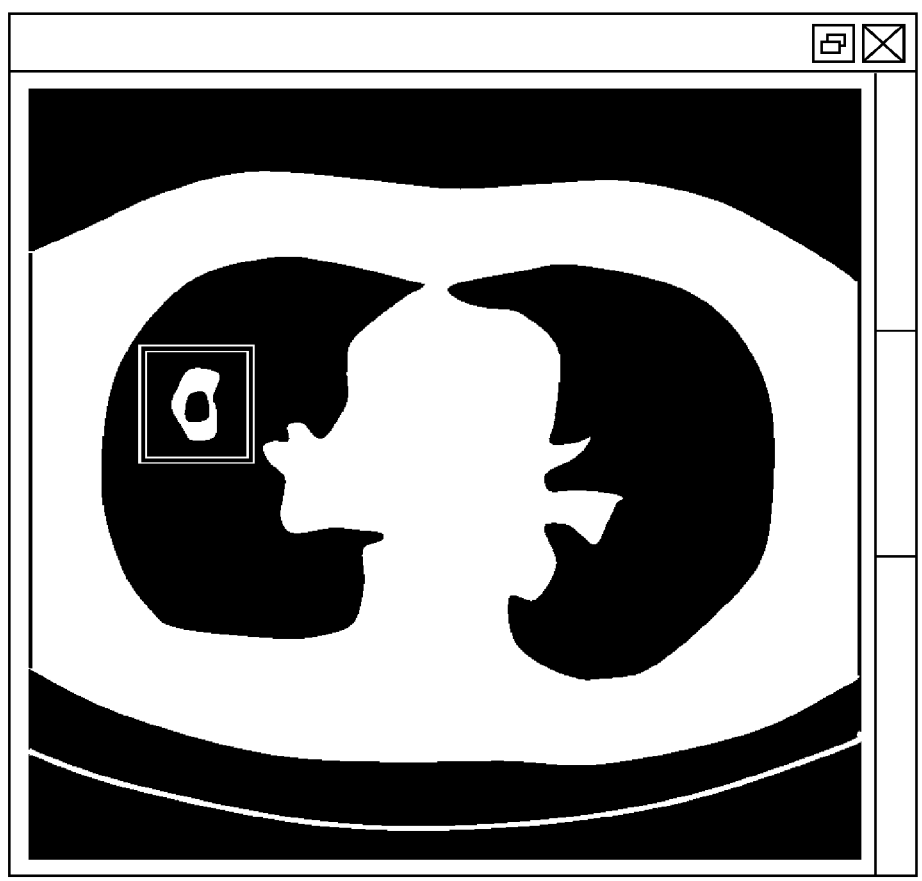
FIG. 38 is an illustration of an example of a screen after a region of interest has been set on a lesion.

The user sets a region of interest (ROI) on a lesion in the slice image displayed on the display 101a through the operation unit 102 (S580). As illustrated in FIG. 33, the user may enter the coordinates of the upper left corner of the region of interest by, for example, left-clicking on the mouse. Then, the user may drag the mouse diagonally down from left to right while left-clicking on the mouse and then release the left click to enter the coordinates of the lower right corner of the region of interest. FIG. 38 illustrates an example of a screen after a region of interest has been set on the lesion.

When the input control unit 103 detects the operation of setting a region of interest, the ROI management unit 105 receives coordinate data of the upper left and lower right corners of the region of interest from the input control unit 103, and generates region-of-interest information by using the received coordinate data.

Then, the ROI management unit 105 transmits the generated region-of-interest information to the communication control unit 110 (S590).

Also, the ROI management unit 105 transmits the slice image of the case to be diagnosed to the communication control unit 110 (S600). In this case, one slice image (i.e., a search query image) in which the user has set a region of interest in the series selected by the user among the slice images in all the series received by the information terminal 100 from the medical information management system 200 in S550 is transmitted.

Then, the communication control unit 110 receives the region-of-interest information transmitted from the ROI management unit 105, and transmits the region-of-interest information to the communication control unit 304 of the case search system 300 (S601).

Also, the communication control unit 110 receives the slice image transmitted from the ROI management unit 105, and transmits the slice image to the communication control unit 304 of the case search system 300 (S602).

In S600 and S601, a slice image itself is transmitted. The slice ID of a slice image may be transmitted instead. In this case, upon receipt of the slice ID, the case search system 300 may obtain a slice image from the medical information management system 200 by specifying the slice ID.

Next, a process performed until the case search system 300 performs a similar case search and the information terminal 100 initially displays a similar case search result will be described.

Figure 39:
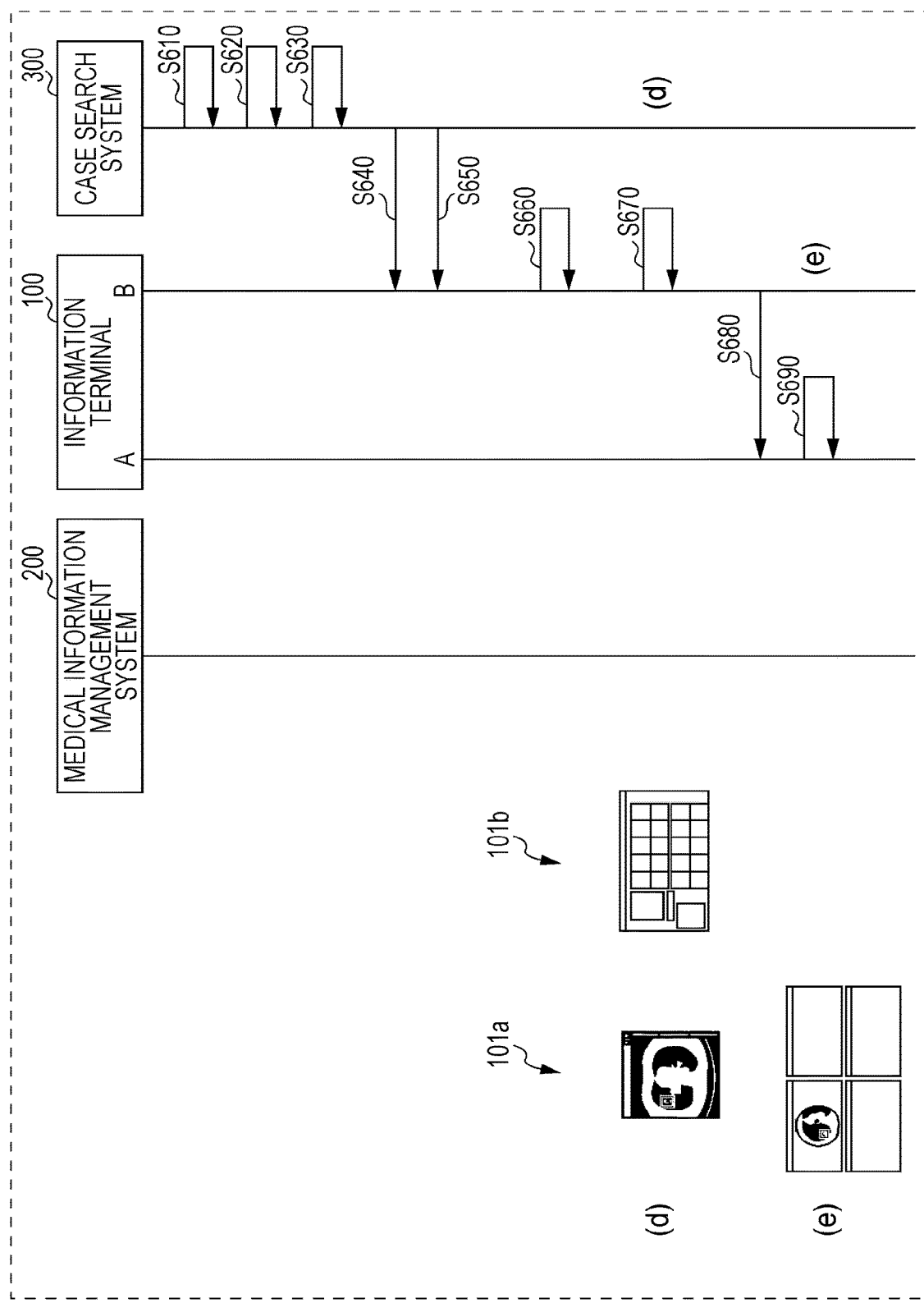
FIG. 39 is a sequence diagram illustrating a process performed until, after receiving a similar case search request, the case search system returns similar case search results to the information terminal.

FIG. 39 is a sequence diagram illustrating a process performed until, after receiving a similar case search request, the case search system 300 returns similar case search results to the information terminal 100.

The image feature extraction unit 302 of the case search system 300 extracts predetermined multi-dimensional image features from the region of interest set on the search query image (S610).

Examples of the "image features" include image features for the shape of organs or lesions in medical images, and image features for a luminance distribution. For example, NEMOTO et al. describes, in "Improvement of Tumor Detection Performance in Mammograms by Feature Selection from a Large Number of Features and Proposal of Fast Feature Selection Method", the transactions of the Institute of Electronics, Information and Communication Engineers D-II, Vol. J88-D-II, No. 2, pp. 416-426, February 2005, the use of 490-dimensional image features. In this embodiment, for example, the image features described in this non-patent literature are used. However, this is merely an example, and other image features may be used.

The similar case search unit 303 compares the image features extracted by the image feature extraction unit 302 with image features in each of the similar cases accumulated in the similar case data accumulation unit 301 (S620). The similar case search unit 303 compares both image features by calculating a distance between image feature data extracted from the search query image and the image feature data 4400 registered in the similar case data 4000 (FIG. 32) accumulated for each similar case in the similar case data accumulation unit 301.

Then, the similar case search unit 303 determines, as a similar case to be transmitted, a similar case for which the distance is less than or equal to a predetermined threshold value by sorting similar cases in order of increasing distance (S630). Then, the communication control unit 304 transmits items within the similar case data 4000 accumulated in the similar case data accumulation unit 301, namely, the similar case ID 4100 of the similar case determined to be transmitted, the image ID 4200, the region-of-interest information 4300, the thumbnail image data 4500, the lesion distribution information 4600, the definite diagnosis (major-category disease name) 4700, and the definite diagnosis (subcategory disease name) 4800, and further the distance calculated by the similar case search unit 303 to the information terminal 100 (S640).

Subsequently, a process for generating the initial basic screen K2 (FIG. 9) on which similar case search results are displayed is executed. First, management information used to generate the layout area 720 on the initial basic screen K2 will be described.

First, the communication control unit 304 of the case search system 300 transmits layout information to the information terminal 100 (S650). The layout information is information which specifies the numbers of rows and columns of display boxes in the layout area 720.

Then, when the communication control unit 110 of the information terminal 100 receives the layout information, the display box management unit 106 registers the numbers of rows and columns of display boxes, which are specified in the transmitted layout information, in the display box management information 4410 (FIG. 40), and also registers the slice ID of the search query image in the display box management information 4410 (FIG. 40) (S660).

FIG. 40 is a diagram illustrating the data configuration of the display box management information 4410. The display box management information 4410 includes a table 4411 in which the number of rows and the number of columns are registered, and a table 4412 in which the slice ID of a slice image to be displayed in each display box is registered. Accordingly, the display box management unit 106 registers the number of rows and the number of columns, which are specified in the layout information transmitted from the case search system 300, in a number-of-row field and a number-of-column field of the table 4411. In this embodiment, the thumbnail image of the search query image is displayed in the upper left display box 721 among the four display boxes 721 to 724. The display box management unit 106 registers the slice ID of the search query image transmitted from the medical information management system 200 in the "first row and first column" item of the table 4412.

The default values of the numbers of rows and columns of display boxes in the layout area 720 are set in advance by the case search system 300. For example, the default values of the number of rows and the number of columns are two and two, respectively. Thus, "two rows and two columns" is registered in the display box management information 4410 illustrated in FIG. 40.

Then, the display control unit 104 generates an initial basic screen K2 on which similar case search results are displayed, by using the similar case data transmitted in S640 and the display box management information 4410 stored in S660 (S670).

In this case, the basic screen K2 illustrated in FIG. 9 is displayed on the display 101*b*. Further, the search query image is displayed on the display 101*a*.

Figure 41:
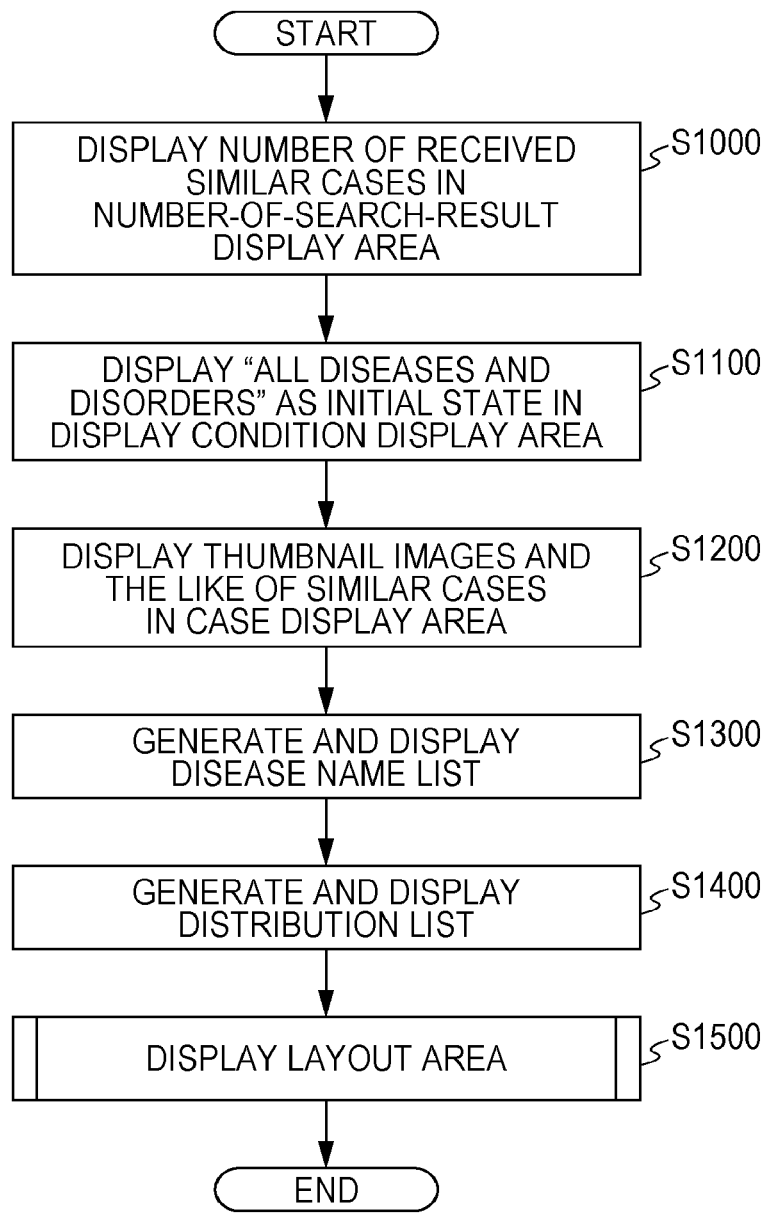
FIG. 41 is a flowchart illustrating the details of a process for generating an initial basic screen in S670 in FIG. 39.

FIG. 41 is a flowchart illustrating the details of the process for generating an initial basic screen K2 in S670 in FIG. 39.

First, in S1000, the display control unit 104 counts the number of similar cases received in S640 in FIG. 39, and displays the count value in the number-of-search-result display area 713.

Then, in S1100, the display control unit 104 displays "all diseases and disorders" in the display condition display area 714. Here, "all diseases and disorders" is displayed because no refinement is performed according to a disease name or a lesion distribution by the user on the initial basic screen K2.

Then, in S1200, the display control unit 104 displays, in the case display area 710, thumbnail images of similar cases, the number of which is equal to the number of similar cases whose thumbnail images can be displayed in the case display area 710, among the similar cases received in S640 in FIG. 39, and also displays definite diagnoses and similarities in association with the respective thumbnail images.

In the example illustrated in FIG. 9, the maximum number of similar cases that can be displayed in the case display area 710 is eight. The maximum value is determined in advance. The maximum value may be changed by the user as desired. If the number of similar cases received in S640 in FIG. 39 is larger than the maximum value, the display control unit 104 displays the scrollbar 715, which is vertically long, at the right end of the case display area 710. By moving the scrollbar 715, the user is able to view the thumbnail images of similar cases that are not currently visible on the initial basic screen K2.

Then, in S1300, a disease name list is generated and displayed. First, a disease name list is generated based on the similar cases received in S640 in FIG. 39. The disease name list is a list of definitely diagnosed disease names into which the similar cases received in S640 are classified.

Here, the number of similar cases received in S640 is represented by NC.

The disease name list management unit 108 generates a disease name list by using the definite diagnosis (major-category disease name) 4700 and the definite diagnosis (subcategory disease name) 4800 registered in each of the NC pieces of similar case data 4000. The generated disease name list is managed by the disease name list management unit 108 as data in table format, as illustrated in FIG. 42.

FIG. 42 is a diagram illustrating the data configuration of the disease name list generated in S1300 in FIG. 41. The disease name list includes the following fields: "disease name ID", "major-category disease name", "subcategory disease name", "number of results", and "similar case ID". The "disease name ID" field shows an identifier assigned to each definitely diagnosed disease name. Here, a single disease name ID is assigned to a combination of major-category and subcategory disease names.

The "major-category disease name" field shows a definitely diagnosed disease name indicated by the definite diagnosis (major-category disease name) 4700 registered in the similar case data 4000. The "subcategory disease name" field shows a definitely diagnosed disease name indicated by the definite diagnosis (subcategory disease name) 4800 registered in the similar case data 4000. The "number of results" field shows the number of similar cases of the disease indicated by the definitely diagnosed disease name identified by the "disease name ID". The "similar case ID" field shows a similar case ID that identifies a similar case of the disease indicated by the disease name identified by the "disease name ID".

The disease name list management unit 108 extracts the definite diagnosis (major-category disease name) 4700 and the definite diagnosis (subcategory disease name) 4800 in each of the pieces of similar case data 4000 received in S640, and classifies pieces of similar case data 4000 having the same definite diagnosis (major-category disease name) 4700 and the same definite diagnosis (subcategory disease name) 4800 as pieces of similar case data indicating similar cases of the same definitely diagnosed disease name. Further, the disease name list management unit 108 counts the number of similar cases of the same definitely diagnosed disease name, and registers the number of similar cases in the "number of results" field of the record of the corresponding definitely diagnosed disease name. The disease name list management unit 108 also registers the similar case IDs of the similar cases classified as the same definitely diagnosed disease name in the "similar case ID" field of the record of the corresponding definitely diagnosed disease name.

In the example illustrated in FIG. 42, the disease name ID "DIS528" is assigned to a definitely diagnosed disease name having the major-category disease name "neoplastic" and the subcategory disease name "lung cancer". The number of similar cases of the disease indicated by the definitely diagnosed disease name is ten. Thus, "10" is registered in the "number of results" field of the corresponding record, and the similar case IDs "SIM258", "SIM551", "SIM1209", "SIM2341", etc. of the similar cases of the disease indicated by the definitely diagnosed disease name are registered in the "similar case ID" field of the corresponding record.

The display control unit 104 generates the disease name list display area 730 by using the disease name list generated in the way described above, and displays the disease name list display area 730 on the display 101.

FIG. 43, FIG. 44, and FIG. 45 are diagrams illustrating a first example display, a second example display, and a third example display of the disease name list display area 730, respectively. In the first example display, as illustrated in FIG. 43, subcategory disease names are displayed in list form in association with the numbers of similar cases thereof, which are obtained as a result of the similar case search, according to the decreasing number of similar cases.

In the second example display, as illustrated in FIG. 44, major-category disease names are displayed in list form in association with the numbers of similar cases thereof, which are obtained as a result of the similar case search, according to the decreasing number of similar cases.

In the third example display, as illustrated in FIG. 45, major-category disease names are displayed in list form in association with the numbers of similar cases thereof, which are obtained as a result of the similar case search, according to the decreasing number of similar cases, and subcategory disease names included in each of the major-category disease names are further displayed in list form in association with the numbers of similar cases thereof according to the decreasing number of similar cases. In this case, each definitely diagnosed disease name is expressed using a hierarchical structure of a major-category disease name and a subcategory disease name.

Figure 46:
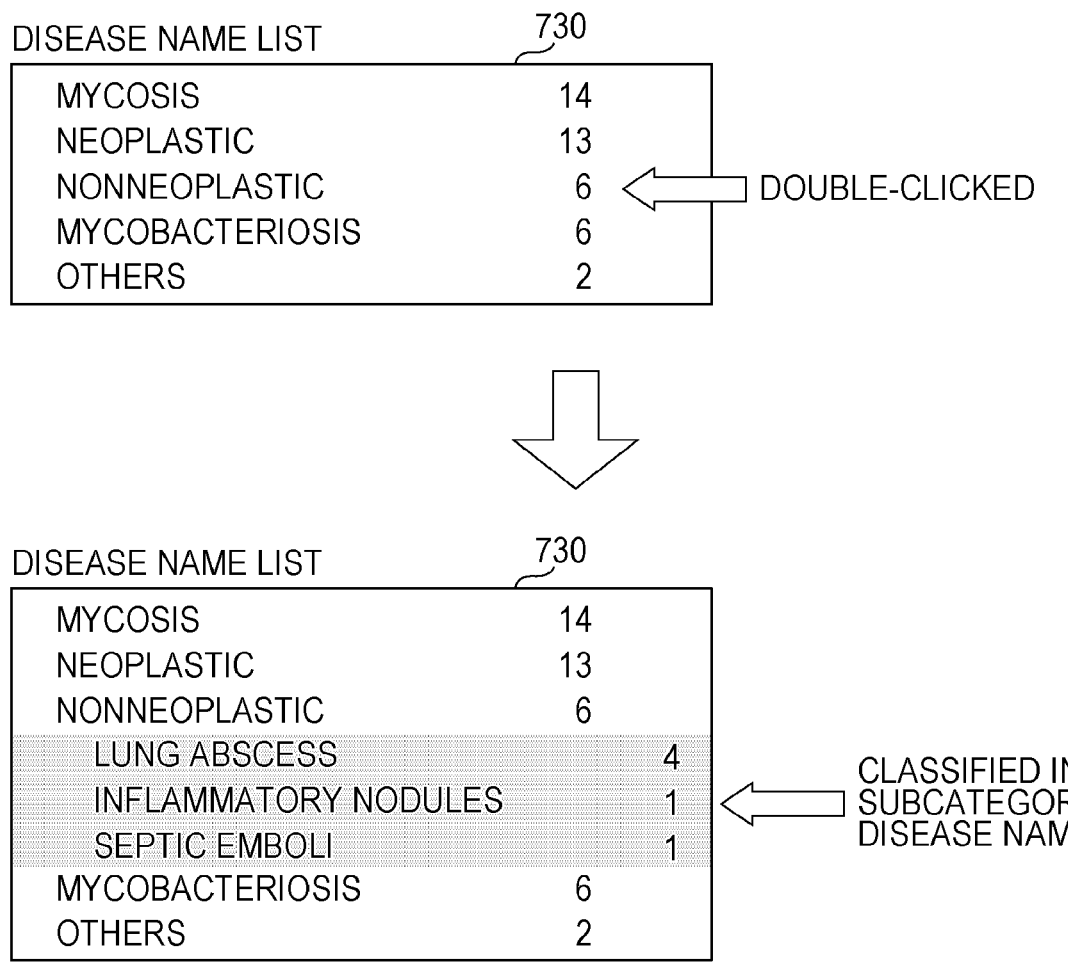
FIG. 46 is a diagram illustrating a screen transition in the disease name list display area illustrated in FIG. 44.

FIG. 46 is a diagram illustrating a screen transition in the disease name list display area 730 illustrated in FIG. 44. As illustrated in the upper part of FIG. 46, when the input control unit 103 detects the selection of a major-category disease name by a user among the major-category disease names displayed in list form, as illustrated in the lower part of FIG. 46, the display control unit 104 displays the subcategory disease names belonging to the selected major-category disease name in association with the numbers of similar cases thereof according to the decreasing number of similar cases. In this case, the user may select a desired major-category disease name from among, for example, the major-category disease names displayed in list form in the disease name list display area 730 by, for example, double clicking or single clicking. In the example illustrated in FIG. 46, the item related to nonneoplastic diseases is double-clicked. Thus, the names of subcategory diseases belonging to the nonneoplastic diseases are displayed in list form.

In the lower part of FIG. 46, when an area displaying a list of subcategory disease names is double-clicked or single-clicked by the user, the display control unit 104 may hide the display of the subcategory disease names in the area.

The display control unit 104 may determine subcategory disease names belonging to a major-category disease name by referring to the disease name list (FIG. 42). For example, in the example illustrated in FIG. 42, aspergillosis and cryptococcosis are associated with mycosis. Thus, the display control unit 104 may determine that aspergillosis and cryptococcosis belong to mycoses.

Referring back to FIG. 41, in S1400, a distribution list is generated and displayed. First, a distribution list is generated based on the similar cases received in S640. The distribution list is a list of lesion distributions into which the similar cases received in S640 are classified.

The disease name list management unit 108 generates a distribution list by using the lesion distribution information 4600 registered in each of the NC pieces of similar case data 4000. The generated distribution list is managed by the distribution list management unit 109 as data in table format, as illustrated in FIG. 47.

FIG. 47 is a diagram illustrating the data configuration of the distribution list generated in S1400 in FIG. 41. The distribution list includes the following fields: "name of distribution", "number of cases", and "similar case ID". The "name of distribution" field shows the names of a plurality of predetermined lesion distributions such as diffuse and segmental. The "number of cases" field shows the number of similar cases corresponding to each lesion distribution. The "similar case ID" field shows a similar case ID that identifies a similar case corresponding to each lesion distribution.

The distribution list management unit 109 extracts the lesion distribution information 4600 in each of the pieces of similar case data 4000 received in S640, counts the number of similar cases corresponding to each of the lesion distributions with the distribution flag value set to "1" (Applicable) in the extracted lesion distribution information 4600, and registers the count value in the "number of cases" field of the record of the corresponding lesion distribution. The distribution list management unit 109 also registers the similar case IDs of similar cases corresponding to each of the lesion distributions with the distribution flag value set to "1" in the "similar case ID" field of the record of the corresponding lesion distribution.

In the example illustrated in FIG. 47, the number of similar cases corresponding to the diffuse lesion distribution is three. Thus, "3" is registered in the "number of cases" field of the record of the diffuse lesion distribution. Further, the similar case IDs "SIM2521", "SIM4123", and "SIM5225" of the similar cases corresponding to the diffuse lesion distribution are registered in the "similar case ID" field of the record of the diffuse lesion distribution.

The display control unit 104 generates the distribution list display area 750 by using the distribution list generated in the way described above, and displays the distribution list on the display 101.

The distribution list display area 750 generated using the distribution list illustrated in FIG. 47 is illustrated in FIG. 23. In FIG. 47, the number of cases corresponding to the segmental lesion distribution is zero and the number of cases corresponding to the subpleural lesion distribution is zero. Thus, in FIG. 23, the "segmental" 752 and the "subpleural" 756 are displayed as inactive, and the other lesion distributions are displayed as active since the numbers of cases corresponding to such lesion distributions are each greater than or equal to one.

Referring back to FIG. 41, in S1500, the layout area 720 is displayed. This process is performed by the display control unit 104.

Figure 48:
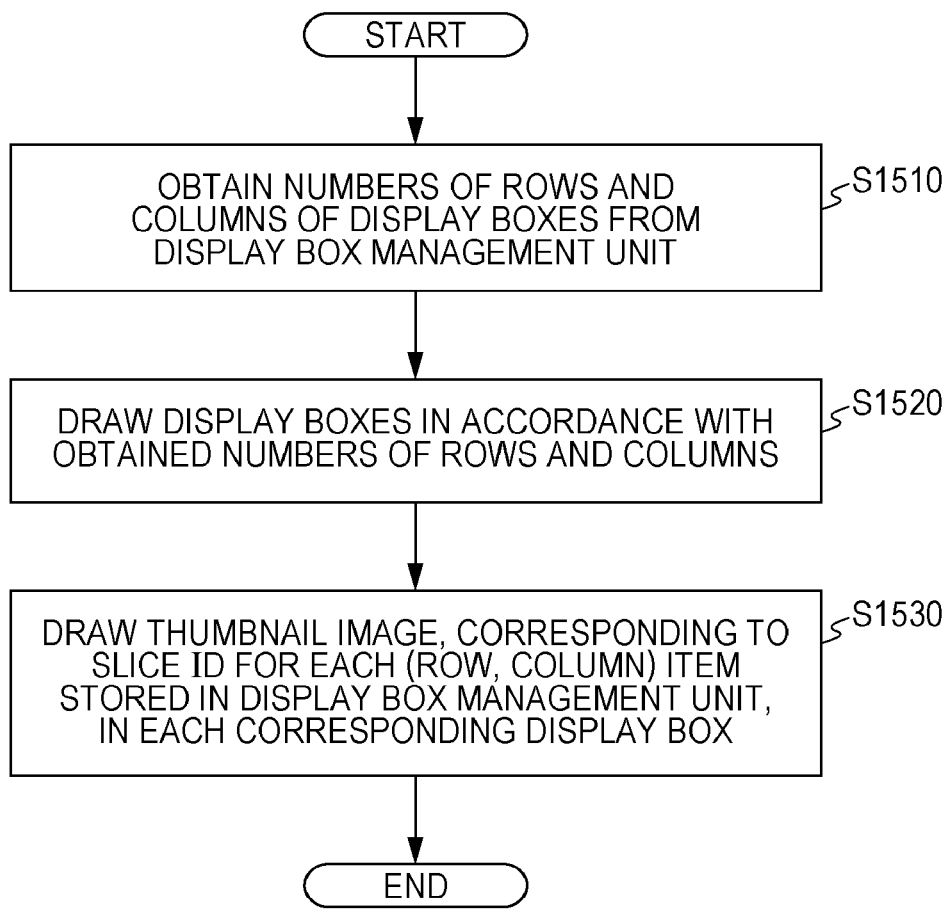
FIG. 48 is a flowchart illustrating the process of S1500 illustrated in FIG. 41.

FIG. 48 is a flowchart illustrating the process of S1500 illustrated in FIG. 41. In S1510, the display control unit 104 obtains the numbers of rows and columns of display boxes in the layout area 720 on the basis of the display box management information 4410 set in S660. In the example of the display box management information 4410 illustrated in FIG. 40, the number of rows and the number of columns are set to two and two, respectively. Thus, information indicating "two rows and two columns" is obtained.

Then, in S1520, the display control unit 104 draws display boxes in accordance with the numbers of rows and columns of display boxes obtained in S1510.

Finally, in S1530, the display control unit 104 identifies a slice ID for each display box from the display box management information 4410, and draws a thumbnail image corresponding to the identified slice ID in the corresponding one of the display boxes.

In the example illustrated in FIG. 40, the slice ID of the case to be diagnosed is stored in the display box at the first row and the first column. Accordingly, the display control unit 104 generates a thumbnail image from the slice image of the case to be diagnosed, which is transmitted in S600 in FIG. 34, and draws the generated thumbnail image in the display box 721.

In this stage, no slice IDs are stored in the other display boxes (i.e., the display boxes 722, 723, and 724 at the first row and the second column, the second row and the first column, and the second row and the second column, respectively). Thus, the display control unit 104 displays no images in these display boxes. Thumbnail images of similar cases are displayed in these display boxes through a process described below.

Referring back to FIG. 39, the communication control unit 110 transmits the display box management information 4410 stored in the display box management unit 106 to the display control unit 104 (S680).

Then, the display control unit 104 activates a medical image viewer in the same display state and layout as the display state and layout of the layout area 720 (S690).

Figure 49:
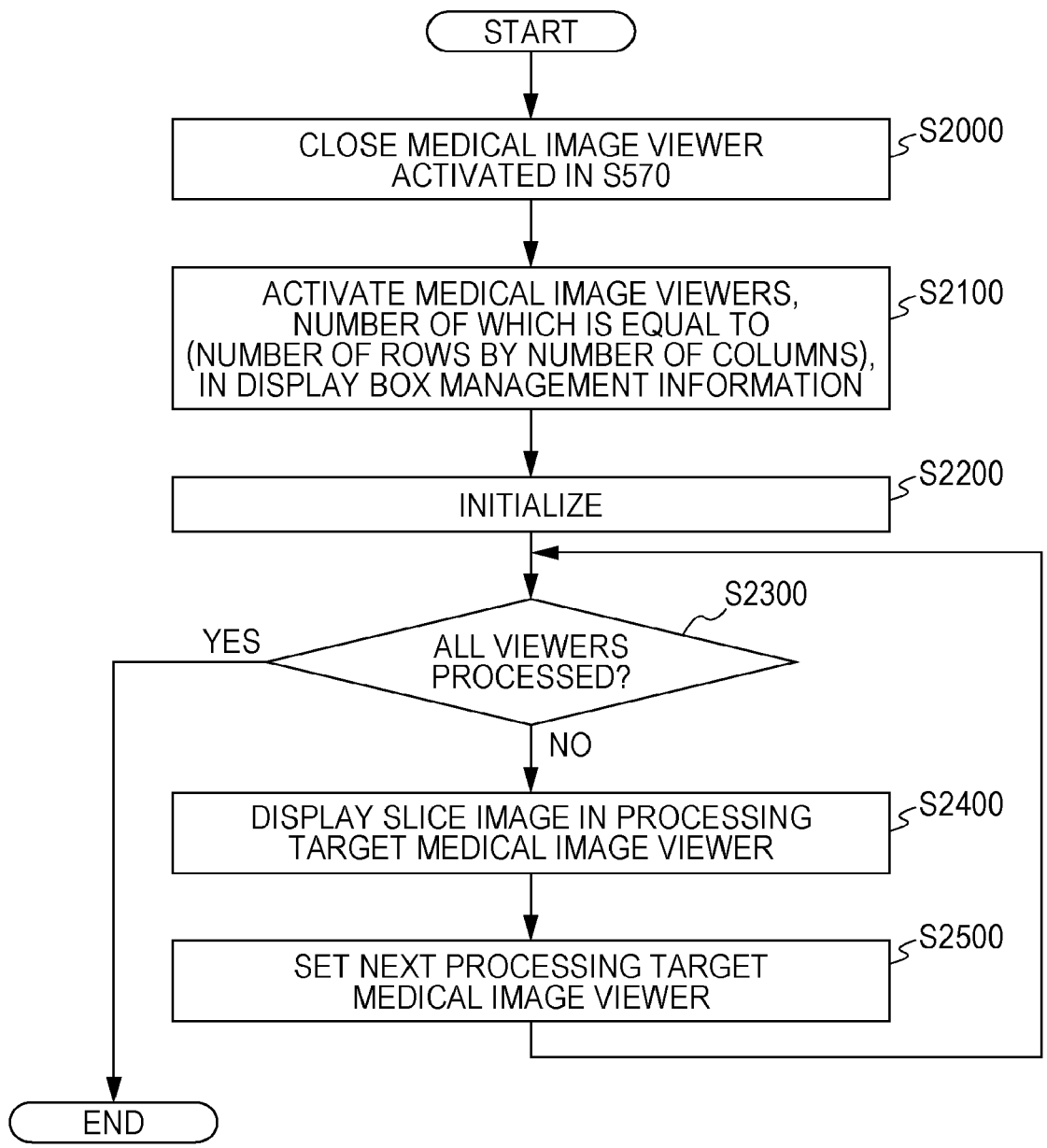
FIG. 49 is a flowchart illustrating a medical image viewer activation process.

FIG. 49 is a flowchart illustrating a medical image viewer activation process.

In S2000, the display control unit 104 closes the medical image viewer activated in S570 in FIG. 34.

In S2100, the display control unit 104 activates medical image viewers corresponding to the display boxes registered in the display box management information 4410, with the layout having the number of rows and the number of columns which are registered in the display box management information 4410. In the display box management information 4410 illustrated in FIG. 40, two rows and two columns of display boxes, that is, four display boxes, are registered. Thus, as illustrated in FIG. 8, the display control unit 104 activates the four medical image viewers 610 to 640 so that the medical image viewers 610 to 640 are arranged in two rows and two columns.

In S2200, the display control unit 104 initializes a variable for identifying a target medical image viewer to be processed. Here, the medical image viewer at the first row and the first column is a target to be processed. Thus, the variable is set to "1" for the number of the row and "1" for the number of the column.

In S2300, the display control unit 104 checks whether or not the process for all (here, four) medical image viewers has been completed. If the process has been completed (YES in S2300), the process ends. If there is any medical image viewer yet to be processed (NO in S2300), the process proceeds to S2400.

In S2400, the display control unit 104 displays a slice image having the slice ID associated with the number of the row and the number of the column which are set as variables in the processing target medical image viewer, and associates the series including the slice ID with the processing target medical image viewer.

For example, in the example of the display box management information 4410 illustrated in FIG. 40, the slice ID "CT12353515" is registered for the position on the first row and the first column. Thus, a slice image with the slice ID "CT12353515" is displayed in the medical image viewer 610. Further, the display control unit 104 draws a rectangular region indicating a region of interest set on the initially displayed slice image so that the rectangular region overlaps the slice image. The series including the slice ID registered for the position on the first row and the first column has already been obtained in S550 in FIG. 34. In addition, the region of interest has already been set in S580 in FIG. 34.

Referring back to FIG. 49, in S2500, the subsequent medical image viewer is set as the processing target medical image viewer. The processing target is set in such a manner that the medical image viewer at the first row and the first column is followed by, for example, the medical image viewer at the first row and the second column, the medical image viewer at the second row and the first column, and the medical image viewer at the second row and the second column in this order.

In the second loop, in S2400, the medical image viewer 620 at the first row and the second column is set as the processing target. In the display box management information 4410 illustrated in FIG. 40, no slice IDs are associated with the medical image viewers other than the medical image viewer at the first row and the first column. Thus, the display control unit 104 performs no processes on the medical image viewer 620 at the first row and the second column and makes it blank. The same applies to the medical image viewer 630 at the second row and the first column and the medical image viewer 640 at the second row and the second column.

When the process illustrated in the flowchart is completed, the initial basic screen K1 illustrated in FIG. 8 is being displayed on the display 101a. The search query image is displayed in the (upper left) medical image viewer 610 at the first row and the first column, and the region of interest is further drawn so as to overlap the search query image.

Figure 50:
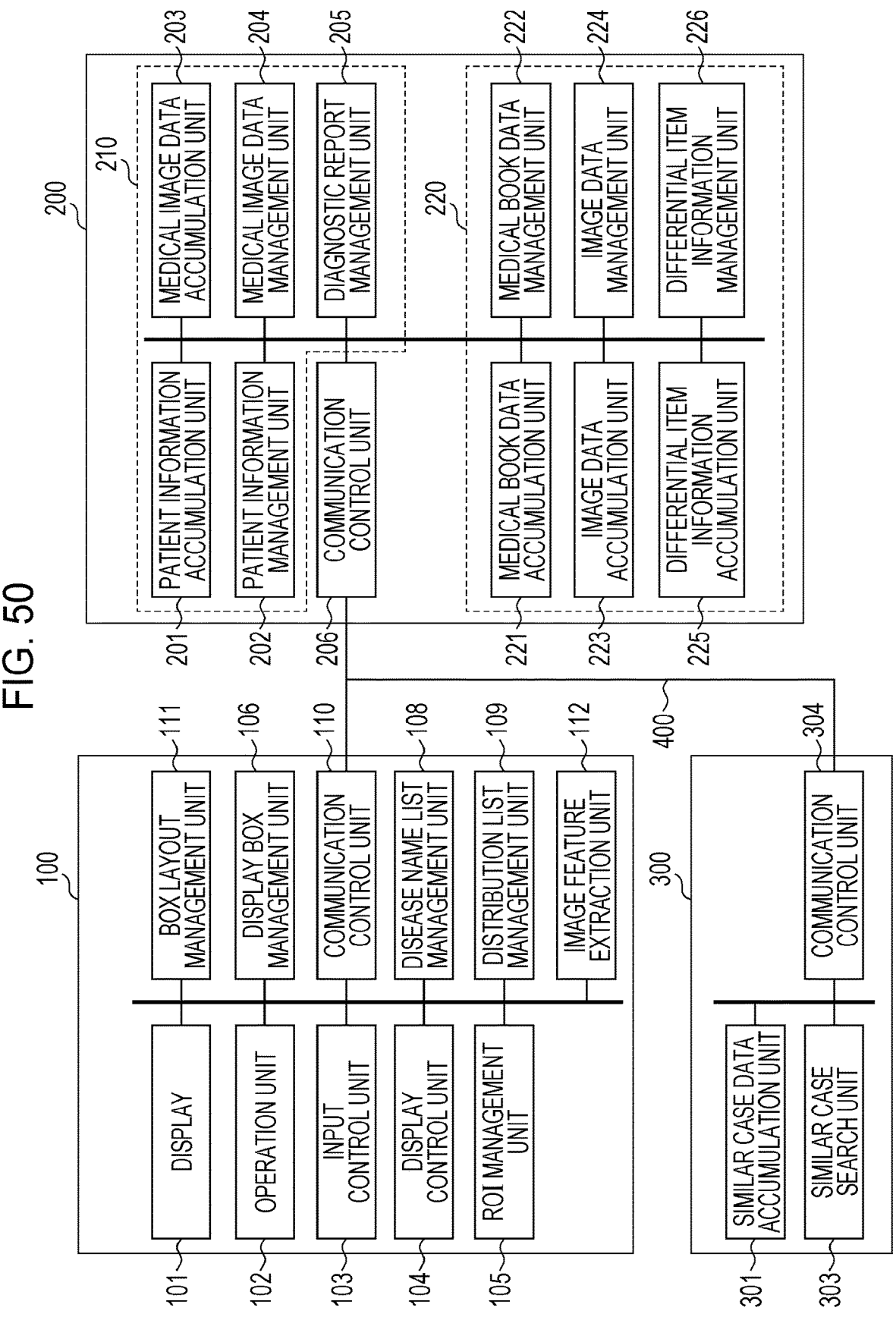
FIG. 50 is a block diagram of an information terminal, a medical information management system, and a case search system in an embodiment in which the case search system extracts an image feature.

In the illustrated example, the case search system 300 extracts an image feature. Alternatively, the information terminal 100 may extract an image feature. FIG. 50 is a block diagram of the information terminal 100, the medical information management system 200, and the case search system 300 in an embodiment in which the case search system 300 extracts an image feature.

The difference from FIG. 2 is that the information terminal 100 further includes an image feature extraction unit 112 and the case search system 300 does not include the image feature extraction unit 302.

Figure 51:
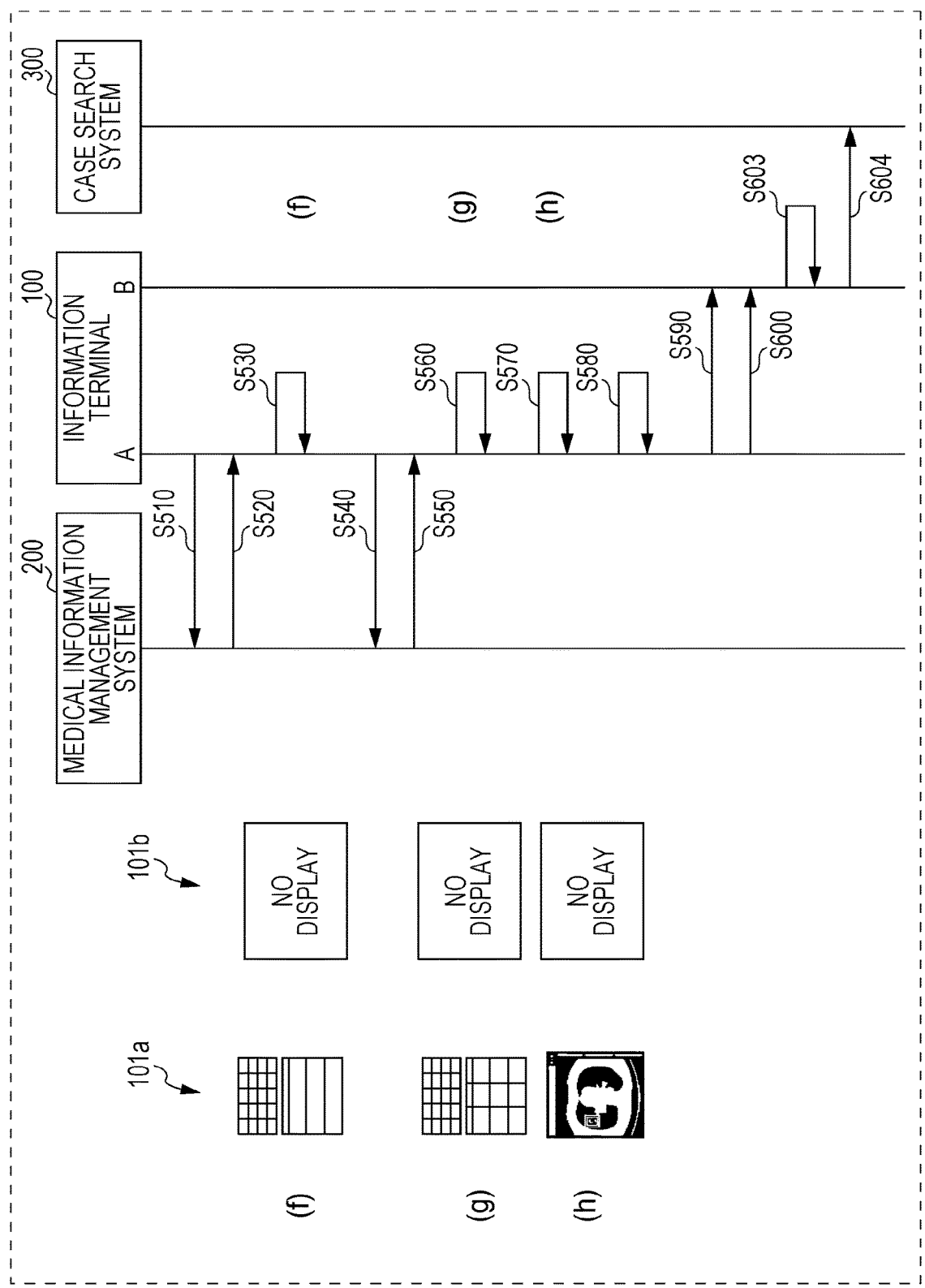
FIG. 51 is sequence diagram illustrating a process performed until, after the information terminal obtains a case to be diagnosed from the medical information management system, the case search system receives a similar case search request.

FIG. 51 is a sequence diagram illustrating a process performed until, after the information terminal 100 obtains a case to be diagnosed from the medical information management system 200, the case search system 300 receives a similar case search request.

The difference from FIG. 34 is that, after the ROI management unit 105 performs a process of transmitting a slice image of the case to be diagnosed to the communication control unit 110 (S600), the information terminal 100 extracts an image feature (S603) and transmits the extracted image feature to the case search system 300 (S604). The process for extracting an image feature (S603) is similar to that in the case where the case search system 300 extracts an image feature.

Figure 52:
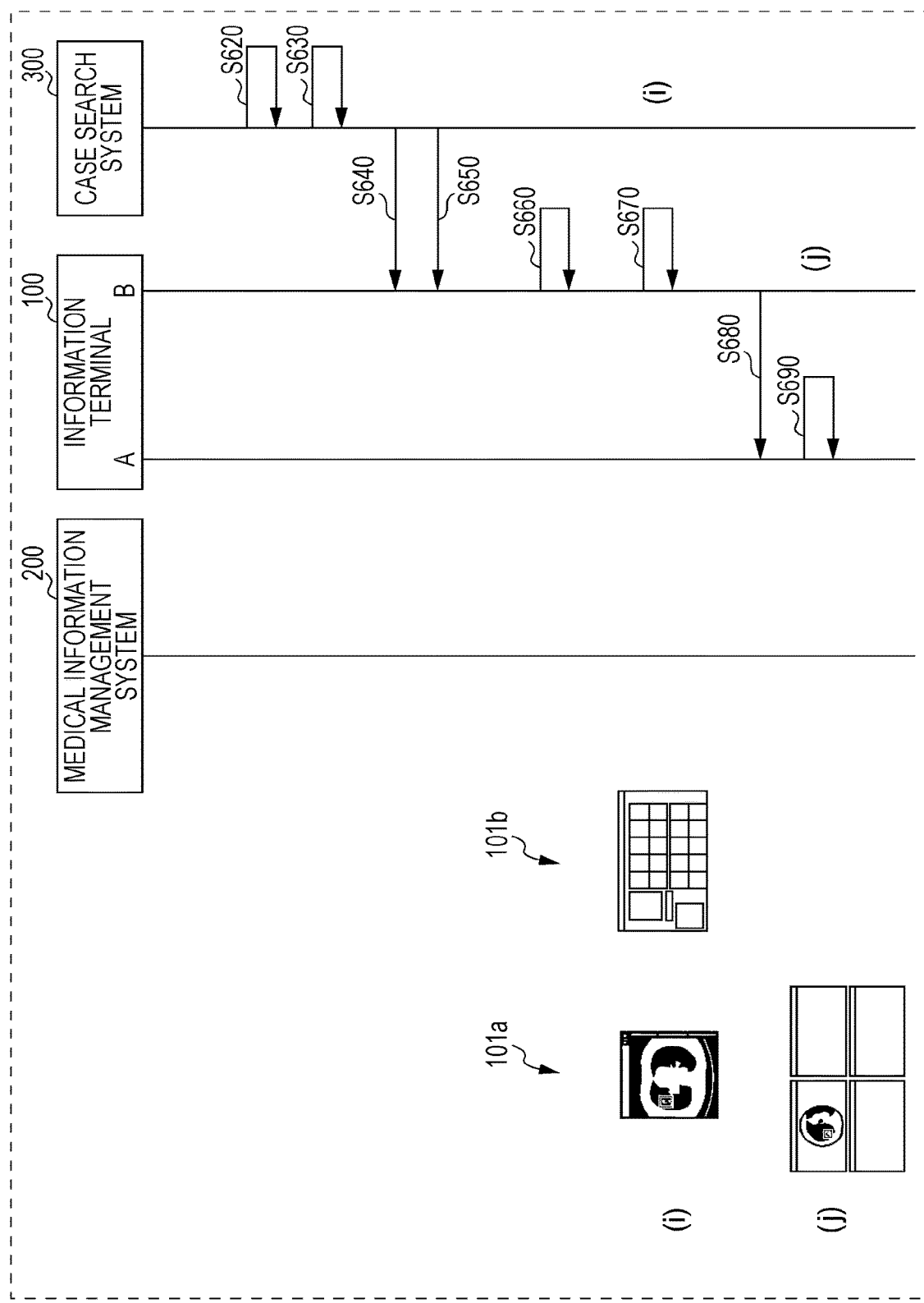
FIG. 52 is a sequence diagram illustrating a process performed until, after receiving a similar case search request, the case search system returns similar case search results to the information terminal.

FIG. 52 is a sequence diagram illustrating a process performed until, after receiving a similar case search request, the case search system 300 returns similar case search results to the information terminal 100. The difference from FIG. 39 is that, since the extraction of an image feature is performed on the information terminal 100 side, the extraction (S610) of an image feature in FIG. 39 is omitted in FIG. 52.

Figure 53:
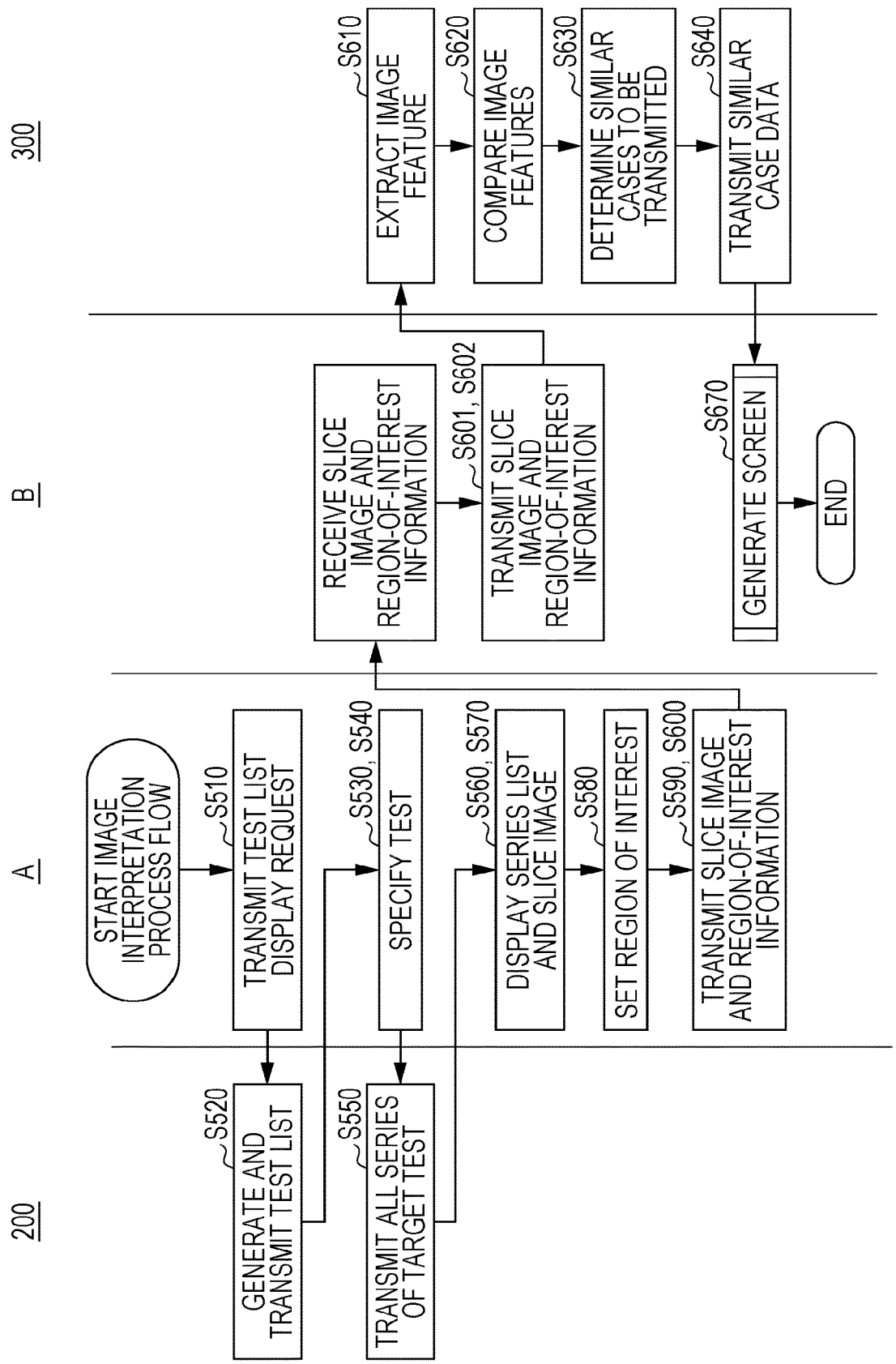
FIG. 53 is a sequence diagram focusing on the sequence diagrams illustrated in FIG. 34 and FIG. 39 at an application level.

Next, the process performed by the information terminal 100, the medical information management system 200, and the case search system 300 when the focus is on the sequence diagrams illustrated in FIG. 34 and FIG. 39 at an application level will be described. FIG. 53 is a sequence diagram focusing on the sequence diagrams illustrated in FIG. 34 and FIG. 39 at an application level. In FIG. 53, the same or substantially the same processing steps as those in FIG. 34 are assigned the same numerals.

In FIG. 53, part "A" depicts the process of the medical information management application executed by the information terminal 100, and part "B" depicts the process of the similar case search application executed by the information terminal 100. In the following, the medical information management application is represented by the "application A", and the similar case search application is represented by the "application B".

First, the application A accepts a request from a user for displaying a test list in which image interpretation is to be performed, and transmits the request to the medical information management system 200 (S510). Upon receipt of the request, the medical information management system 200 lists tests in which image interpretation has not been completed after the completion of an imaging test to generate a test list in which image interpretation is to be performed, and transmits the test list to the application A (S520).

Upon receipt of the test list, the application A displays the test list on the display 101 in the manner illustrated in FIG. 35. When the user selects one test from the test list (S530), the application A transmits a request for displaying the selected test to the medical information management system 200 (S540).

Upon receipt of the request for displaying the test, the medical information management system 200 transmits all the slice images in all the series included in the test ID specified in the request to the application A (S550).

Then, as illustrated in FIG. 36, the application A displays a series list in which pieces of information concerning all the series included in the specified test ID are displayed in list form (S560).

Then, when a series to be subjected to image interpretation is selected by the user from the series list, the application A displays the slice image corresponding to the initial slice position in the selected series in the medical image viewer 610 (S570). In this case, the user inputs a slice-to-slice switching operation to display the desired slice image in the medical image viewer 610.

Then, the application A accepts an operation of setting a region of interest on the slice image displayed in the medical image viewer 610 from the user (S580).

Then, the application A generates region-of-interest information indicating the region of interest set by the user, and transmits the region-of-interest information together with the slice image on which the region of interest has been set (i.e., the slice image of the case to be diagnosed) to the application B (S590, S600).

Upon receipt of the slice image of the case to be diagnosed and the region-of-interest information, the application B transmits the slice image and the region-of-interest information to the case search system 300 (S601, S602).

Upon receipt of the slice image and the region-of-interest information, as in FIG. 39, the case search system 300 executes the processes of S610 to S640.

Then, the application B generates an initial basic screen by using the similar case data transmitted in S640 and the display box management information 4410 (S670). Then, the application B executes the process of S670, the details of which are illustrated in FIG. 41.

Figure 54:
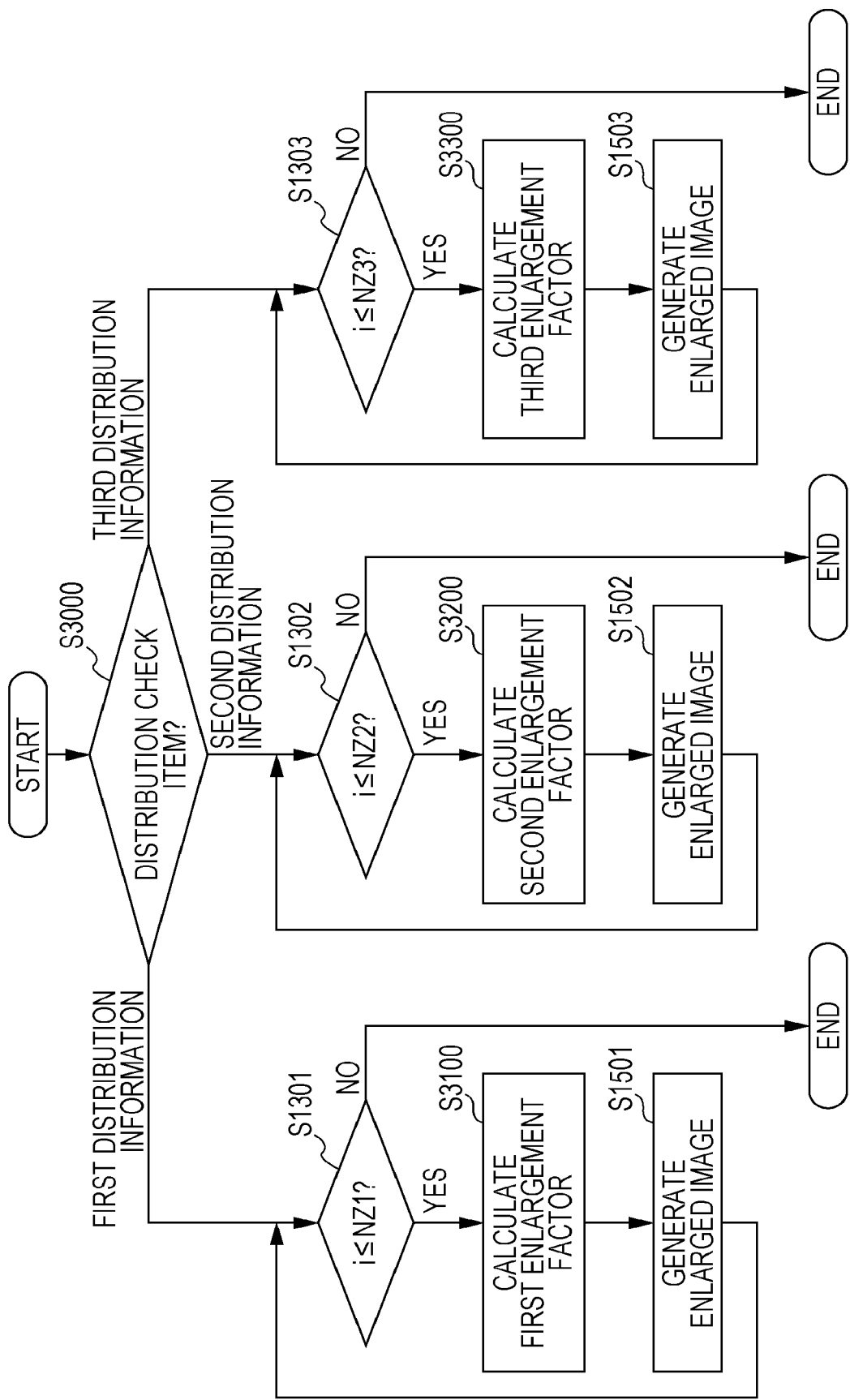
FIG. 54 is a flowchart illustrating a process performed when a lesion distribution displayed in the distribution list display area is selected.

Next, a process performed when a lesion distribution displayed in the distribution list display area 750 illustrated in FIG. 23 is selected will be described. FIG. 54 is a flowchart illustrating a process performed when a lesion distribution displayed in the distribution list display area 750 is selected.

In S3000, when the input control unit 103 detects the selection of anyone distribution check item among the lesion distributions (or distribution check items) displayed in the distribution list display area 750, the display control unit 104 determines which of the first distribution information, the second distribution information, and the third distribution information corresponds to the distribution check item for which the selection has been detected. If the first distribution information corresponds to the distribution check item for which the selection has been detected, the process proceeds to S1301. If the second distribution information corresponds to the distribution check item for which the selection has been detected, the process proceeds to S1302. If the third distribution information corresponds to the distribution check item for which the selection has been detected, the process proceeds to S1303.

The first distribution information is information for selecting a thumbnail image in which a region of interest belongs to a predetermined first range indicating that the size of the region of interest is wide relative to the lung area among the thumbnail images of the similar cases displayed in list form in the case display area 710. Here, the first distribution information corresponds to "bilateral", "multiple", "diffuse", and "hematogenous". Accordingly, the first range is a range of values to which the size of the region of interest set for the diagnosis of such lesion distributions belongs.

The second distribution information is information for selecting a thumbnail image in which a region of interest belongs to a predetermined second range (lower than the first range; the upper limit of the second range is less than or equal to the lower limit of the first range value) indicating that the size of the region corresponding to the region of interest is part of the lung area among the thumbnail images of the similar cases displayed in list form in the case display area 710. Here, the second distribution information corresponds to "bronchial" and "segmental". Accordingly, the second range is a range of values to which the size of the region of interest set for the diagnosis of such lesion distributions belongs.

The third distribution information is information for selecting a thumbnail image in which a region of interest includes a pleura among the thumbnail images of the similar cases displayed in list form in the case display area 710. Here, the third distribution information corresponds to "subpleural".

In S1301, the display control unit 104 extracts similar cases, which are obtained as a result of the similar case search and the number of which is less than or equal to the maximum number of (in this embodiment, 20) thumbnail images that can be displayed in the case display area 710, among the similar cases corresponding to a lesion distribution selected as first distribution information by the user, in order of decreasing similarity, and determines the number of extracted similar cases as the number of similar cases NZ1 to be subjected to enlargement. Further, the display control unit 104 determines a thumbnail image of an extracted similar case i (where i is an index identifying an extracted similar case and is an integer greater than or equal to 1) as a processing target thumbnail image. The display control unit 104 repeatedly performs the processes of S3100 and S1501 until the value of the index i has reached NZ1. The display control unit 104 increments the value of the index i by 1 each time the processes of S3100 and S1501 are executed. If the value of the index i exceeds NZ1 (NO in S1301), the process ends.

In S3100, the display control unit 104 calculates a first enlargement factor for the first distribution information on the similar case i. Here, the first enlargement factor is, for example, 1.0. However, this is an example, and any value other than 1.0 may be used as the first enlargement factor as long as the entire region of interest set for the diagnosis of a lesion distribution indicated by the first distribution information falls within the display area.

In S1501, the display control unit 104 enlarges the thumbnail image of the similar case i with the first enlargement factor for the similar case i.

Figure 55:
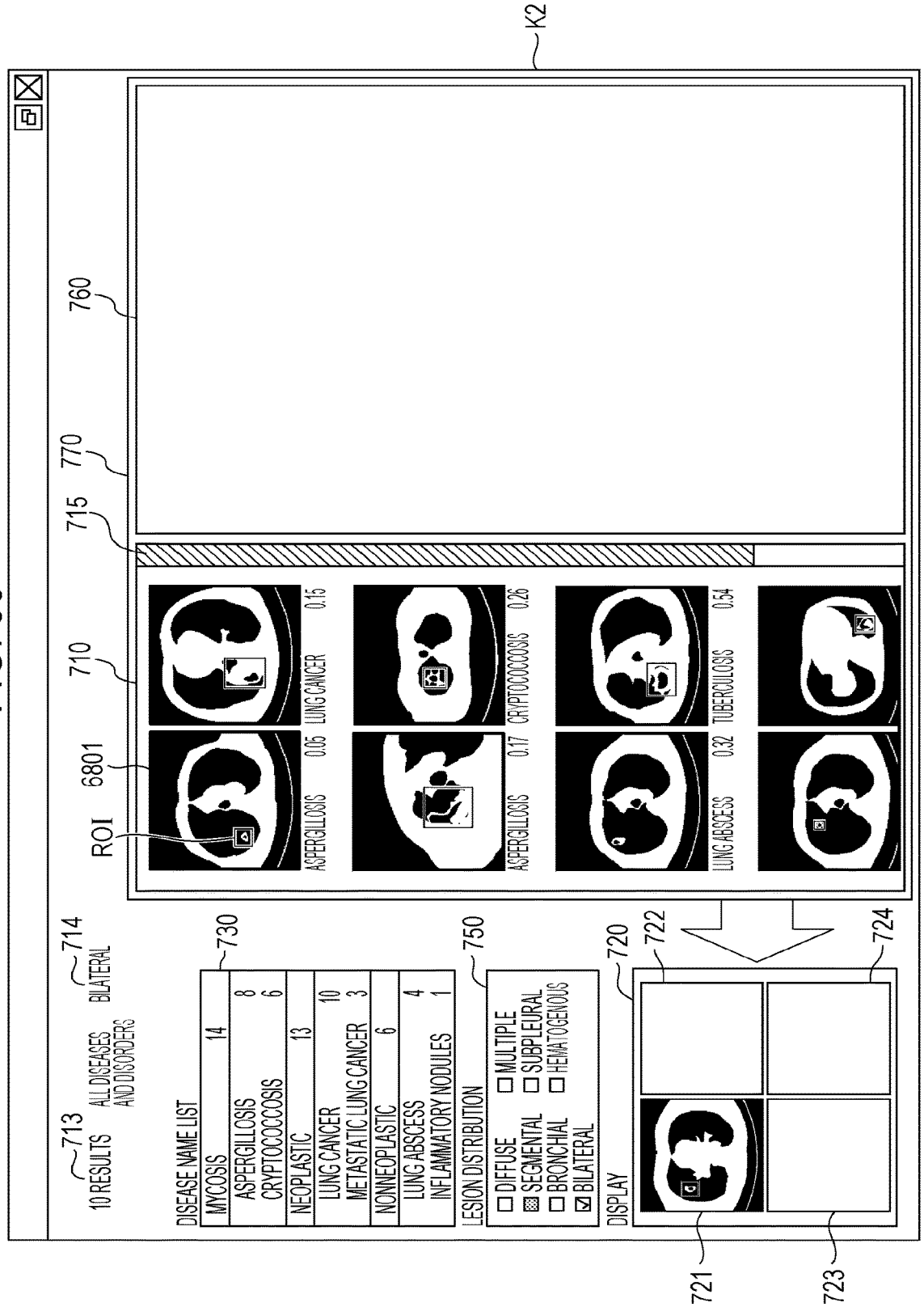
FIG. 55 is a diagram illustrating a basic screen obtained when first distribution information is selected.

FIG. 55 is a diagram illustrating the basic screen K2 obtained when the first distribution information is selected. In FIG. 55, "bilateral" is selected. In this case, thumbnail images of similar cases for which the lesion distribution is bilateral among the similar cases are displayed in the case display area 710. In addition, since the enlargement factor is 1.0, the thumbnail images are displayed in the same display style as the thumbnail images displayed in the case display area 710 immediately after similar case search results have been obtained. That is, the thumbnail images are displayed without adjusting the display positions of the thumbnail images so that the center of the region of interest ROI in each thumbnail image matches the center of a display area 6801 or without enlarging the thumbnail images.

In S1302, the display control unit 104 extracts similar cases, which are obtained as a result of the similar case search and the number of which is less than or equal to the maximum number of thumbnail images that can be displayed in the case display area 710, among the similar cases corresponding to a lesion distribution selected as second distribution information by the user, in order of decreasing similarity, and determines the number of extracted similar cases as the number of similar cases NZ2 to be subjected to enlargement. Further, the display control unit 104 determines a thumbnail image of an extracted similar case i as a processing target thumbnail image. The display control unit 104 repeatedly performs the processes of S3200 and S1502 until the value of the index i has reached NZ2. The display control unit 104 increments the value of the index i by 1 each time the processes of S3200 and S1502 are executed. If the value of the index i exceeds NZ2 (NO in S1302), the process ends.

In S3200, the display control unit 104 calculates a second enlargement factor for the second distribution information on the similar case i by using a display area size determined in advance for each thumbnail image in the case display area 710 and by using the region-of-interest information on the similar case i.

If the second distribution information is selected, the thumbnail image of the similar case i is enlarged so that the size of the region of interest is equal to approximately one half of the size of the display area. Accordingly, for example, the display control unit 104 computes a second enlargement factor ki for the similar case i in accordance with the following equation:

$$ki = \frac{1}{2}(Sd/Si),$$

where Sd denotes the area of the display area and Si denotes the area of the region of interest in the thumbnail image of the similar case i to be enlarged.

In S1502, the display control unit 104 enlarges the thumbnail image of the similar case i with the second enlargement factor ki, and displays the thumbnail image in the case display area 710 so that the center of the region of interest in the thumbnail image is located at the center of the display area.

Figure 56:
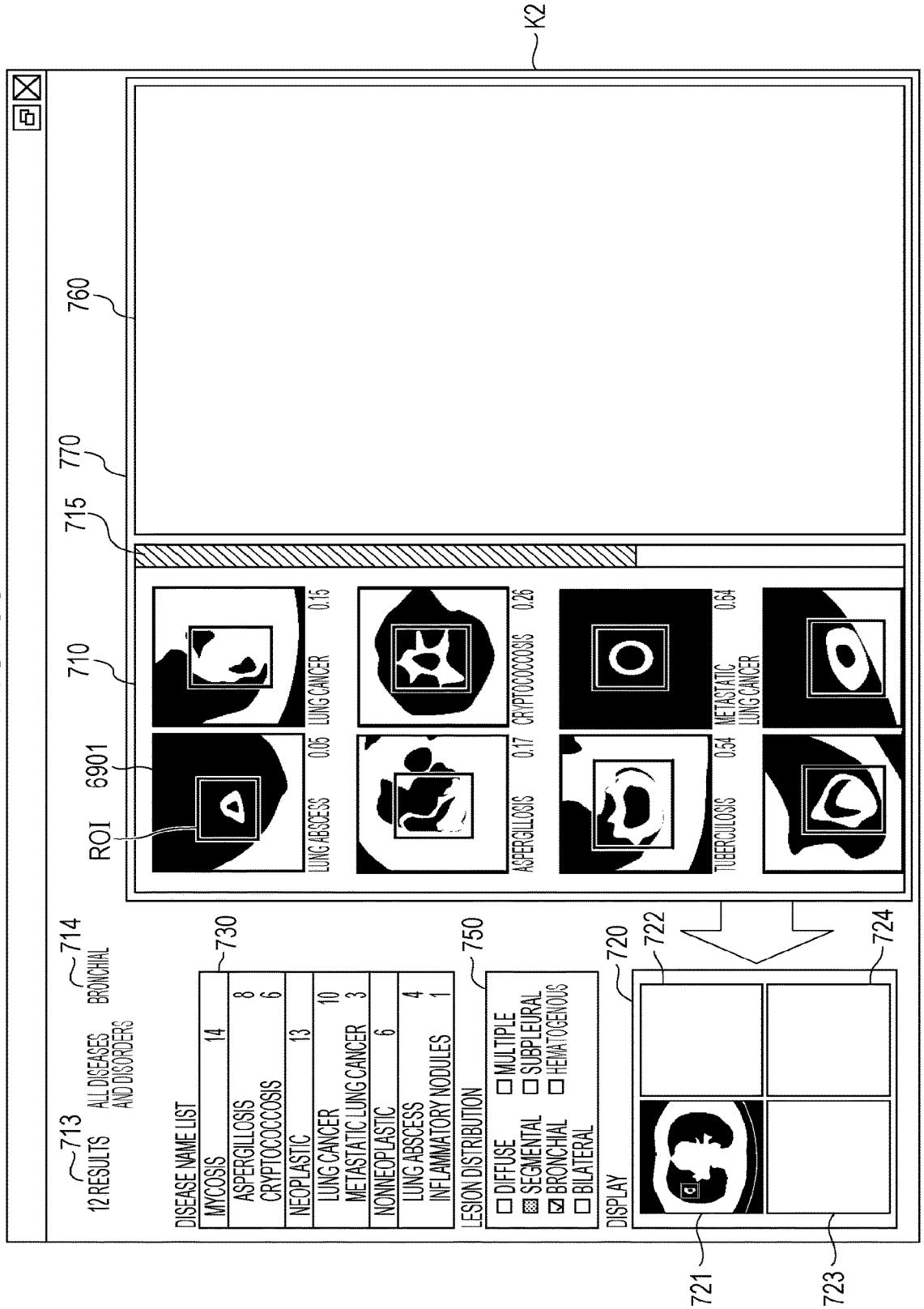
FIG. 56 is a diagram illustrating a basic screen obtained when second distribution information is selected.

FIG. 56 is a diagram illustrating the basic screen K2 obtained when the second distribution information is selected. In FIG. 56, "bronchial" is selected. In this case, thumbnail images of similar cases for which the lesion distribution is bronchial among the similar cases are displayed in the case display area 710. In the case display area 710, all the thumbnail images have been enlarged with the second enlargement factor so that the center of the region of interest ROI in each thumbnail image matches the center of a display area 6901.

In S1303, the display control unit 104 extracts similar cases, which are obtained as a result of the similar case search and the number of which is less than or equal to the maximum number of thumbnail images that can be displayed in the case display area 710, among the similar cases corresponding to a lesion distribution selected as third distribution information by the user, in order of decreasing similarity, and determines the number of extracted similar cases as the number of similar cases NZ3 to be subjected to enlargement. Further, the display control unit 104 determines a thumbnail image of an extracted similar case i as a processing target thumbnail image. The display control unit 104 repeatedly performs the processes of S3300 and S1503 until the value of the index i has reached NZ3. The display control unit 104 increments the value of the index i by 1 each time the processes of S3300 and S1503 are executed. If the value of the index i exceeds NZ3 (NO in S1303), the process ends.

In S3300, the display control unit 104 calculates a third enlargement factor for the third distribution information on the similar case i by using a display area size determined in advance for each thumbnail image in the case display area 710 and by using the region-of-interest information on the similar case i and pleural area information 4900.

Figure 57:
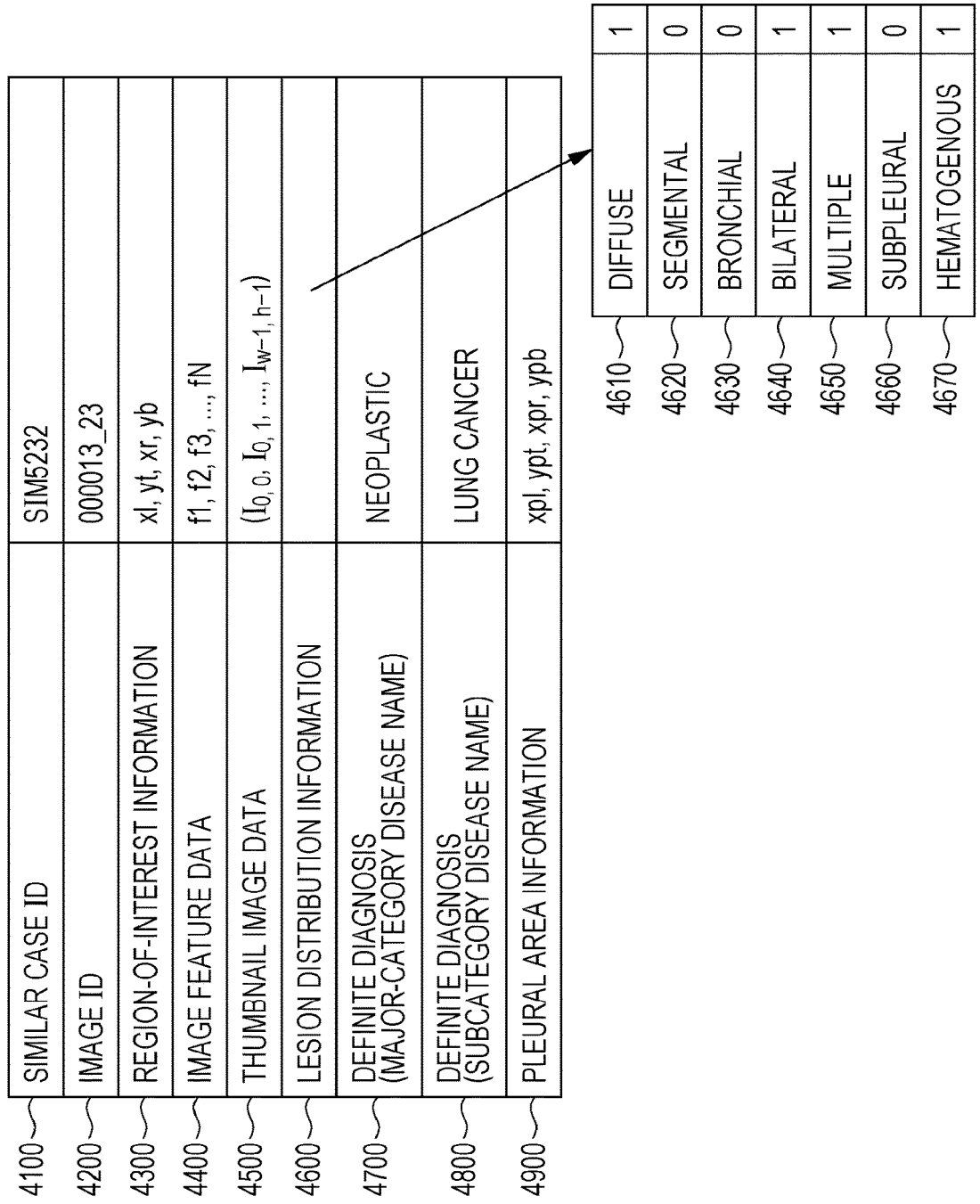
FIG. 57 is a diagram illustrating the data configuration of similar case data that further includes a pleural area information.

FIG. 57 is a diagram illustrating the data configuration of similar case data 4000 that additionally includes the pleural area information 4900. If the similar case data 4000 does not have registered therein the pleural area information 4900, the pleural area information 4900 is not obtained. In this case, it may be sufficient that the display control unit 104 sets the third enlargement factor to 1.0, which is equal to the first enlargement factor. The pleural area information 4900 is information indicating the pleural area in a similar case.

In S1503, the display control unit 104 enlarges the thumbnail image of the similar case i with a third enlargement factor ki, and displays the thumbnail image in the case display area 710 so that the center of the region of interest in the thumbnail image is located at the center of the display area.

Figure 58:
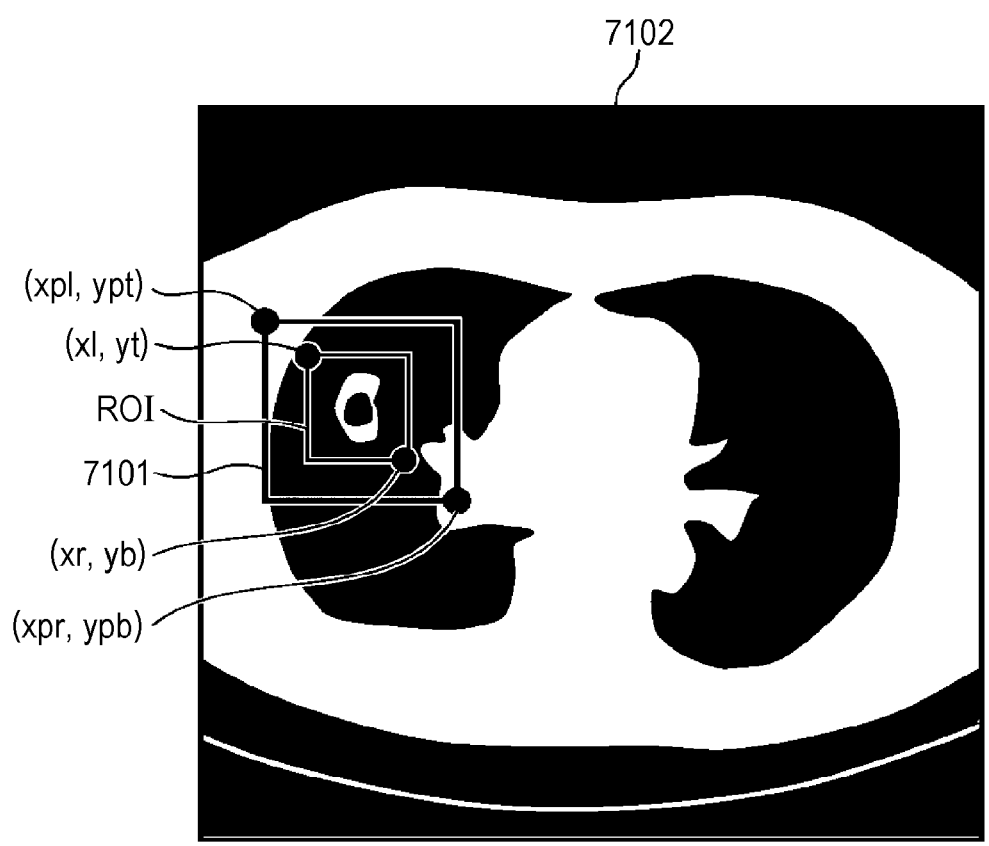
FIG. 58 is a diagram depicting a pleural area.

FIG. 58 is a diagram depicting a pleural area 7101. As illustrated in FIG. 58, the pleural area 7101 includes a pleura and is a rectangular area that is centered on the center of the region of interest ROI and that has a slightly larger size than the region of interest ROI. The pleural area information 4900 includes four values, namely, the coordinates (xpl, ypt) of the upper left corner of the pleural area 7101 and the coordinates (xpr, ypb) of the lower right corner of the pleural area 7101. If the third distribution information is selected, the pleural area is enlarged and displayed. Thus, the display control unit 104 computes the third enlargement factor ki in accordance with the following equation:

$$ki = Sd/Sp,$$

where Sd denotes the area of a display area 7102 and Sp denotes the area of the pleural area 7101.

The user may input the pleural area information 4900 together with region-of-interest information when creating the similar case data 4000.

Alternatively, the pleural area information 4900 may be automatically created by an image processing device by automatically extracting the lung area from a slice image and determining the pleural position.

Figure 59:
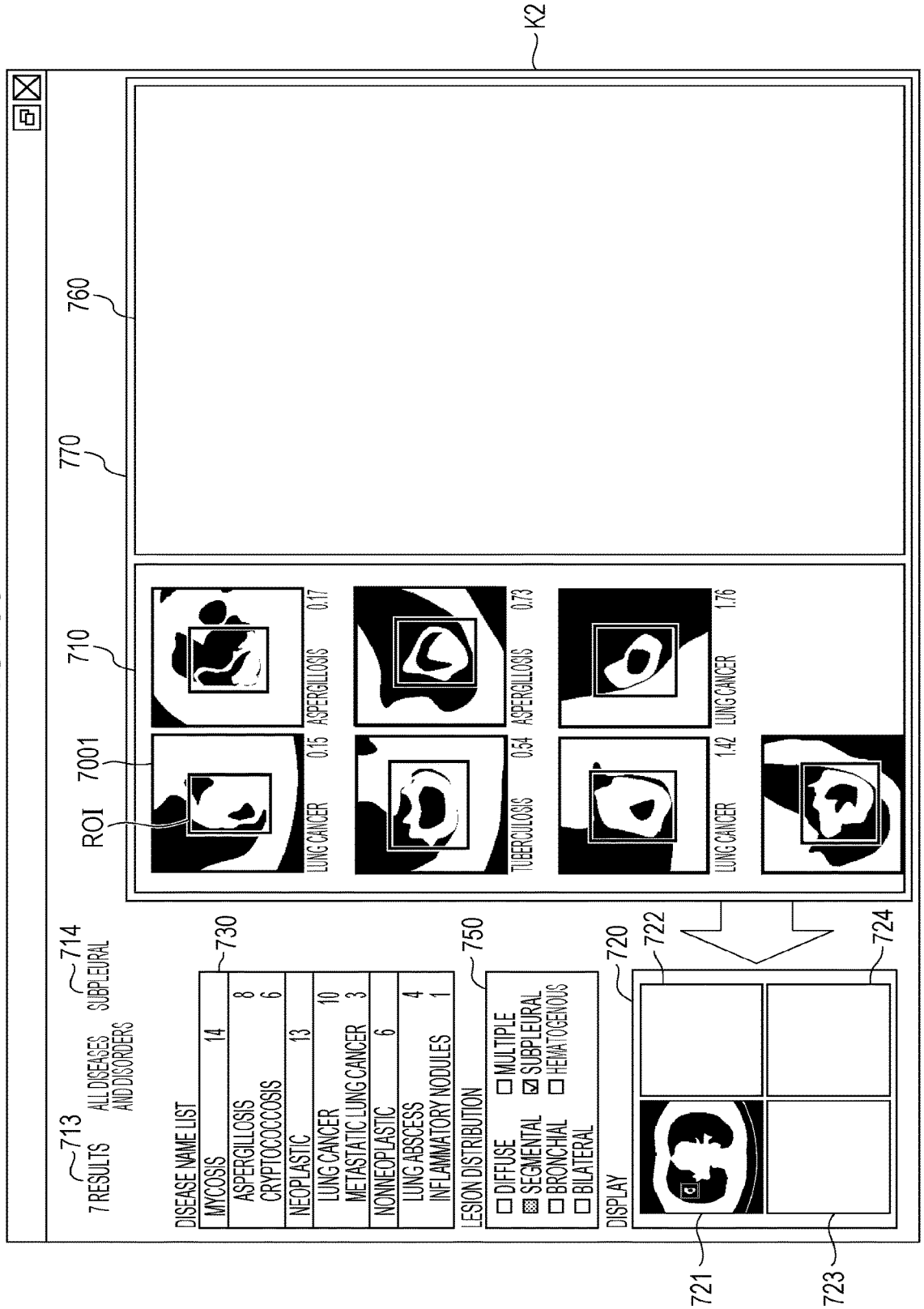
FIG. 59 is a diagram illustrating a basic screen obtained when third distribution information is selected.

FIG. 59 is a diagram illustrating the basic screen K2 obtained when the third distribution information is selected. In FIG. 59, "subpleural" is selected. In this case, thumbnail images of similar cases for which the lesion distribution is subpleural among the similar cases are displayed in the case display area 710. In the case display area 710, all the thumbnail images have been enlarged with the third enlargement factor so that the center of the region of interest ROI in each thumbnail image matches the center of a display area 7001.

The process described above allows thumbnail images to be displayed in the case display area 710 with an enlargement factor that reflects the content of the diagnosis regarding a lesion distribution. In addition, the thumbnail images are displayed with the sizes of the regions of interest being uniform in the case display area 710. This can prevent the regions of interest in some similar medical images from being overlooked because such similar medical images have been enlarged in such a manner that the regions of interest are small, and can improve diagnostic accuracy. In addition, not all the similar cases obtained as a result of the similar case search but similar cases displayed in the case display area 710 are subjected to an enlargement process, resulting in a significantly reduced load on a system.

In this embodiment, a plurality of electronic medical books are accumulated in the medical book data accumulation unit 221 of the medical book data section 220 (FIG. 2). An electronic medical book containing a similar case (thumbnail image) displayed in the case display area 710 of the similar case data display area 770 is identified by the medical book ID 421 in the medical book image data 420 (FIG. 5).

In general, there are a variety of kinds of electronic medical books, and electronic medical books to which radiologists wish to refer differ. For example, electronic medical books mainly include electronic medical books used for educational purposes and electronic medical books used for diagnostic purposes. The electronic medical books used for educational purposes describe in detail differential items that are information necessary for determining a disease name. In contrast, the electronic medical books used for diagnostic purposes contain a large number of diverse medical images corresponding to specific disease names. Thus, there is a need for a radiologist to select either electronic medical book to efficiently obtain information necessary for diagnosis. To this end, the medical books accumulated in the medical book data accumulation unit 221 may be displayed on the display 101 so as to be distinguishable from one another.

Figure 60:
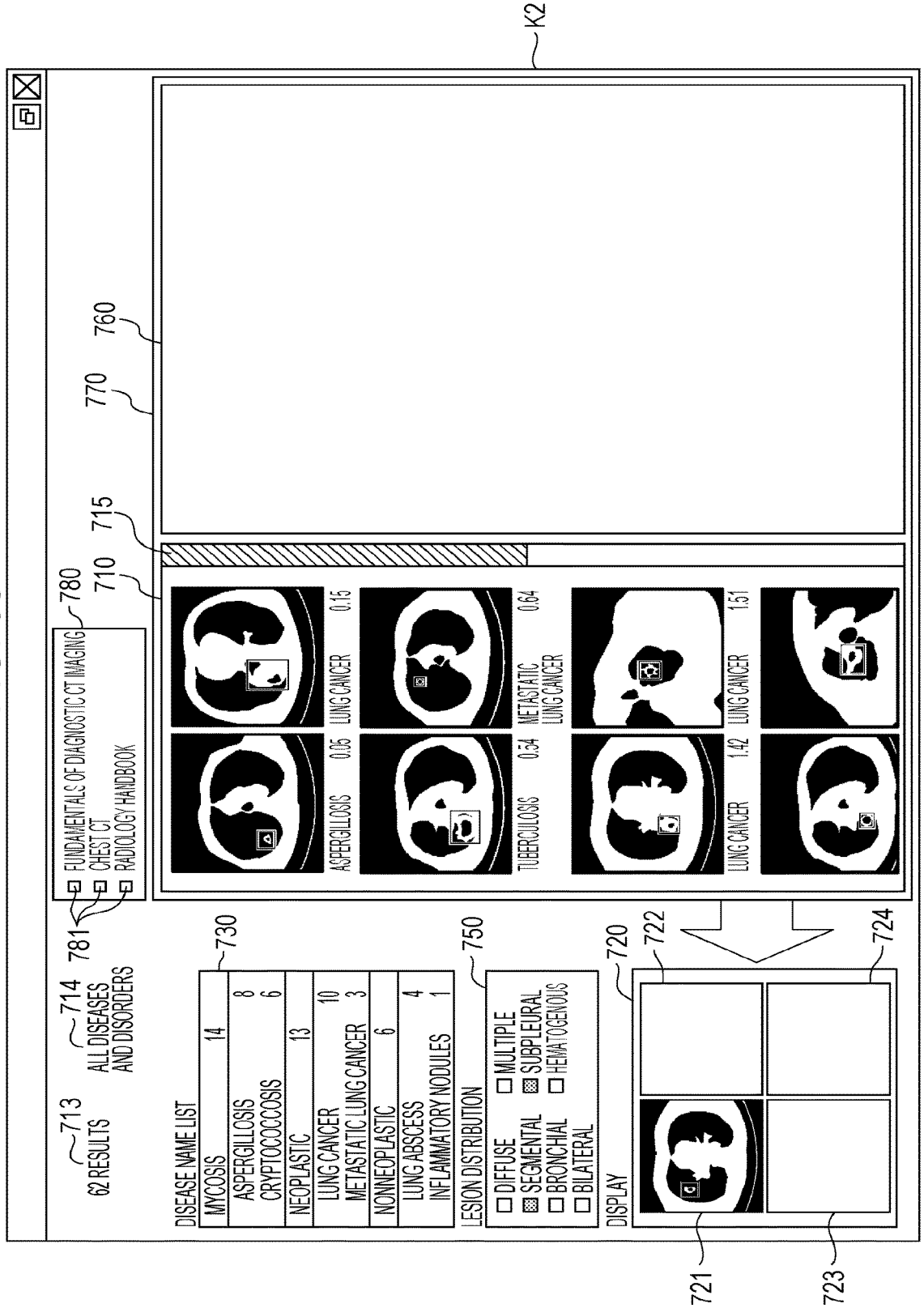
FIG. 60 is a diagram illustrating an example of a basic screen including a book title display area.
Figure 61:
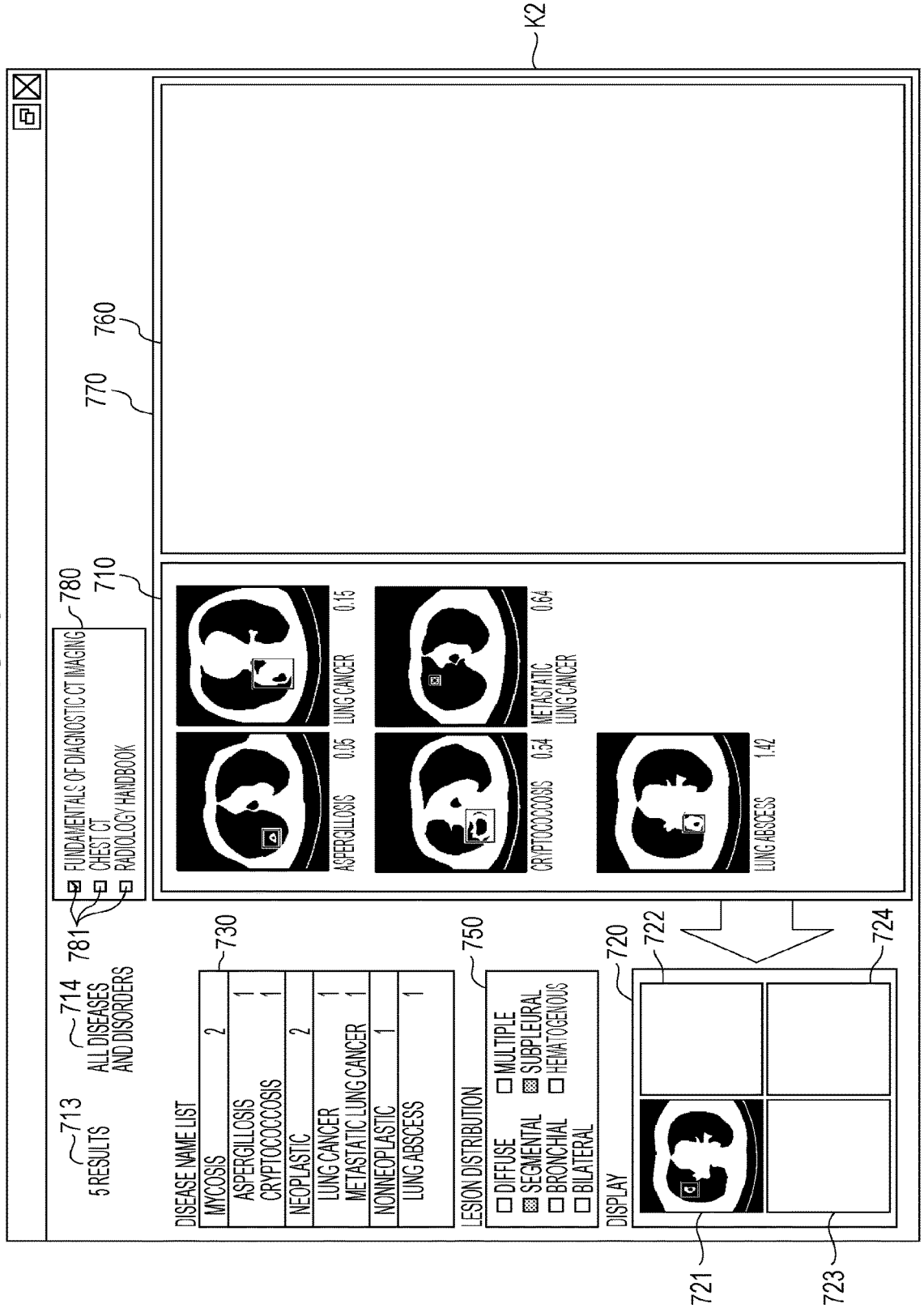
FIG. 61 is a diagram illustrating an example of a basic screen obtained when a book title is selected.

FIG. 60 is a diagram illustrating an example of a basic screen K2 including a book title display area 780. FIG. 61 is a diagram illustrating an example of the basic screen K2 obtained when a book title displayed in the book title display area 780 is selected.

The display control unit 104 displays, in the book title display area 780, the titles of the medical books accumulated in the medical book data accumulation unit 221 of the medical book data section 220. The display control unit 104 displays, in the book title display area 780, the title written in the book title 413 in the medical book data 410 (FIG. 4). The display control unit 104 holds the medical book ID 411 in association with the display position of the book title 413 to be displayed. In FIG. 60, the display control unit 104 further displays checkboxes 781 in the book title display area 780 so that each of the checkboxes 781 corresponds to one of the displayed book titles.

When a radiologist selects a checkbox 781 for the medical book to which they wish to refer from among the checkboxes 781 displayed in the book title display area 780, the input control unit 103 detects the position of the selected checkbox 781. The display control unit 104 obtains the detected position of the checkbox 781 from the input control unit 103. The display control unit 104 determines the medical book ID 411 corresponding to the obtained position of the checkbox 781. The display control unit 104 searches for the image ID 423 in the medical book image data 420 (FIG. 5) on the basis of the image ID 4200 (FIG. 32) of a similar case (thumbnail image) displayed in the case display area 710.

The display control unit 104 extracts the image ID 423 so that the medical book ID 421 associated with the image ID 423 found as a result of the search matches the medical book ID 411 corresponding to the position of the selected checkbox 781. As illustrated in FIG. 61, the display control unit 104 displays, in the case display area 710, similar cases (thumbnail images) found from the medical book selected by the user (radiologist) by using the extracted image ID 423.

In the embodiment illustrated in FIG. 60 and FIG. 61, accordingly, when the input control unit 103 detects the selection of one of a plurality of electronic medical books, similar cases (thumbnail images) contained in the selected electronic medical book are displayed in the case display area 710 by the display control unit 104. This enables efficient presentation of information required by the radiologist.

The radiologist does not necessarily remember the title of the medical book to which they wish to refer, but may remember the cover of the medical book. Thus, thumbnail images of covers of electronic medical books may be displayed instead of book titles.

Figure 62:
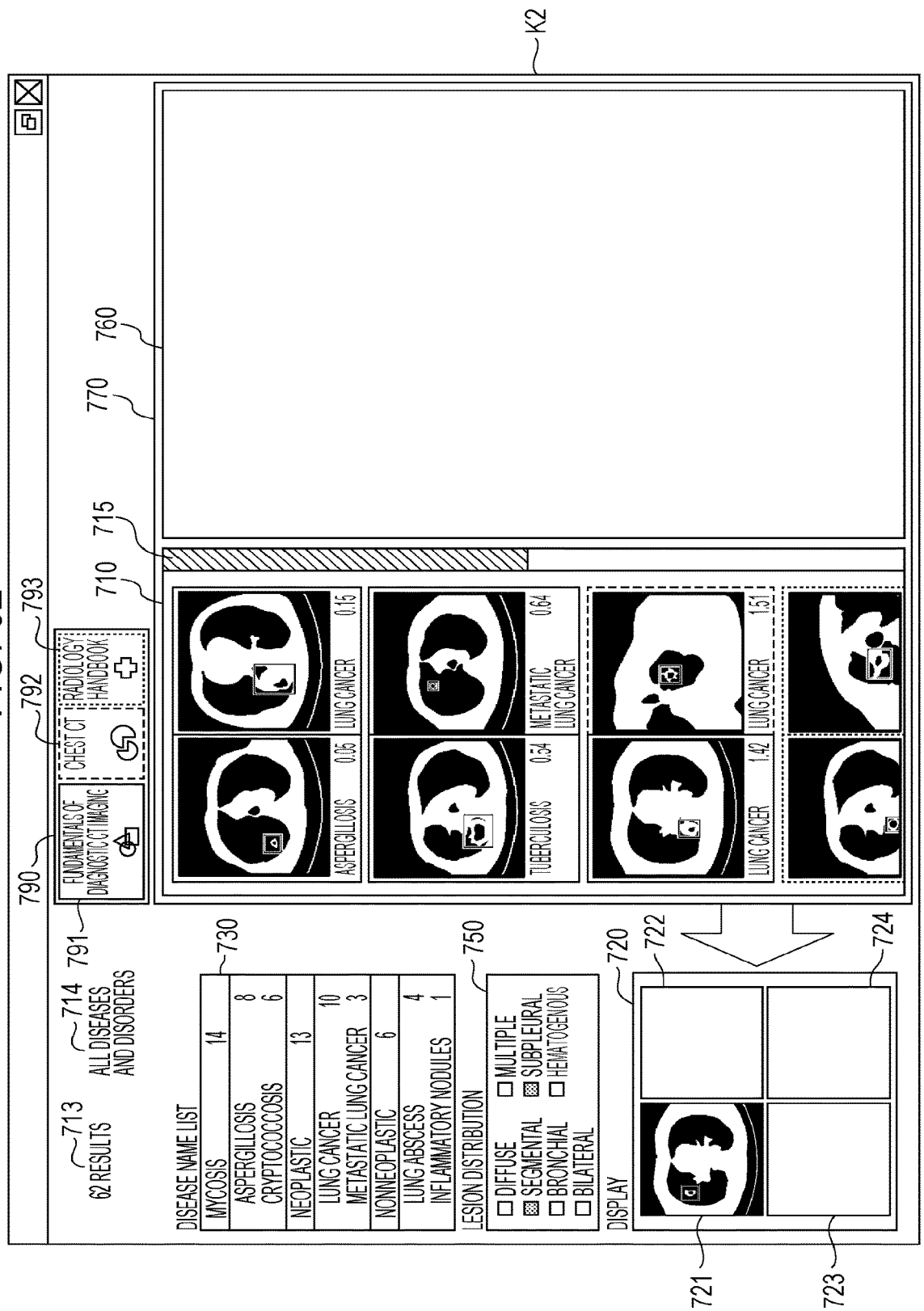
FIG. 62 is a diagram illustrating an example of a basic screen including a book image display area.
Figure 63:
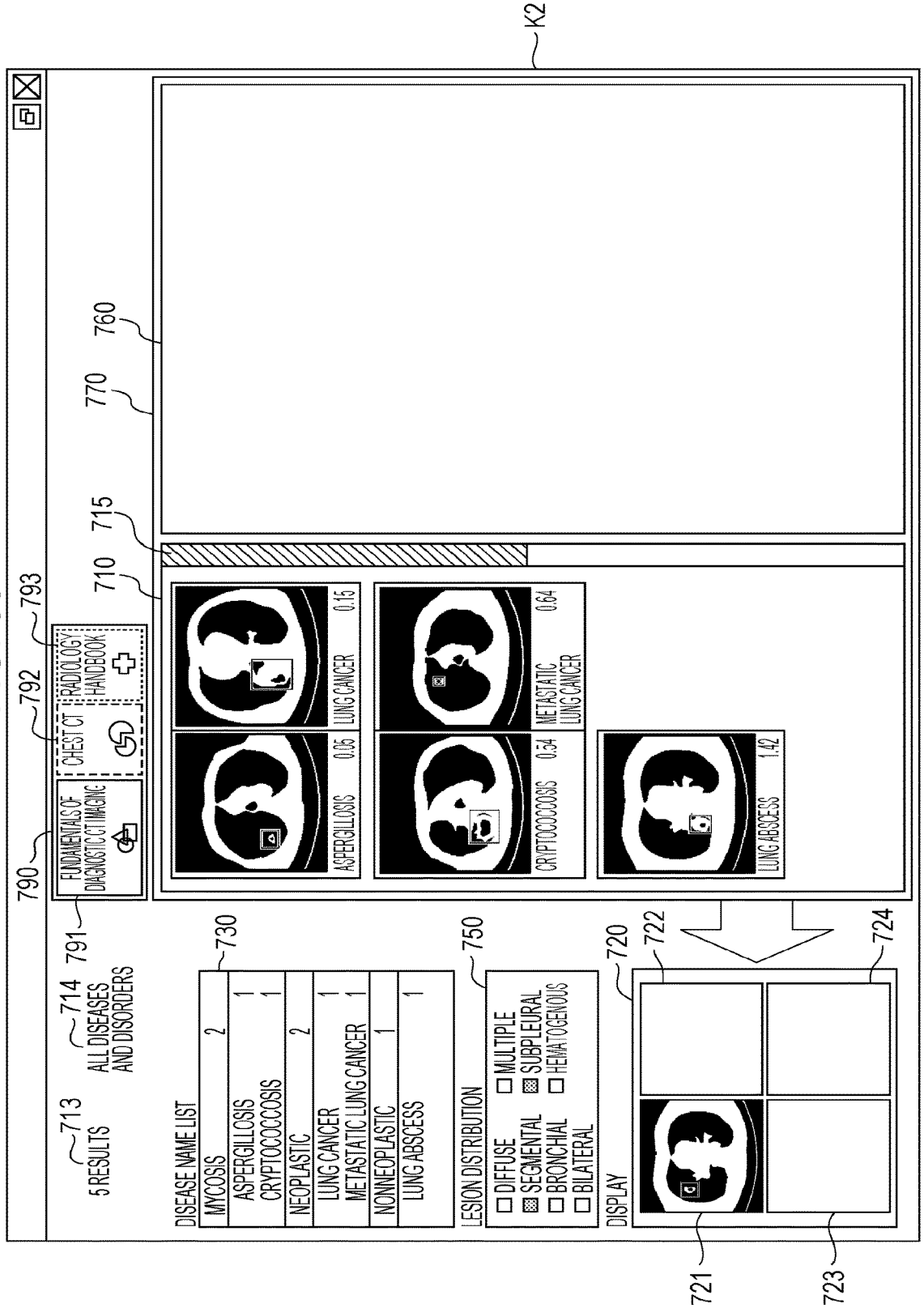
FIG. 63 is a diagram illustrating an example of a basic screen obtained when a cover image is selected.

FIG. 62 is a diagram illustrating an example of a basic screen K2 including a book image display area 790. FIG. 63 is a diagram illustrating an example of the basic screen K2 obtained when a cover image 791 displayed in the book image display area 790 is selected.

The display control unit 104 displays, in the book image display area 790, the cover images of the medical books accumulated in the medical book data accumulation unit 221 of the medical book data section 220. The display control unit 104 displays, in the book image display area 790, a cover image stored with the path to the cover image 414 in the medical book data 410 (FIG. 4). The display control unit 104 holds the medical book ID 411 in association with the display position of the cover image to be displayed. In FIG. 62, the display control unit 104 displays cover images 791, 792, and 793 of three medical books in the book image display area 790.

In FIG. 62, furthermore, the display control unit 104 distinguishably displays medical books containing the similar cases displayed in the case display area 710. That is, the cover image 791 is surrounded by a solid-line frame, and similar cases (five similar cases at the first row and the first column to the third row and the first column) in the case display area 710 which are contained in the medical book having the cover image 791 are also surrounded by solid-line frames. The cover image 792 is surrounded by a broken-line frame, and a similar case (a similar case at the third row and the second column) in the case display area 710 which is contained in the medical book having the cover image 792 is also surrounded by a broken-line frame. The cover image 793 is surrounded by a dotted-line frame, and similar cases (two similar cases at the fourth row and the first column and at the fourth row and the second column) in the case display area 710 which are contained in the medical book having the cover image 793 are also surrounded by dotted-line frames.

In FIG. 62, the display control unit 104 distinguishably displays the medical books containing the similar cases displayed in the case display area 710, using frames of different types of lines. However, the present disclosure is not limited thereto. For example, the display control unit 104 may distinguishably display the medical books containing the similar cases displayed in the case display area 710, using frames in different colors.

When a radiologist selects a cover image of the medical book to which they wish to refer from among the cover images 791 to 793 displayed in the book image display area 790, the input control unit 103 detects the selected position. The display control unit 104 obtains the detected selected position from the input control unit 103. The display control unit 104 determines the medical book ID 411 of the medical book having the cover image corresponding to the obtained selected position. The display control unit 104 searches for the image ID 423 in the medical book image data 420 (FIG. 5) on the basis of the image ID 4200 (FIG. 32) of a similar case (thumbnail image) displayed in the case display area 710.

The display control unit 104 extracts the image ID 423 so that the medical book ID 421 associated with the image ID 423 found as a result of the search matches the medical book ID 411 of the cover image corresponding to the selected position. As illustrated in FIG. 63, the display control unit 104 displays, in the case display area 710, similar cases (thumbnail images) found from the medical book selected by the user (radiologist) by using the extracted image ID 423.

As illustrated in FIG. 62, the display control unit 104 distinguishably displays medical books containing the similar cases displayed in the case display area 710. This enables a radiologist to more easily select the medical book to which they wish to refer, and enables efficient presentation of the information required by the radiologist.

In this embodiment, the display control unit 104 displays the basic screen K2 illustrated in FIG. 9 in the display 101*b* immediately after the similar case search application has been started on the information terminal 100. However, this embodiment is not limited thereto.

Figure 64:
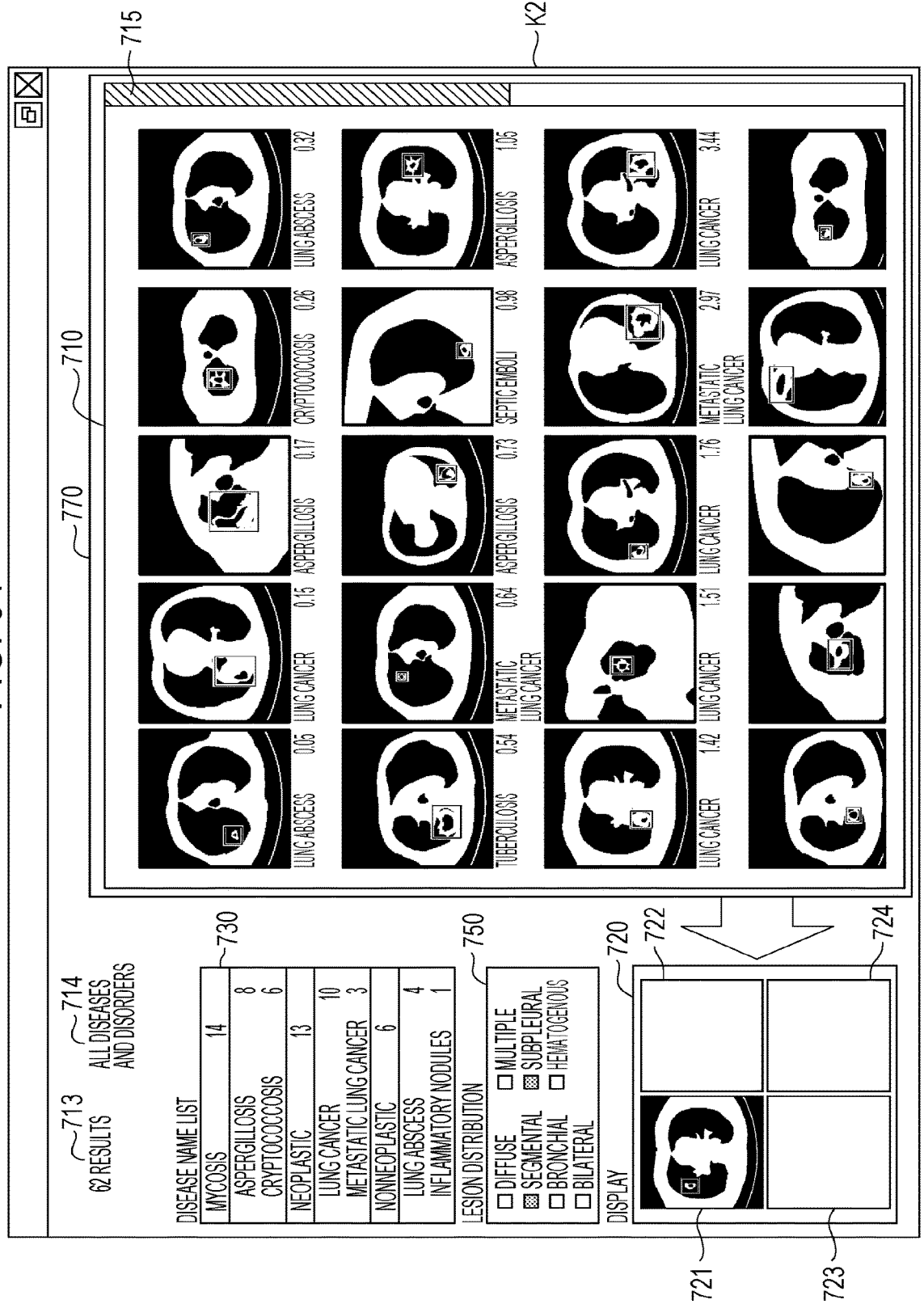
FIG. 64 is a diagram illustrating another example of a basic screen displayed on a display immediately after the similar case search application has been started on the information terminal.

FIG. 64 is a diagram illustrating another example of the basic screen K2 displayed on the display 101*b* immediately after the similar case search application has been started on the information terminal 100. As illustrated in FIG. 64, the display control unit 104 may display the similar case data display area 770 including the case display area 710 immediately after the similar case search application has been started.

In FIG. 64, when the input control unit 103 detects a selection made by a user within the case display area 710, the display control unit 104 may switch the display of the similar case data display area 770 including the case display area 710 to, as illustrated in FIG. 15, the similar case data display area 770 including the case display area 710 and the medical book display area 760. In addition, in FIG. 64, when the input control unit 103 detects a selection made by a user within the disease name list display area 730, the display control unit 104 may switch the display of the similar case data display area 770 including the case display area 710 to, as illustrated in FIG. 16, the similar case data display area 770 including the case display area 710 and the medical book display area 760.

A control method may have the following configuration.

The basic screen K2 illustrated in FIG. 9 is displayed on the display 101*b* immediately after the similar case search application has been started on the information terminal 100.

The input control unit 103 obtains position information indicating a position selected on the display 101*b* by a user for the first time after an image which includes the disease name list display area 730 (FIG. 9) including a plurality of disease names (in the example illustrated in FIG. 9, aspergillosis, cryptococcosis, lung cancer, metastatic lung cancer, lung abscess, and inflammatory nodules) including a first disease name (in the example illustrated in FIG. 9, aspergillosis) and a plurality of thumbnails (in FIG. 9, the plurality of similar cases (thumbnail images) shown in the case display area 710) including a first thumbnail (in the example illustrated in FIG. 9, the similar case (thumbnail image) shown in the upper left portion of the case display area 710) has been displayed on the display 101*b*. The display control unit 104 obtains, from the input control unit 103, the position information obtained by the input control unit 103.

The plurality of thumbnails correspond to a plurality of disease names. That is, in the example illustrated in FIG. 9, the similar case (thumbnail image) shown in the upper left portion of the case display area 710 corresponds to "aspergillosis" in the disease name list display area 730. Further, the similar case (thumbnail image) shown in the upper right portion of the case display area 710, the third similar case (thumbnail image) from the similar case (thumbnail image) shown in the upper left portion of the case display area 710, and the third similar case (thumbnail image) from the similar case (thumbnail image) shown in the upper right portion of the case display area 710 correspond to "lung cancer" in the disease name list display area 730.

The plurality of thumbnails correspond to a plurality of similar medical images related to the target medical image to be interpreted. That is, each thumbnail is created in the following way. First, an image having a predetermined similarity to the target medical image to be interpreted is extracted from a medical book (electronic content). The extracted image is a similar medical image. Then, the similar medical image (original image) is subjected to a resolution reduction process and a grayscale conversion process to obtain a thumbnail image.

The plurality of similar medical images include a first similar medical image corresponding to a first thumbnail. That is, in the example illustrated in FIG. 9, the original image of the similar case (thumbnail image) shown in the upper left portion of the case display area 710 is included in electronic content, and the original image has a predetermined similarity to the target medical image to be interpreted.

If the obtained position information indicates the position at which the first disease name (in the example illustrated in FIG. 9, aspergillosis in the disease name list display area 730) is displayed in the disease name list display area 730, the display control unit 104 instructs a display to display part or all of a first page including differential items for a disease identified by the first disease name (e.g., if YES is obtained in S103 in FIG. 14, the process of S104 is executed: As a result of the display control unit 104 providing a display instruction to the display 101*b*, the content displayed on the display 101*b* (page 206 of an electronic medical book that is electronic content) is shown in the medical book display area 760 illustrated in FIG. 16).

If the obtained selected position is a position at which the first thumbnail is displayed, the display control unit 104 instructs the display to display part or all of a second page including the first similar medical image (e.g., if YES is obtained in S101 in FIG. 14, the process of S102 is executed: As a result of the display control unit 104 providing a display instruction to the display 101b, the content displayed on the display 101b (page 210 of an electronic medical book that is electronic content) is shown in the medical book display area 760 illustrated in FIG. 15).

If the first thumbnail corresponds to the first disease name, the same electronic content includes the first page and the second page. For example, in the example illustrated in FIG. 9, the similar case (thumbnail image) shown in the upper left portion of the case display area 710 corresponds to "aspergillosis" in the disease name list display area 730, and the page shown in the medical book display area 760 illustrated in FIG. 15 (i.e., page 210) and the page shown in the medical book display area 760 illustrated in FIG. 16 (i.e., page 206) are included in the same electronic content, or an electronic medical book (having the same medical book ID: see FIG. 5 and FIG. 6).

Embodiments of the present disclosure are applicable to a similar case search device configured to present similar cases to be used as references for diagnosis using a medical image to be interpreted, an image interpretation training device for trainee radiologists, and the like.

What is claimed is:

1. A method comprising:
    causing a display to display thumbnail images of a plurality of similar medical images each having a predetermined similarity to a target medical image to be interpreted in a first display area included in the display and disease names in a second display area included in the display, the thumbnail images including an ith thumbnail image, the disease names including an ith disease name, the ith thumbnail image corresponding to the ith disease name, wherein each of the thumbnail images in the first display area and each of the disease names in the second display area is selectable; and
    causing the display, immediately after a computer detects a first selection of the ith thumbnail image included in the first display area, to display a content on a page of an electronic medical book in a third area included in the display with the thumbnail images remaining displayed in the first display area and the disease names remaining displayed in the second display area,
    wherein the content on the page includes an ith similar medical image and the ith thumbnail image is generated on the basis of the ith similar medical image,
    wherein the first display area is an area where the thumbnail images are displayed before and after detection of a first selection of the ith disease name,
    wherein the second display area is an area where the disease names are displayed before and after the detection of the first selection of the ith thumbnail image, and
    wherein information displayed in the third area differs depending on whether the computer detects the first selection of the ith thumbnail image or a first selection of the ith disease name included in the second display area.

2. The method of claim 1, wherein the third area is an area dedicated to displaying the content after the detection of the first selection of the ith thumbnail image and nothing is displayed in the third area before the detection of the first selection of the ith thumbnail image.

3. The method of claim 1, wherein the display includes a distribution list display area that displays lesion distributions in the plurality of similar medical images.

* * * * *